(12) United States Patent
Eby et al.

(10) Patent No.: US 10,406,354 B2
(45) Date of Patent: Sep. 10, 2019

(54) MEDICAL TOOL EMPLOYING A WARNING MECHANISM NOTIFYING THAT A ROTATIONAL LIMIT HAS BEEN REACHED

(71) Applicant: Pacesetter, Inc., Sunnyvale, CA (US)

(72) Inventors: Thomas B. Eby, Mountain View, CA (US); Bradley Knippel, Lino Lakes, MN (US); Daniel Coyle, St. Louis Park, MN (US); Jennifer Heisel, Princeton, MN (US); Bernhard Arnar, Minnetrista, MN (US); Brett Hillukka, Hanover, MN (US); Tracee Eidenschink, Wayzata, MN (US); Paul Paspa, Los Gatos, CA (US); Joseph Ramon Callof, San Mateo, CA (US)

(73) Assignee: PACESETTER, INC., Sylmar, CA (US)

(*) Notice: Subject to any disclaimer, the term of this patent is extended or adjusted under 35 U.S.C. 154(b) by 104 days.

(21) Appl. No.: 15/681,173

(22) Filed: Aug. 18, 2017

(65) Prior Publication Data

US 2018/0050191 A1 Feb. 22, 2018

Related U.S. Application Data

(60) Provisional application No. 62/377,435, filed on Aug. 19, 2016.

(51) Int. Cl.
*A61N 1/05* (2006.01)
*A61N 1/372* (2006.01)
*A61N 1/375* (2006.01)
*A61B 17/34* (2006.01)
*A61M 25/00* (2006.01)
*A61N 1/362* (2006.01)
(Continued)

(52) U.S. Cl.
CPC .......... *A61N 1/057* (2013.01); *A61B 17/3468* (2013.01); *A61M 25/0082* (2013.01); *A61N 1/375* (2013.01); *A61N 1/3756* (2013.01); *A61N 1/37205* (2013.01); *A61N 1/37518* (2017.08); *A61B 2090/031* (2016.02); *A61M 25/0136* (2013.01); *A61M 2207/00* (2013.01); *A61N 1/3627* (2013.01)

(58) Field of Classification Search
CPC .. A61N 1/0573; A61N 1/057; A61N 1/37518; A61B 2090/031; A61M 25/0082
See application file for complete search history.

(56) References Cited

U.S. PATENT DOCUMENTS 4,586,074 A 4/1986 Stapelbroek et al.
5,246,014 A 9/1993 Williams et al.
(Continued)

FOREIGN PATENT DOCUMENTS

WO 2007/047681 A2 4/2007

OTHER PUBLICATIONS

Related Patent Application, U.S. Appl. No. 15/681,178, filed Aug. 18, 2017.
(Continued)

*Primary Examiner* — Alyssa M Alter
(74) *Attorney, Agent, or Firm* — Theresa A. Raymer

(57) ABSTRACT

A medical tool includes a rotation mechanism that further includes a warning feature. The warning feature provides an indication when the rotation mechanism has achieved a number of rotations.

13 Claims, 32 Drawing Sheets

(51) Int. Cl.
*A61M 25/01* (2006.01)
*A61B 90/00* (2016.01)

(56) References Cited

U.S. PATENT DOCUMENTS

| | | | |
|---|---|---|---|
| 5,456,708 | A | 10/1995 | Doan et al. |
| 5,821,744 | A | 10/1998 | Shinjo et al. |
| 5,837,006 | A | 11/1998 | Ocel et al. |
| 6,033,414 | A | 3/2000 | Tockman et al. |
| 6,687,550 | B1 | 2/2004 | Doan et al. |
| 6,931,286 | B2 | 8/2005 | Sigg et al. |
| 7,158,838 | B2 | 1/2007 | Seifert et al. |
| 7,657,362 | B2 | 2/2010 | Ando et al. |
| 7,801,622 | B2 | 9/2010 | Camps et al. |
| 7,937,148 | B2 | 5/2011 | Jacobson |
| 7,945,333 | B2 | 5/2011 | Jacobson |
| 8,010,209 | B2 | 8/2011 | Jacobson |
| 8,352,025 | B2 | 1/2013 | Jacobson |
| 8,457,742 | B2 | 6/2013 | Jacobson |
| 8,478,431 | B2 | 7/2013 | Griswold et al. |
| 8,486,128 | B2 | 7/2013 | Jen et al. |
| 9,205,225 | B2 | 12/2015 | Khairkhahan et al. |
| 2002/0188340 | A1 | 12/2002 | Bischoff et al. |
| 2003/0114907 | A1 | 6/2003 | Laabs et al. |
| 2003/0167082 | A1 | 9/2003 | Ollivier et al. |
| 2004/0068299 | A1 | 4/2004 | Laske et al. |
| 2004/0147963 | A1 | 7/2004 | Sommer et al. |
| 2004/0172116 | A1 | 9/2004 | Seifert et al. |
| 2005/0070984 | A1 | 3/2005 | Sundberg et al. |
| 2007/0088396 | A1 | 4/2007 | Jacobson |
| 2007/0088397 | A1 | 4/2007 | Jacobson |
| 2008/0039823 | A1 | 2/2008 | Shimogami et al. |
| 2008/0288040 | A1 | 11/2008 | Eckerdal et al. |
| 2008/0319520 | A1 | 12/2008 | Hill et al. |
| 2009/0105776 | A1 | 4/2009 | Aldridge et al. |
| 2010/0130854 | A1* | 5/2010 | Shachar ............ A61B 5/06 600/424 |
| 2010/0222860 | A1 | 9/2010 | Casella et al. |
| 2012/0116394 | A1* | 5/2012 | Timm .......... A61B 17/00234 606/45 |
| 2013/0012779 | A1 | 1/2013 | Frassica et al. |
| 2016/0096001 | A1 | 4/2016 | Eidenschink et al. |
| 2016/0310196 | A1 | 10/2016 | Johansson et al. |
| 2017/0274198 | A1 | 9/2017 | DuPont et al. |

OTHER PUBLICATIONS

Related Patent Application, U.S. Appl. No. 15/681,181, filed Aug. 18, 2017.
Related Patent Application, U.S. Appl. No. 15/681,188, filed Aug. 18, 2017.
Related Patent Application, U.S. Appl. No. 15/681,196, filed Aug. 18, 2017.
NonFinal Office Action, dated Sep. 25, 2018—Related Application, U.S. Appl. No. 15/681,181.
Non Final Office Action dated Jan. 28, 2019, U.S. Appl. No. 15/681,178, filed Aug. 18, 2017.
Non Final Office Action dated Mar. 22, 2019, U.S. Appl. No. 15/681,188, filed Aug. 18, 2017.

* cited by examiner

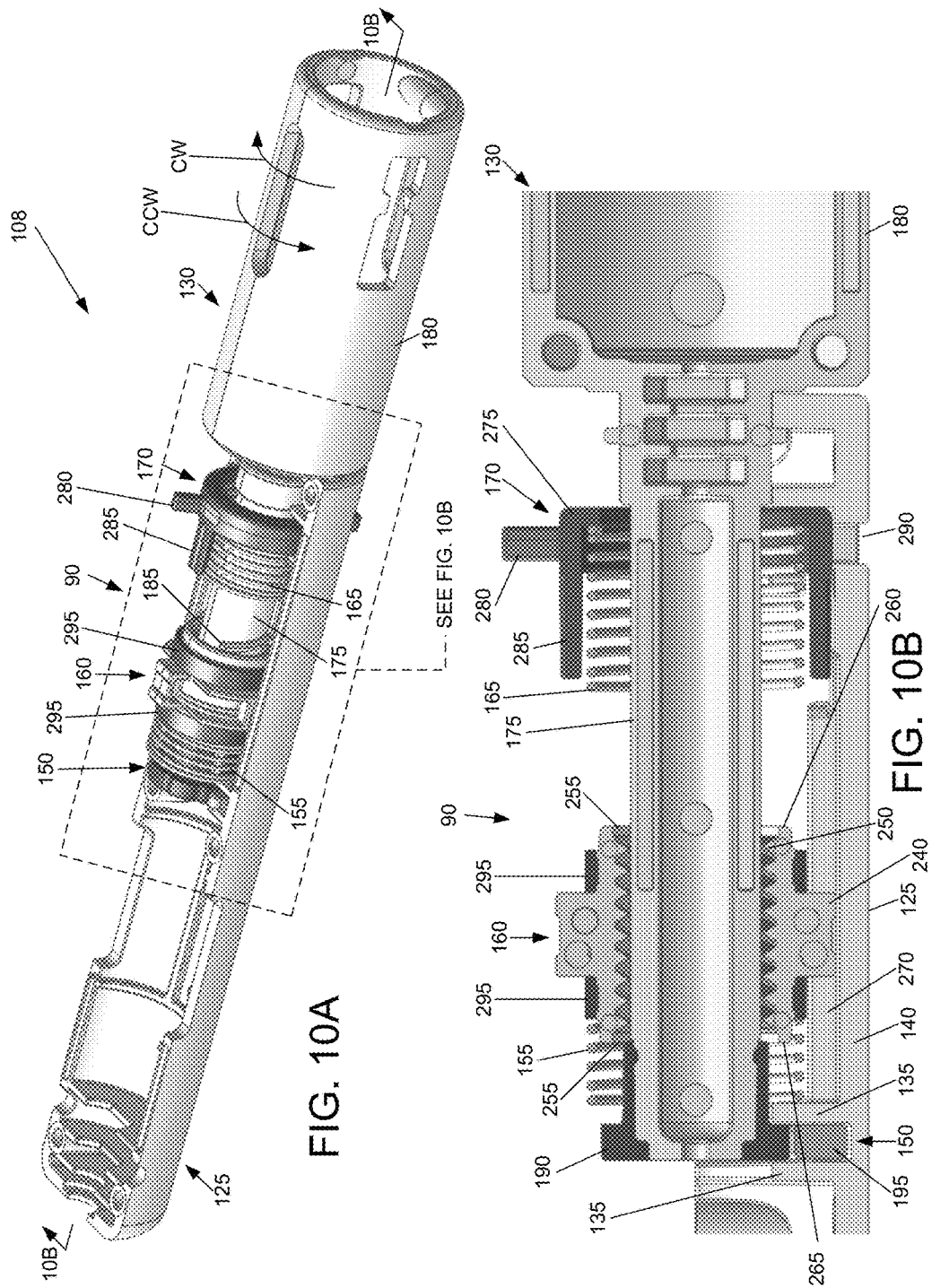

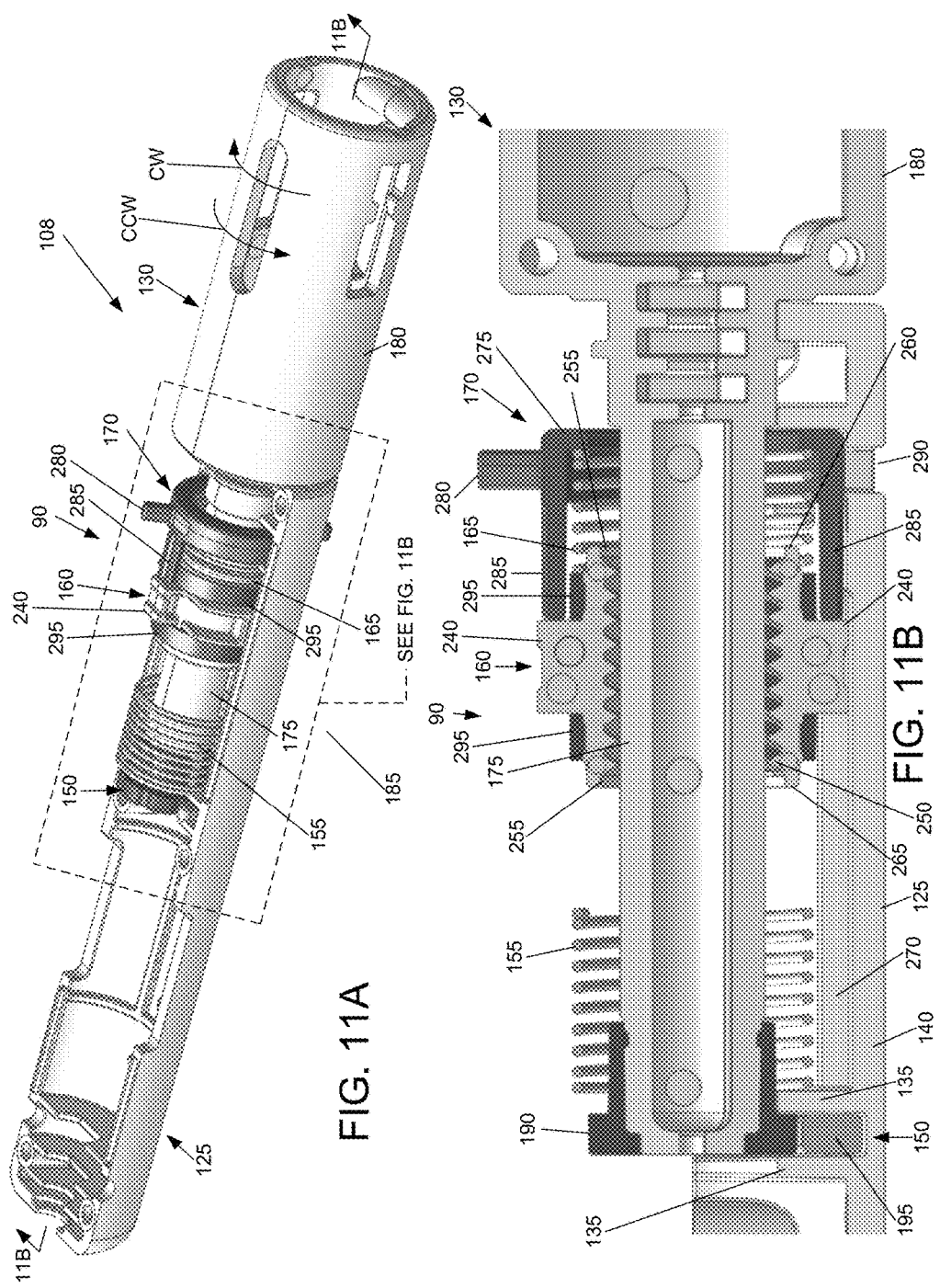

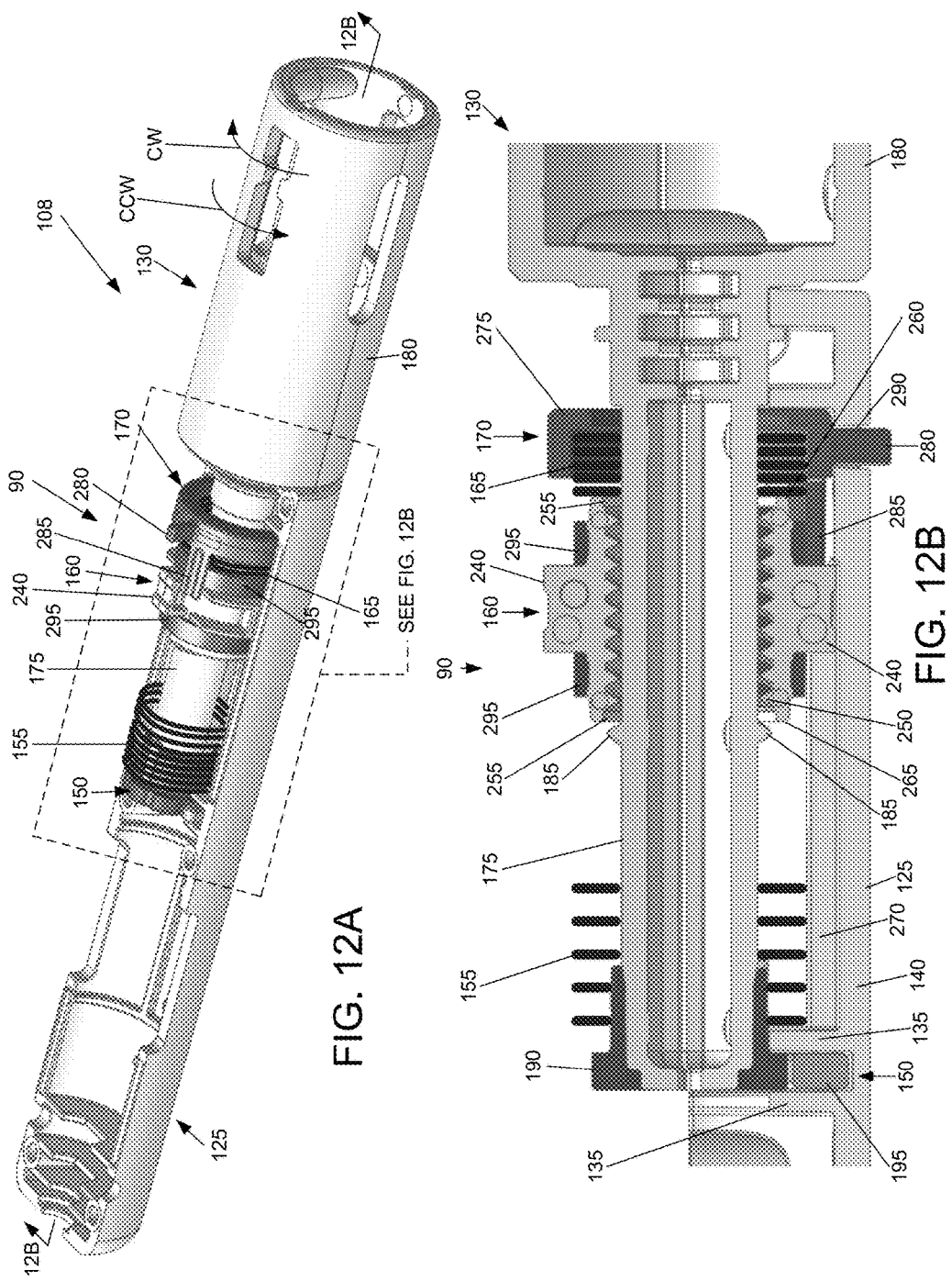

MEDICAL TOOL EMPLOYING A WARNING MECHANISM NOTIFYING THAT A ROTATIONAL LIMIT HAS BEEN REACHED

CROSS-REFERENCE TO RELATED APPLICATION

This application claims the benefit of and priority to U.S. Provisional Patent Application Ser. No. 62/377,435, filed Aug. 19, 2016, entitled, "MEDICAL TOOL EMPLOYING A WARNING MECHANISM NOTIFYING THAT A ROTATIONAL LIMIT HAS BEEN REACHED."

FIELD OF THE INVENTION

Aspects of the present invention relate to medical apparatus and methods. More specifically, the present invention relates to a medical tool for the delivery, implantation, actuation and/or manipulation of an implantable device and/or patient tissue, such as a leadless pacemaker.

BACKGROUND OF THE INVENTION

Leadless pacemakers and their delivery systems are a new technology. Similar to implantable leads that extend from a traditional pacemaker or implantable cardioverter defibrillator (ICD), there are essentially two fixation mechanisms for anchoring the leadless pacemaker to the endocardium; tines that get pulled into tissue and a helix that is rotated to fixate to cardiac tissue (similar to a screw).

For leadless pacemakers that require rotation for fixation, there are a number of possible clinical events that can occur as a result of over or under-rotating the leadless pacemaker. If the leadless pacemaker is under-rotated, it can come loose prior to full release or migrate post-release.

If the leadless pacemaker is over-rotated, the helix portion of the leadless pacemaker can either penetrate or pinch tissue. This penetration/pinching can potentially lead to a variety of adverse clinical events.

There is a need in the art for a system for, and method of, delivering a leadless pacemaker for fixation to cardiac tissue while reducing the possibility of under/over rotation of the leadless pacemaker during fixation.

BRIEF SUMMARY OF THE INVENTION

Disclosed herein is a warning mechanism for informing the physician regarding the number of rotations associated with the fixation of the leadless pacemaker, the warning mechanism being supported on a delivery system for the delivery and fixation of the leadless pacemaker to cardiac tissue. In one embodiment, the warning system is supported on the handle of the delivery system, the handle having a torque portion, which when rotated, causes the leadless pacemaker to rotate.

The purpose of the warning mechanism is to provide the physician with information about how many rotations of the leadless pacemaker have occurred in the course of trying to anchor the leadless pacemaker to cardiac tissue via the delivery system. When the warning system provides notice to the physician that a certain number of rotations of the leadless pacemaker have occurred, the physician needs to consciously think about progressing further in the procedure.

In order to progress with rotating the leadless pacemaker past the point where the warning mechanism has notified the physician that the certain number of rotations has been reached, the physician needs to make a conscious choice to proceed, which can occur in a number of ways, depending on the embodiment of the warning mechanism. For example, the physician must actuate or disable a feature of the warning mechanism to allow further rotations. Additionally or alternatively, the physician must overcome a temporary or short term increase in resistance to bringing about further rotation of the leadless pacemaker. Additionally or alternatively, the physician may overcome a warning to bring about further rotation of the leadless pacemaker for a pre-designed number of additional implant rotations, or implant partial rotations, whereby the delivery system torque portion enters a freewheel mode of infinite rotations.

The warning mechanism is advantageous in that it allows for the leadless pacemaker to be removed and repositioned and yet provide repeated warnings to the physician when the certain number of rotations have been reached, the warning mechanism being resettable or self-resetting to allow for repeated removal/reposition/anchoring of the leadless pacemaker.

In one embodiment, the warning mechanism informs the physician of a certain level of leadless pacemaker rotations by changing the amount of effort needed to continue rotating a torque portion of a handle of the delivery system for a short period of time. As the torque portion is being rotated clockwise (CW) initially, the effort required is relatively low as a shuttle translates along the handle body. Once the shuttle contacts an O-ring, the effort required to continue rotating increases significantly. In order for the physician to continue rotating the torque portion and the leadless pacemaker operably coupled to the torque portion, the physician simply needs to increase rotational force applied to the torque portion. As the rotation force applied to the torque portion is increased, the shuttle could either expand/open slightly and/or the O-ring could be compressed slightly. A thread on a handle shaft continues to translate the shuttle until the shuttle has cleared the O-ring. Once the shuttle has cleared the O-ring, the effort required to rotate the handle returns to normal. The shuttle may cover the O-ring at this point, but does not interfere with it. This non-interference allows the feel of the torque portion to return to normal after the O-ring has been cleared. At this point, the user is free to rotate the handle in the clock-wise direction freely without a secondary warning system, although in some embodiments, additional O-ring could be employed to give additional incremental warnings.

If the physician needs to re-position the leadless pacemaker, the torque portion of the handle only needs to be turned in the opposite direction (counter-clockwise (CCW)). In order for the shuttle to properly re-engage the thread, a spring with sufficient enough force biases the shuttle up against the shaft thread segment of the torque portion of the handle. When the torque portion gets rotated CCW with the shuttle in contact with the shaft thread segment, the shuttle begins translating towards the distal end of the handle. To clear the O-ring, the shuttle again needs to expand slightly and/or compress the O-ring. Once the shuttle has cleared the O-ring, the physician can continue rotating the torque portion of the handle with normal effort until the leadless pacemaker is completely removed from cardiac tissue. Once the physician has repositioned the leadless pacemaker to a desired location, the mechanism starts over, and will again inform the user at the set torque portion rotation level as another spring biases the shuttle back into threaded engagement with the shaft thread segment as the torque portion is rotated CW.

In one embodiment, the system employs bumps on the housing that are contacted by complementary bumps on the shuttle to provide a warning mechanism that informs the physician of a certain level of leadless pacemaker rotations by changing the amount of effort needed to continue rotating a torque portion of a handle of the delivery system for a short period of time. The bumps operate similarly to the operation of the O-ring. Specifically, a pair of plastic bumps exists along a shuttle track. The pair of plastic bumps are contacted at a certain rotation level by similar features on the shuttle. In order to move the shuttle past the shuttle track bumps and continue rotating the torque portion, the user would need to rotate the torque portion with greater/conscious effort. Once the interference/bump is cleared, the torque portion of the handle would return to normal with respect to rotational feel.

In one embodiment, the warning mechanism informs the physician of the handle rotation level by providing a hard or soft stop at a certain number of turns of the torque portion of the handle in place of, or additional to, employing the O-ring or bumps. A helical partial thread on the shaft translates a shuttle towards the proximal end. When the rotation limit is reached, the shuttle comes in contact with a mechanical or electro-mechanical obstacle, which physically prevents it from translating further, and subsequently prevents the torque portion of the handle from further rotating the shaft and, by extension, the leadless pacemaker. In order for the physician to continue rotating the torque portion and the leadless pacemaker, the physician needs to intentionally displace the switch to remove the obstacle inhibiting the shuttle. Once the switch is displaces, the shuttle is again free to translate, which allows the torque portion and leadless pacemaker to rotate freely.

After the switch is displaced, if the physician needs to unscrew the leadless pacemaker and re-position the leadless pacemaker, the physician simply rotates the handle in the other direction. By rotating the torque portion of the handle in the CCW direction, the shuttle re-engages the helical partial thread on the shaft and will translate distally until it is back at its starting point. The user would then return the switch to its starting point in order for the warning mechanism to function a second time as the shuttle is moved proximally as the torque portion of the handle is rotated CW.

Disclosed herein is a medical tool. In one embodiment, the tool includes a handle, a torque portion, a shuttle, and a warning mechanism. The torque portion is operably coupled to the housing and rotatable relative to the housing. The torque portion includes a shaft including an outer circumferential surface and a helical thread portion radially outwardly extending from the outer circumferential surface of the shaft. The shuttle is displaceable along the shaft via threaded interaction with the helical thread portion. The warning mechanism interacting with the shuttle provides a tactile indication when the torque portion has rotated a number of rotations.

The warning mechanism may include an O-ring on the shaft that is deflected by the shuttle as the shuttle passes over the O-ring, the deflection providing the tactile indication. For example, the O-ring may be deflected by a lip of the shuttle. Also, the shuttle may include a region inward of the lip that allows the O-ring to return to its non-deflected shape within the confines of the shuttle. The tactile indication may include a period of increased rotational resistance at the torque portion as the O-ring is being deflected by the shuttle.

The warning mechanism may include a structural feature on the housing that is contacted by a structural feature on the shuttle as the shuttle displaces along the shaft. For example, the structural feature on the housing may include a bump, and the structural feature on the shuttle may include a bump, at least one of the bumps deflecting as the shuttle displaces along the shaft, the deflection providing the tactile indication. The tactile indication may include a period of increased rotational resistance at the torque portion as the at least one of the bumps is being deflected.

The warning mechanism may include a hard stop contactable by the shuttle near a proximal end of the displacement of the shuttle along the shaft, the tactile indication being provided by the shuttle contacting the hard stop. The hard stop can be moved out of alignment with the shuttle such that the shuttle can be further proximally displaced along the shaft.

The shaft may include a first end and a second end opposite the first end. The shaft may be capable of infinite rotation in a first direction without causing further displacement of the shuttle along the shaft toward the first end when the shuttle is at a first location near the first end. Also, rotation of the shaft in a second direction opposite the first direction when the shuttle is at the first location causes the shuttle to displace along the shaft towards the second end.

The shaft may also be capable of infinite rotation in the second direction without causing further displacement of the shuttle along the shaft toward the second end when the shuttle is at a second location near the second end. Also, rotation of the shaft in the first direction when the shuttle is at the second location causes the shuttle to displace along the shaft towards the first end.

The tool may also include a first biasing element that biases the shuttle towards the second end when the shuttle is at the first location, and a second biasing element that biases the shuttle towards the first end when the shuttle is at the second location.

Disclosed herein is a medical tool. In one embodiment, the tool includes a rotation mechanism including a warning feature that provides a tactile indication when the rotation mechanism has achieved a number of rotations.

In one embodiment, the tactile indication is provided by interference between parts of the rotation mechanism. For example, the interference may be between an O-ring on a shaft of the rotation mechanism that is compressed by a shuttle that displaces along the shaft and is driven by the shaft. As another example, the interference may be between a shuttle of the rotation mechanism and a handle housing of the medical tool.

In one embodiment, the tactile indication includes a period of increased rotational resistance at a torque portion of a handle of the tool.

In one embodiment, the tactile indication may be provided by a shaft driven shuttle of the rotation mechanism contacting a hard stop aligned with the shuttle. The hard top can be placed out of alignment with the shuttle to allow further displacement of the shuttle.

In one embodiment, a drive shaft of the rotation mechanism includes a first end and a second end opposite the first end. The drive shaft is capable of infinite rotation in a first direction without causing further displacement of the shuttle along the drive shaft toward the first end when the shuttle is at a first location near the first end. Rotation of the drive shaft in a second direction opposite the first direction when the shuttle is at the first location causes the shuttle to displace along the drive shaft towards the second end.

The drive shaft is capable of infinite rotation in the second direction without causing further displacement of the shuttle along the drive shaft toward the second end when the shuttle is at a second location near the second end. Rotation of the drive shaft in the first direction when the shuttle is at the second location causes the shuttle to displace along the drive shaft towards the first end.

A first biasing element of the rotation mechanism biases the shuttle towards the second end when the shuttle is at the first location. A second biasing element of the rotation mechanism biases the shuttle towards the first end when the shuttle is at the second location.

Also disclosed herein is a delivery system. In one embodiment, the delivery system includes a handle, a torque portion, a shuttle, and a warning mechanism. The torque portion is operably coupled to the housing and rotatable relative to the housing. The torque portion includes a shaft including an outer circumferential surface and a helical thread portion radially outwardly extending from the outer circumferential surface of the shaft. The shuttle is displaceable along the shaft via threaded interaction with the helical thread portion. The electronic warning mechanism interacting with the shuttle provides an indication when the torque portion has rotated a number of rotations. The indication provided by the warning mechanism may be, among other things, a visual, audial, or tactile indication. In one embodiment, the number of rotations is determined based on a variable resistance element that interacts with the shuttle such that as the shuttle is displaced along the shaft, a resistance of the variable resistance element changes. In another embodiment, the number of rotations is determined by a switch disposed in the housing that is actuated when the shuttle reaches a predetermined position along the shaft corresponding to the number of rotations of the shaft.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 10A is an isometric view of the handle with a portion of a housing removed to reveal the rotation mechanism enclosed therein, the shuttle being in a most distal location along a shaft of the torque portion of the handle.

FIG. 10B is a longitudinal cross-section of the rotation mechanism in the region identified in FIG. 10A and as taken along section line 10B-10B in FIG. 10A.

FIG. 11A is the same view as FIG. 10A, except the shuttle is in a proximal location along the shaft of the torque portion of the handle and an abutment of the shuttle abuts against a hard stop of a stop ring.

FIG. 11B is a longitudinal cross-section of the rotation mechanism in the region identified in FIG. 11A and as taken along section line 11B-11B in FIG. 11A.

FIG. 12A is the same view as FIG. 11A, except the shuttle is in a most distal location along the shaft of the torque portion of the handle, a lever of the stop ring having been used to rotate the stop ring about a longitudinal axis of the shaft of the torque portion of the handle such that the hard stop of the stop ring is rotated so as to be clear of the abutment of the shuttle, the shuttle thereby being free to proceed more proximally than depicted in FIG. 11A.

FIG. 12B is a longitudinal cross-section of the rotation mechanism in the region identified in FIG. 12A and as taken along section line 12B-12B in FIG. 12A.

DETAILED DESCRIPTION

Figure 1:
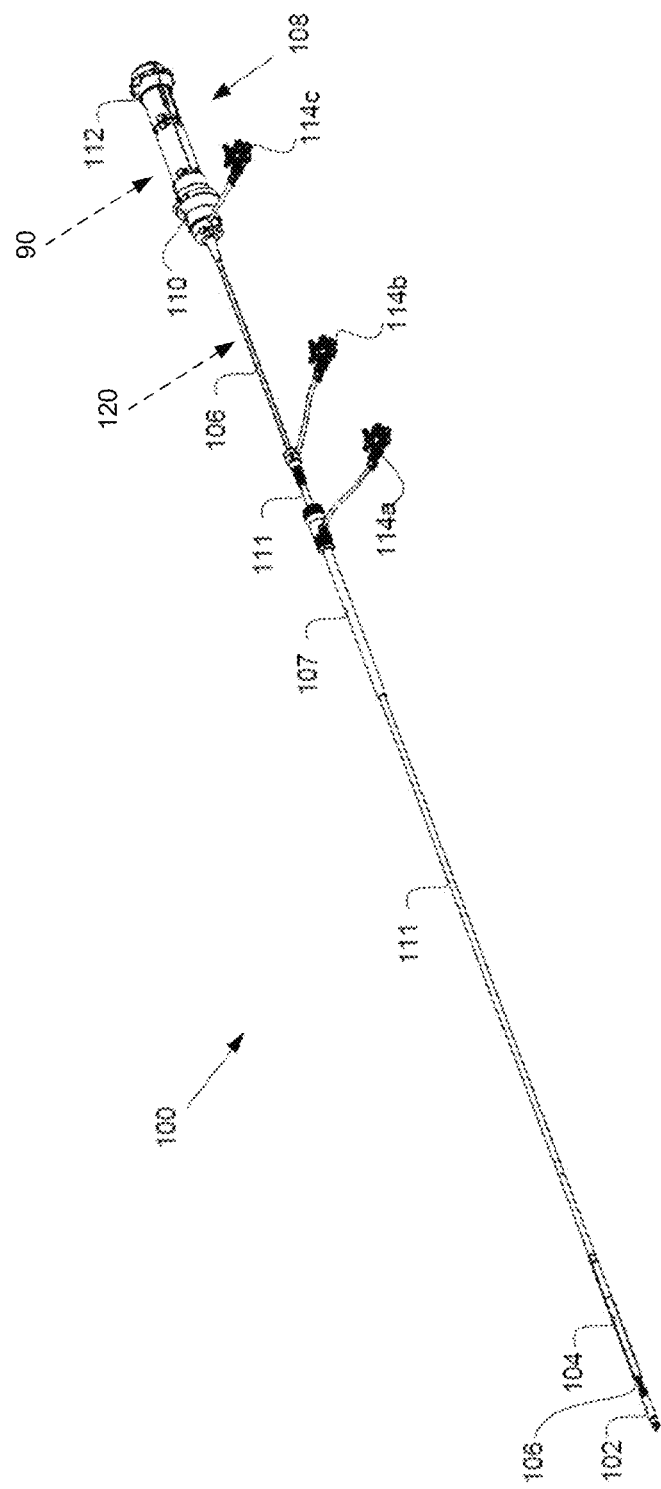
FIG. 1 is an isometric view of an example of a leadless pacemaker delivery system employing the rotation mechanism disclosed herein.

Implementations of the present disclosure involve a medical tool including a rotation mechanism having a warning feature that provides a tactile indication when the rotation mechanism has achieved a number of rotations. The tactile indication may be provided via, for example, deflection or compression of a resilient member such as an O-ring.

Alternatively or additionally, the tactile indication may be provided by interference of structural members contacting each other, such as bumps on one element being brought into contact with bumps on another element, one or more of the bumps being caused to deflect on account of the contact.

Alternatively or additionally, the tactile indication may be provided via abutting contact between elements of the rotation mechanism, such as contact between a hard contact of a stop ring and a surface of a shuttle. The hard contact of the stop ring may be rotated out of alignment with the surface of the shuttle to facilitate resumed displacement of the shuttle.

The rotation mechanism is advantageous as it may be configured for infinite rotation in a first direction when the shuttle is at a first location on a shaft of the rotation mechanism, and infinite rotation in a second direction opposite the first direction when the shuttle is at a second location on the shaft opposite the first location. Further, the shuttle may biased such that rotation in the second direction when the shuttle is at the first location results in displacement of the shuttle towards the second location, and rotation in the first direction when the shuttle is at the second location results in displacement of the shuttle towards the first location.

Before discussing the specifics of the rotation mechanism and the warning features disclosed here, a discussion will now be provided regarding an example medical tool employing the rotation mechanism and the warning features.

A. Overview of Example Tool Embodiments Employing the Rotation Mechanism

The rotation mechanism 90 disclosed herein and discussed in detail below may be beneficially employed in a wide variety medical tools. For example, in one embodiment, the rotation mechanism 90 may be employed in the handle 108 of a leadless pacemaker delivery system 100 configured to deliver into a patient a leadless pacemaker 102 such as the Nanostim™ leadless pacemaker as manufactured by Abbott.

Typically, a leadless pacemaker is substantially enclosed in a hermetic housing suitable for placement on or attachment to the inside or outside of a cardiac chamber. Depending on the embodiment, the pacemaker can have two or more electrodes located within, on, or near the housing, for delivering pacing pulses to muscle of the cardiac chamber and optionally for sensing electrical activity from the muscle, and for bidirectional communication with at least one other device within or outside the body. The housing can contain a primary battery to provide power for pacing, sensing, and communication, for example bidirectional communication. The housing can optionally contain circuits for sensing cardiac activity from the electrodes. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner.

In some embodiments, a leadless pacemaker can be adapted for delivery and implantation into tissue in the human body. In a particular embodiment, a leadless pacemaker can be adapted for implantation adjacent to heart tissue on the inside or outside wall of a cardiac chamber, using two or more electrodes located on or within the housing of the pacemaker, for pacing the cardiac chamber upon receiving a triggering signal from at least one other device within the body.

Self-contained or leadless pacemakers or other biostimulators are typically fixed to an intracardial implant site by an actively engaging mechanism or primary fixation mechanism such as a screw or helical member that screws into the myocardium. Examples of such leadless biostimulators are described in the following publications, the disclosures of which are incorporated by reference herein in their entireties: (1) U.S. Pat. No. 8,457,742; (2) U.S. application Ser. No. 11/549,581 filed on Oct. 13, 2006, entitled "Leadless Cardiac Pacemaker", and published as US2007/0088396A1 on Apr. 19, 2007; (3) U.S. application Ser. No. 11/549,591, filed on Oct. 13, 2006, entitled "Leadless Cardiac Pacemaker System with Conductive Communication" and published as US2007/0088397A1 on Apr. 19, 2007; (4) U.S. Pat. No. 8,352,025; (5) U.S. Pat. No. 7,937,148; (6) U.S. Pat. No.

7,945,333; (7) U.S. Pat. No. 8,010,209; and (8) International Application No. PCT/US2006/040564, filed on Oct. 13, 2006, entitled "Leadless Cardiac Pacemaker and System" and published as WO07047681A2 on Apr. 26, 2007.

Leadless pacemakers or biostimulators can be delivered to, and retrieved from, a patient using a delivery system 100 similar to that described below with respect to FIG. 1, which is an isometric view of the delivery system 100. As illustrated in FIG. 1, the delivery system 100 can include a guide catheter sheath 111 including an atraumatic distal end 104 in the form of a pacemaker sheath 104. The delivery system 100 can also have a pacemaker introducer sheath 107 and a catheter shaft 106. The catheter shaft 106 includes at its proximal end the handle 108, a deflection knob 110, and a tether shuttle 112. Each of the longitudinal bodies 107, 111, 106 includes a flush port 114*a*, 114*b*, 114*c* extending respectively therefrom. As can be understood from FIG. 1, the catheter shaft 106 extends through the guide catheter sheath 111, which extends through the introducer sheath 107. Each of the longitudinal bodies 106, 107, 111 are displaceable proximal-distal relative to each other.

As discussed in detail in U.S. Publication No. 20160096001, which is entitled "DELIVERY CATHETER SYSTEMS AND METHODS," filed Oct. 7, 2014, hereby incorporated by reference in its entirety herein, in one embodiment, the atraumatic pacemaker sheath 104 may have a braided or woven construction that is sufficiently flexible to allow the atraumatic pacemaker sheath 104 to encompass the leadless pacemaker 102 or to have a diameter that is smaller than a diameter of the leadless pacemaker 102 when not encompassing the leadless pacemaker 102. The deflection knob 110 can be used to deflect the catheter shaft 106 within the catheter sheath 111 to steer and guide the catheter during implantation and/or removal of the pacemaker. The flush ports 114*a*, 114*b*, and 114*c* can be used to flush saline or other fluids through the catheter. The atraumatic sheath 104 forms the distal most region of the catheter sheath 111. The catheter sheath 111 can be advanced distally over the catheter shaft 106 such that the atraumatic sheath 104 is caused to extend over the leadless pacemaker 102. Also, the distal displacement of catheter sheath 111 relative to the catheter shaft 106 can be used to provide additional steering and support for the delivery catheter during implantation and to surround the pacemaker as it is introduced through a trocar or the introducer sheath 107 into the patient. The catheter sheath 111 can be retracted proximally over the catheter shaft 106 such that the atraumatic sheath 104 is caused to retract from over the leadless pacemaker 102, the braided construction of atraumatic sheath 104 being such that the atraumatic sheath 104 self-biases into a reduced diameter. The reduced diameter of the atraumatic sheath 104 is no greater than the diameter of the leadless pacemaker 102.

As can be understood from FIG. 1 and the above-referenced patent/applications, a leadless pacemaker 102 is attached or connected to a distal end of the delivery system 100 and advanced intravenously into the heart. As discussed in greater detail below, the rotation mechanism 90 incorporated in the handle 108 of the delivery system 100 can be used to cause a linear member 120 that extends longitudinally through the catheter shaft 106 and is operably coupled to the rotation mechanism 90 to rotate relative to the catheter shaft 106 about the longitudinal axis of the catheter shaft 106 to rotate the leadless pacemaker 102 about its longitudinal axis such that the distal helical anchor of the leadless pacemaker 102 screws into the cardiac tissue if the leadless pacemaker 102 is being implanted or to unscrew from the cardiac tissue if the leadless pacemaker 102 is being explanted.

Each of the rotation mechanisms 90 discussed below employ a rotation limit warning mechanism by which a physician is notified that a prescribed number of rotations of the helical anchor of the leadless pacemaker has been reached. Upon having received the rotation limit warning, the physician may elect to continue to further rotate the helical anchor in the direction of tissue anchoring, to leave the anchor as is with respect to direction and number of rotations, or to rotationally withdraw the helical anchor and again attempt to rotate the helical anchor into the cardiac tissue.

B. Handle with Rotation Mechanism Employing Stop Ring Rotation Limit Warning

Figure 2:
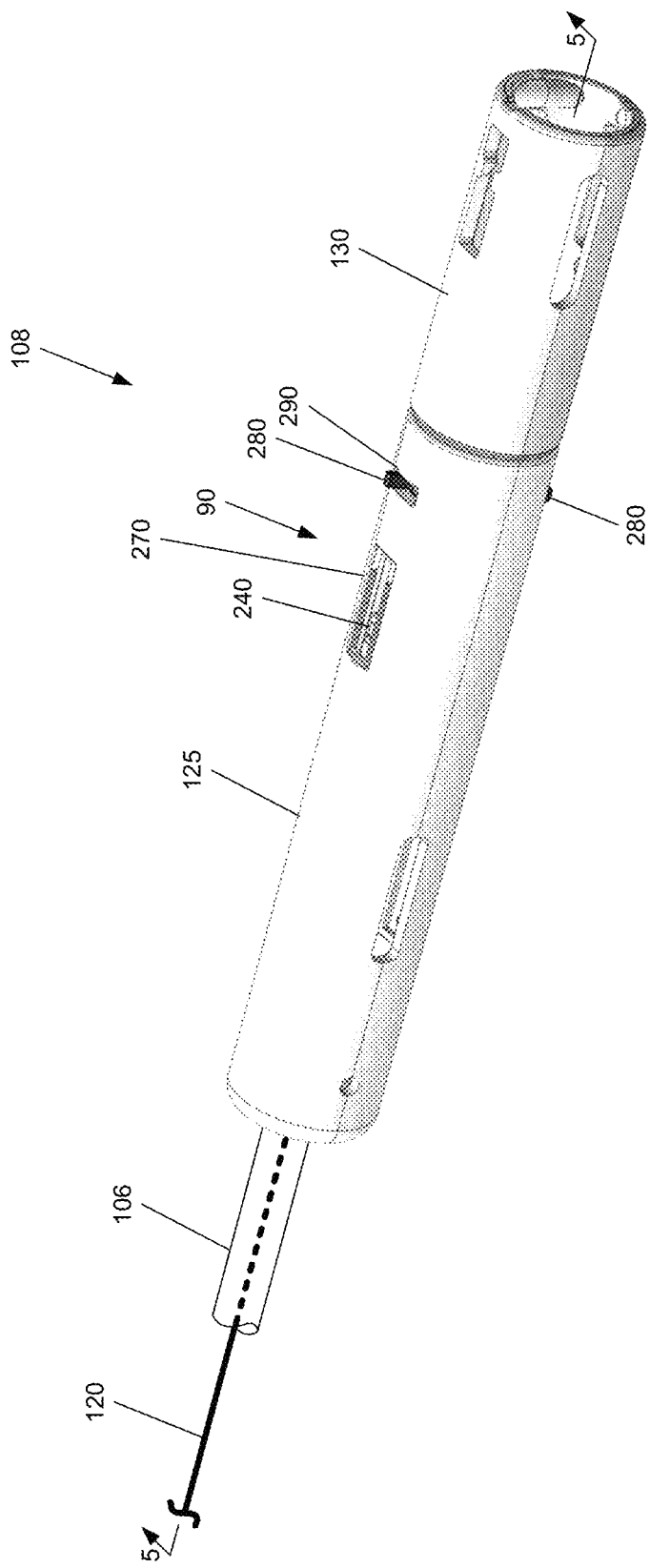
FIG. 2 is an isometric view of the proximal region of the leadless pacemaker delivery system, which includes a handle employing the rotation mechanism disclosed herein.

As shown in FIG. 2, which is an isometric view of the proximal region of the leadless pacemaker delivery system of FIG. 1, the handle 108 includes a housing portion 125 and a torque portion 130, which may be in the form of a torque knob 130. The housing portion 125 encloses the rotation mechanism 90 and is coupled to the catheter shaft 106. The torque portion 130 is operably coupled to the housing portion 125 such that the torque portion 130 can rotate relative to the housing portion 125 about a common longitudinal axis of the two portions 125, 130.

As described in detail below, rotation of the torque portion 130 relative to the housing portion 125 drives the rotation mechanism 90 to cause a similar rotation of the linear member 120 relative to the catheter shaft 106, the linear member 120 being operably coupled to the rotation mechanism 90.

As depicted in FIG. 2, in one embodiment, the torque portion 125 is proximal the distal housing portion 125. However, in other embodiments, the arrangement may be reversed proximal-distal.

Figure 3:
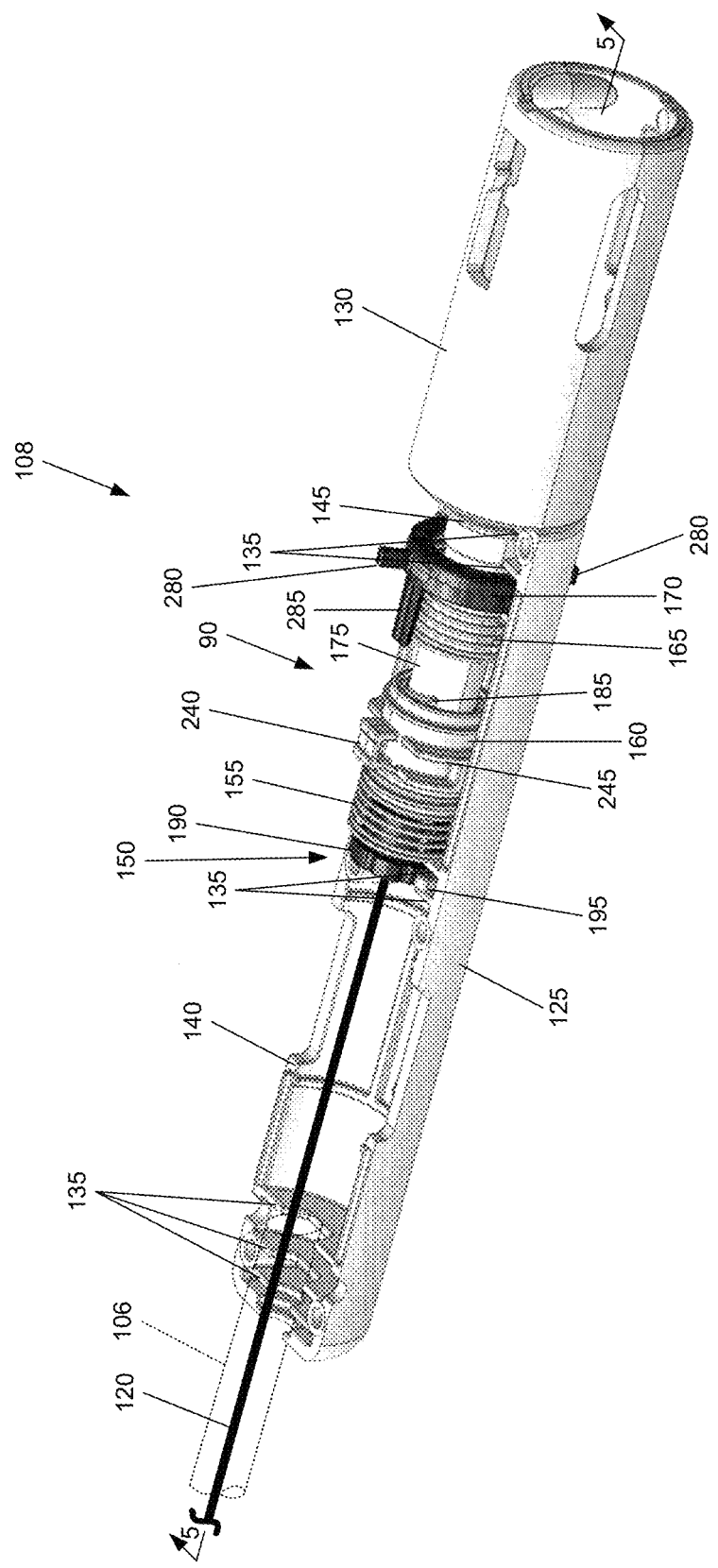
FIG. 3 is the same view as FIG. 2, except with a portion of a housing of the handle removed to reveal the rotation mechanism enclosed therein.

As illustrated in FIG. 3, which is the same view as FIG. 2, except with a half-shell of the housing portion 125 of the handle 108 removed to reveal the rotation mechanism 90 enclosed therein, the housing portion 125 may be a multi-piece construction that forms a shell that has various interior wall structures 135. The interior wall structures reinforce the outer wall 140 of the housing portion 125 and support and longitudinally separate various components of the rotation mechanism 90, the catheter shaft 106, and the torque portion 130. The housing portion 125 may be made of materials such as, for example, polymers, metals, and/or etc.

As indicated in FIG. 3, the catheter shaft 106 is secured to the distal region of the housing portion 125. The torque portion 130 has structural features, such as, for example, one or more circumferential grooves 145, that interface with some of the interior wall structures 135 to prevent the torque portion 130 from proximal-distal displacement relative to the housing portion 125 while supporting the torque portion 130 in rotating displacement relative to the housing portion 130, the rotation being about a common longitudinal axis of the housing portion and torque portion.

As can be understood from FIG. 3, the linear member 120 extends from a distal end of the rotation mechanism 90, through the interior of the housing portion 125, and through the catheter shaft 106. The proximal end of the linear member 120 is coupled to the distal end of the rotation mechanism 90 such that rotation of the rotation mechanism 90 causes the linear member 120 to similarly rotate within the confines of the housing portion 125 and the catheter shaft 106 about a longitudinal axis of the linear member 120. Thus, as can be understood from FIGS. 1-3, rotation of the torque portion 130 clockwise causes the linear member 120 to rotate clockwise, thereby causing the leadless pacemaker 102 at the distal end of the delivery system 100 to rotate clockwise about the longitudinal axis of the leadless pacemaker 102. This clockwise rotation will cause the helical anchor at the distal end of the leadless pacemaker to screw into the cardiac tissue to attach the leadless pacemaker to the cardiac tissue.

Oppositely, rotation of the torque portion 130 counter-clockwise causes the linear member 120 to rotate counter-clockwise, thereby causing the leadless pacemaker 102 at the distal end of the delivery system 100 to rotate counter-clockwise about the longitudinal axis of the leadless pacemaker 102. This counter-clockwise rotation will cause the helical anchor at the distal end of the leadless pacemaker to unscrew from the cardiac tissue to detach the leadless pacemaker from the cardiac tissue.

Figure 4:
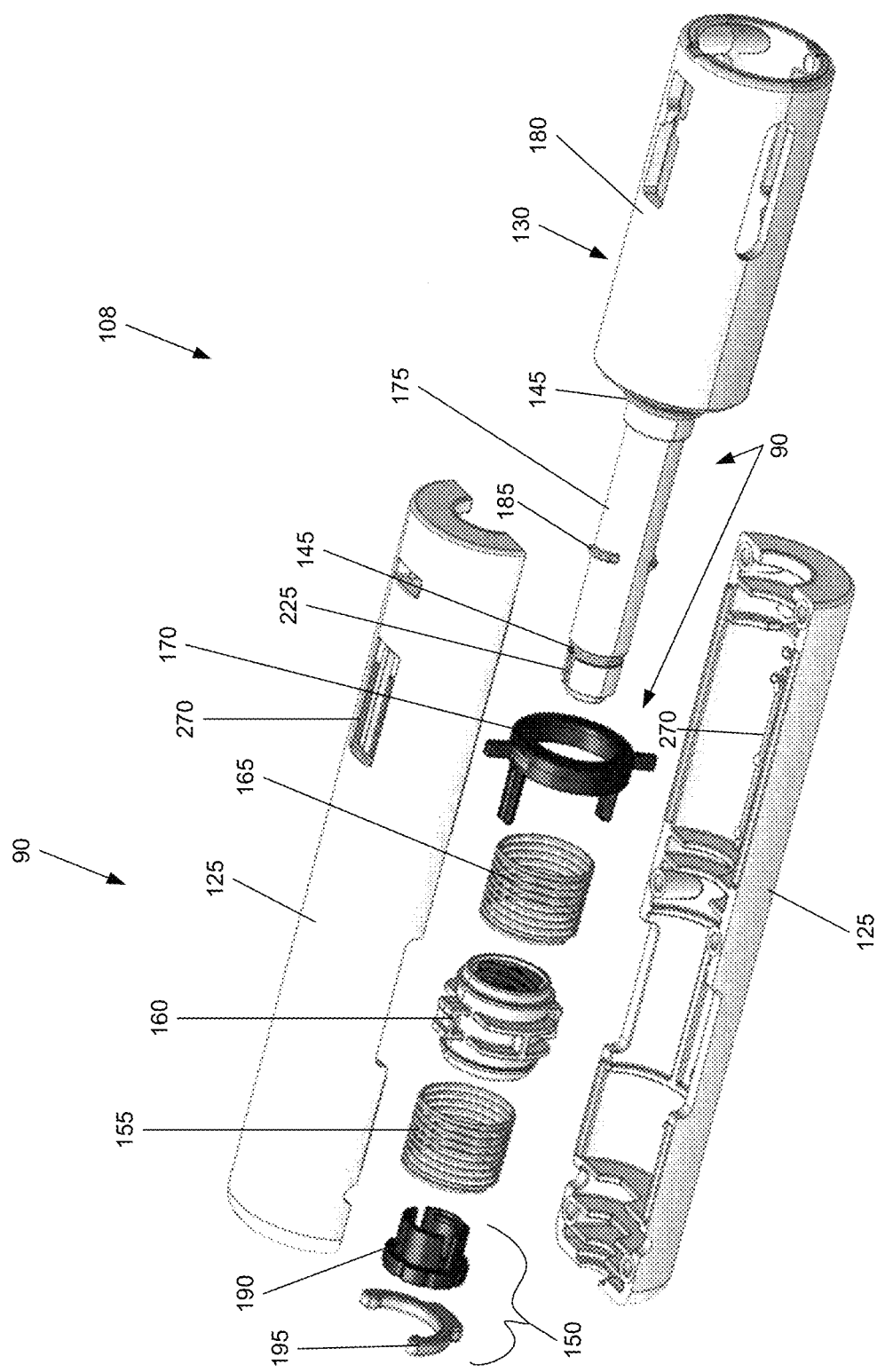
FIG. 4 is an exploded isometric view of the handle and rotation mechanism enclosed therein.

FIG. 4 is an exploded isometric view of the handle 108 and the rotation mechanism 90 enclosed therein. As shown in FIG. 4, the rotation mechanism 90 includes a ratchet assembly 150, a distal spring 155, a shuttle 160, a proximal spring 165, a stop ring 170 and a drive shaft 175 of the torque portion 130. These components of the rotation mechanism 90 are enclosed by the housing portion 125. The drive shaft 175 of the torque portion 130 distally extends from a grip 180 of the torque portion 130.

Figure 5:
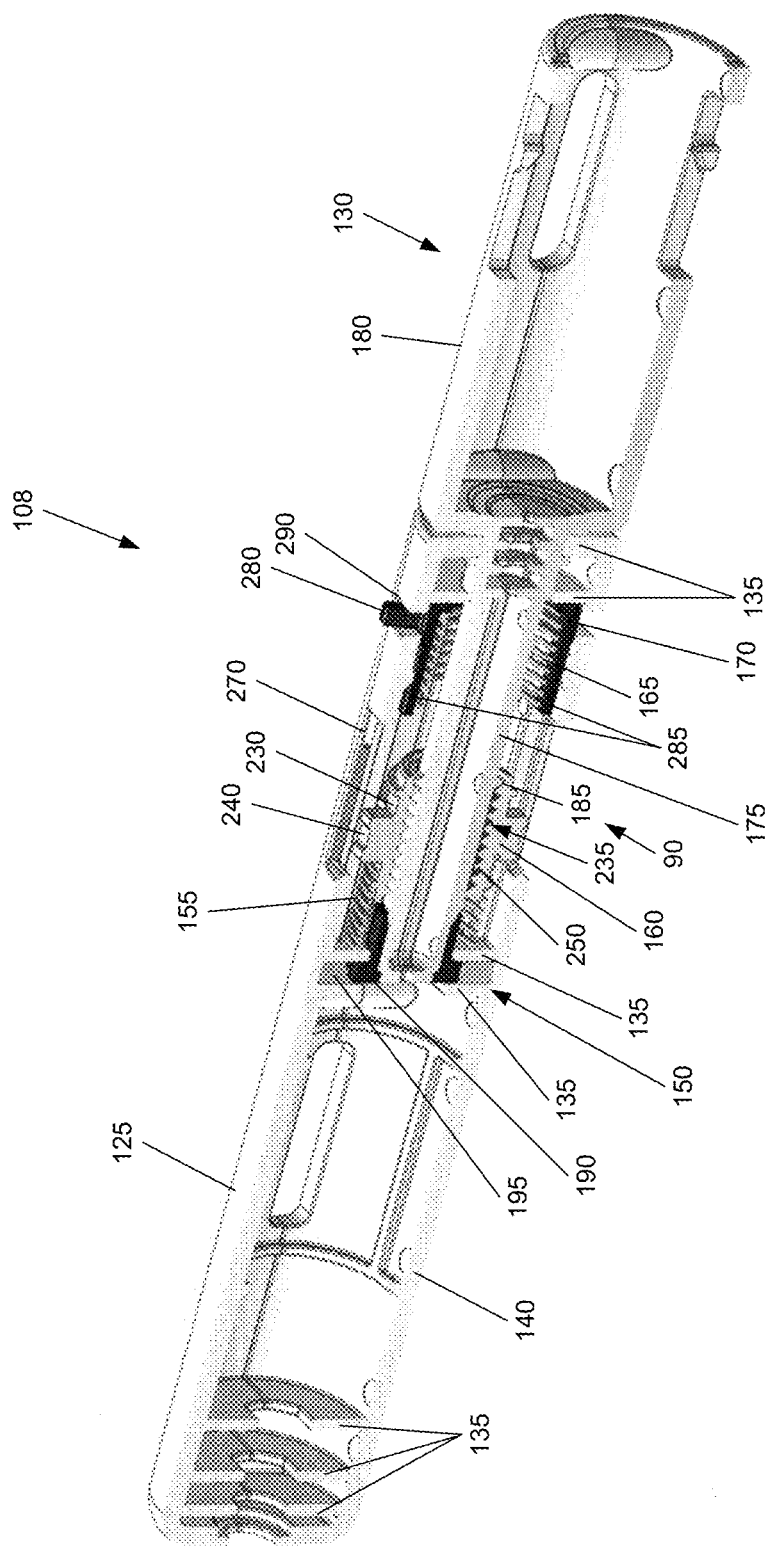
FIG. 5 is a longitudinal cross section of the handle and rotation mechanism enclosed therein as viewed along section line 5-5 in FIG. 2.

FIG. 5 is a longitudinal cross section of the handle 108 and rotation mechanism enclosed therein as viewed along section line 5-5 in FIG. 2. As can be understood from FIGS. 2-5, the drive shaft 175 distally extends from the grip 180 of the torque portion 130 into the housing portion 125 to be supported in a rotating fashion by various interior wall structures 135 of the housing portion 125. The drive shaft 175 extends through the other components of the drive mechanism 90, specifically, the ratchet assembly 150, the distal spring 155, the shuttle 160, the proximal spring 165, and the stop ring 170.

Figure 6:
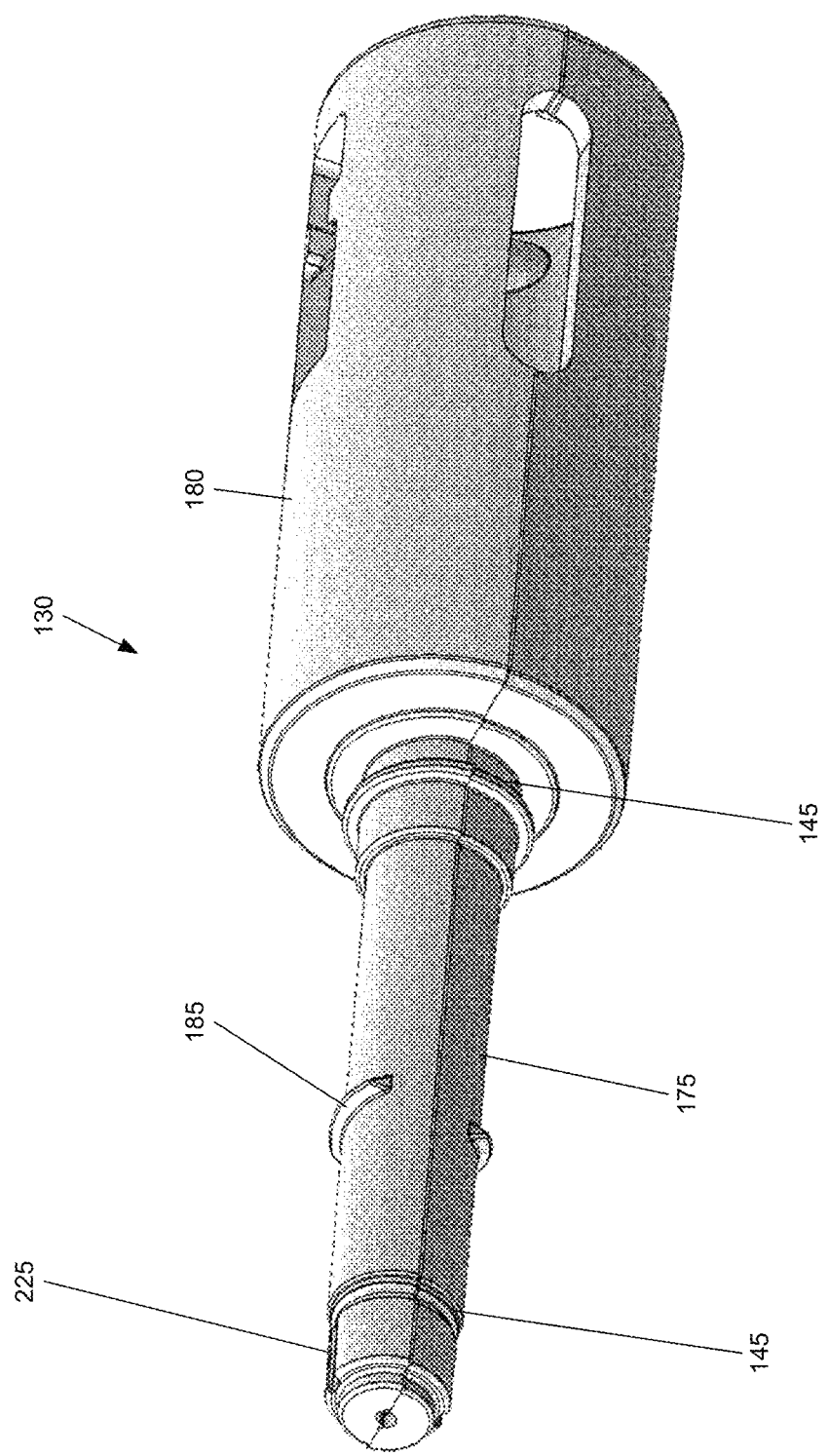
FIG. 6 is an isometric view of a torque portion of the handle.

As depicted in FIG. 6, which is an isometric view of the torque portion 130 of the handle 108, the drive shaft 175 has a generally cylindrical outer surface that is interrupted by flanges and recesses that define circumferential grooves 145 that interface with the interior wall structures 135 of the housing portion 125 to act as rotational bearing surfaces for the drive shaft and prevent distal-proximal displacement of the drive shaft relative to the housing 125. A helical partial thread 185 radially projects from the cylindrical outer surface of the drive shaft 175 near the midpoint of the length of the drive shaft 175. This helical partial tread 185 threadably engages threads 250 on the threaded cylindrical interior or axial shaft 235 of the shuttle 160 as discussed below. The torque portion 130 may be made of materials such as, for example, polymers, metals, and/or etc.

Figure 7A:
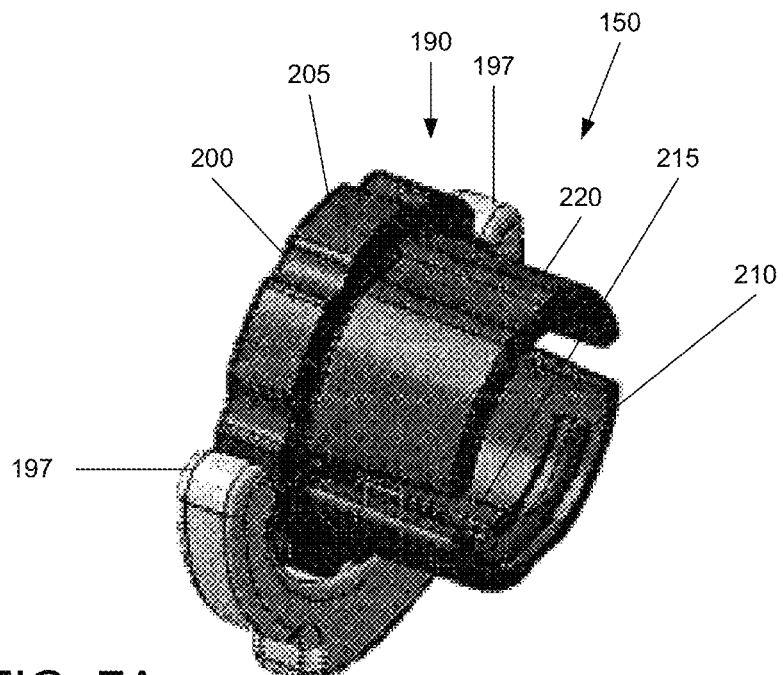
FIGS. 7A and 7B are opposite isometric views of a ratchet assembly of the rotation mechanism.
Figure 7B:
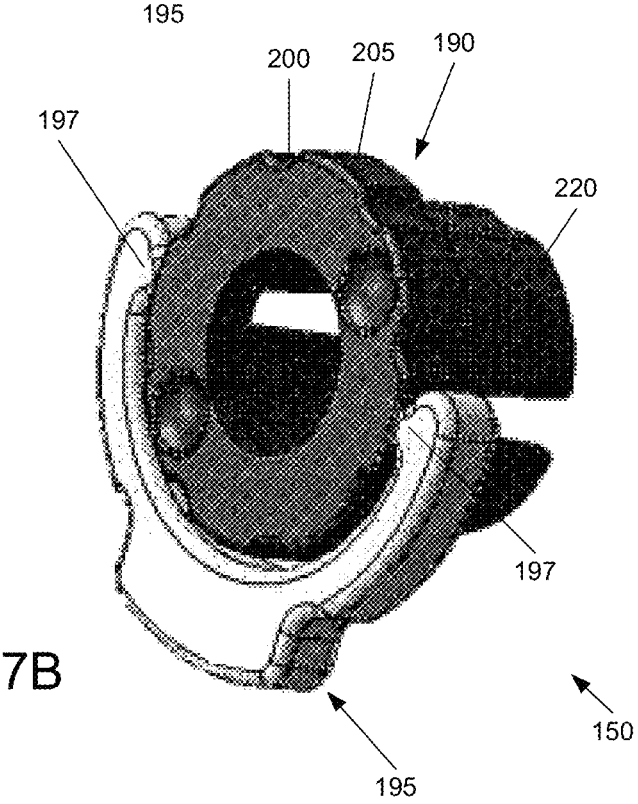

As indicated in FIGS. 7A and 7B, which are opposite isometric views of the ratchet assembly 150 of the rotation mechanism 90, the ratchet assembly 150 includes an inner notched-rim wheel 190 and an outer dual pawl 195 that includes opposed tab arms 197 that engage notches or recesses 200 defined in the outer circumferential surface of a rim 205 of the inner notched-rim wheel 190. A circumferentially extending key ridge 210 and a longitudinally extending key ridge 215 project radially inward from an inner circumferential surface of a cylinder portion 220 of the inner notched-rim wheel 190.

As can be understood from FIGS. 3-7B, the ratchet assembly 150 extends about the circumference of the distal end of the drive shaft 175. The key ridges 210, 215 of the inner notched-rim wheel 190 are received in a mating interference fit with complementary female circumferential and longitudinal slots 145, 225 defined in the drive shaft 175 near its distal end. On account of this arrangement, clockwise or counter-clockwise rotation of the drive shaft 175 rotates the inner notched-rim wheel 190 in the same directions. Rotational displacement of the inner notched-rim wheel 190 causes the recesses 200 to displace against the pawl arms 195, thereby creating a tactile sensation in the grip 180 of the torque portion 130 when the torque portion is rotated relative to the housing 125. The inner notched-rim wheel 190 may be made of materials such as, for example, polymers or etc. The outer dual pawl 195 may be made of materials such as, without limitation, engineering polymers, and/or metals.

Figure 8A:
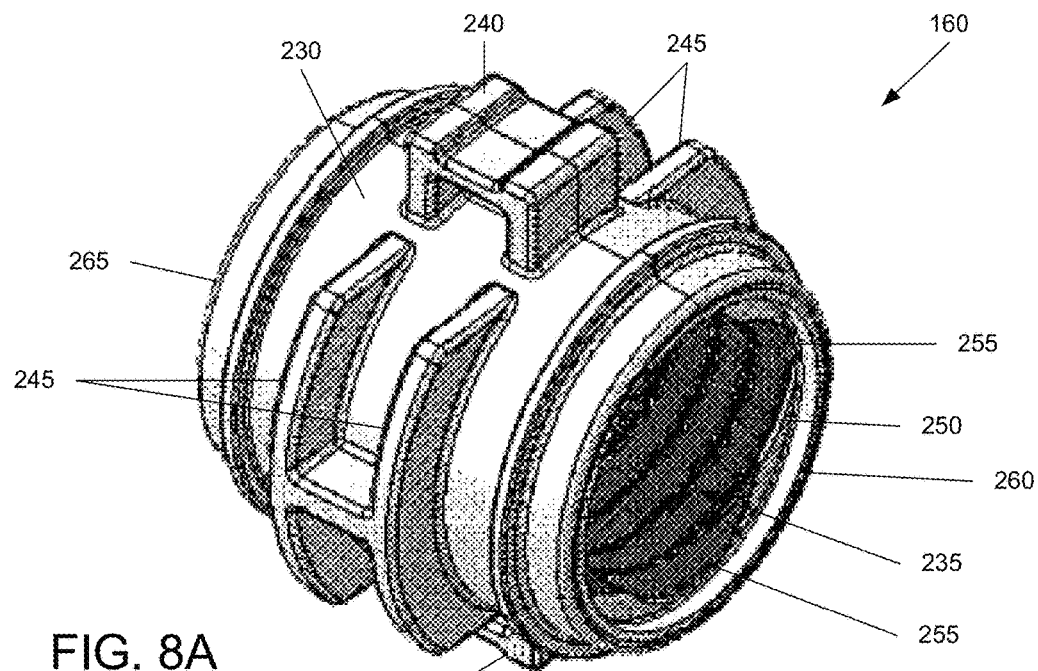
FIGS. 8A and 8B are opposite isometric views of a shuttle of the rotation mechanism.
Figure 8B:
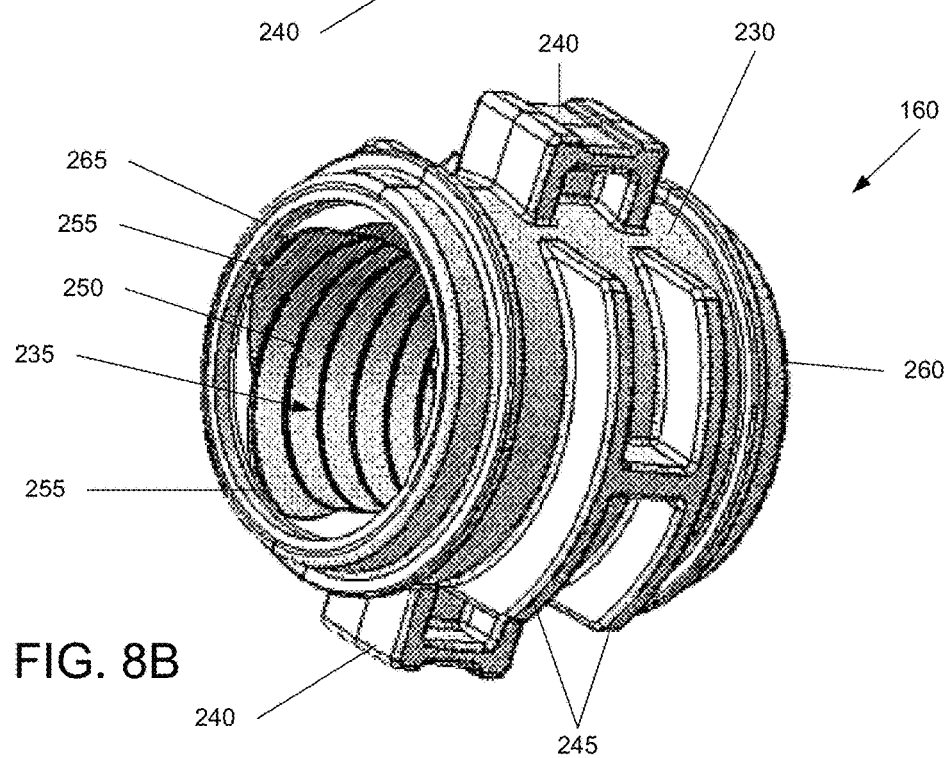

FIGS. 8A and 8B are opposite isometric views of a shuttle 160 of the rotation mechanism 90. As reflected in FIGS. 8A and 8B, the shuttle 160 includes a cylindrical body 230 with a threaded cylindrical axial shaft 235 extending distal-proximal through the body 230, a pair of guide members 240 radially projecting outward from the outer circumferential surface of the body 230 on opposite sides of the body from each other, and pairs of longitudinally spaced apart ribs 245 radially projecting outward from the outer circumferential surface of the body 230 and extending circumferentially about the body. The shuttle 160 may be made of materials such as, without limitation, engineering polymers, and/or metals.

The thread 250 in the threaded cylindrical axial shaft 235 is a multi-start thread with two, three, four or more thread-start locations 255 intersecting the proximal rim 260 and the distal rim 265 of the threaded cylindrical axial shaft 235. These thread-start locations 255 allow the helical partial tread 185 on the drive shaft 175 to enter the thread 250 at multiple locations about the circumference of the proximal and distal rims 260, 265 and threadably engage the thread 250 on the threaded cylindrical interior or axial shaft 235 of the shuttle 160, as can be understood from FIGS. 3-5 and as discussed below.

As can be understood from FIGS. 2-5, the pair of guide members 240 are received in respective longitudinally extending guide slots 270 defined in the exterior wall 140 of the housing 125 such that the guide members 240 linearly displace distal-proximal along the respective guide slots 270 as the drive shaft 175 threadably drives the shuttle 160 distal-proximal along the length of the drive shaft 160 when the drive shaft is rotated clockwise or counter-clockwise. In some embodiments, the guide slots 270 are in the form of windows daylighting through the wall 140 of the housing 125 such that the displacement of the guide members 240 of the shuttle can be visually observed.

Figure 9A:
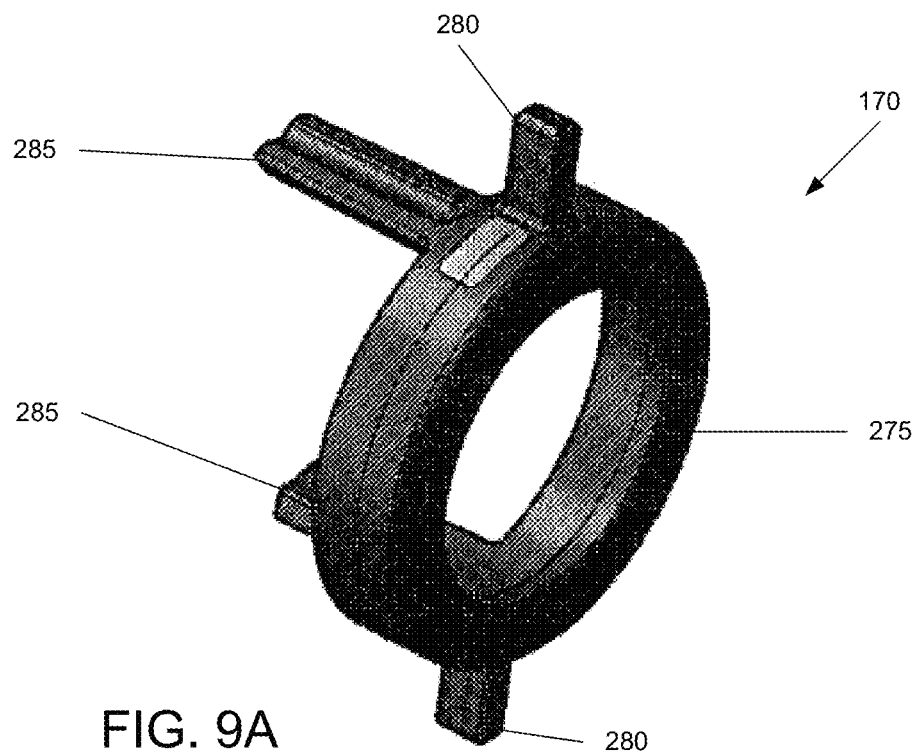
FIGS. 9A and 9B are opposite isometric views of a stop ring of the rotation assembly.
Figure 9B:
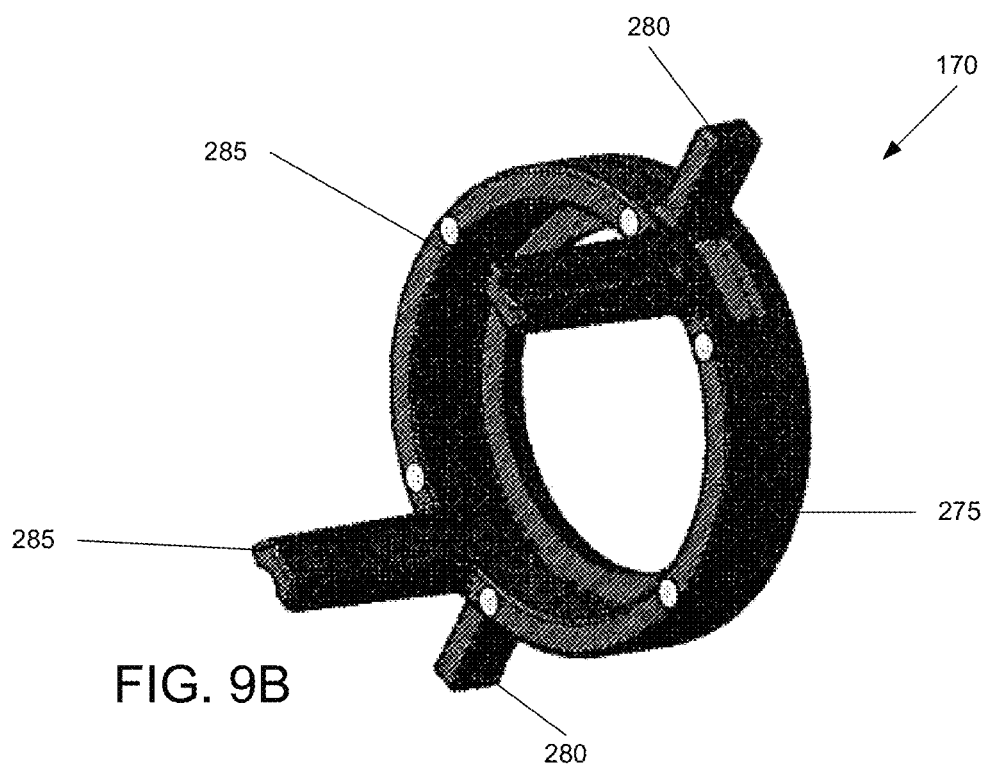
Figure 9C:
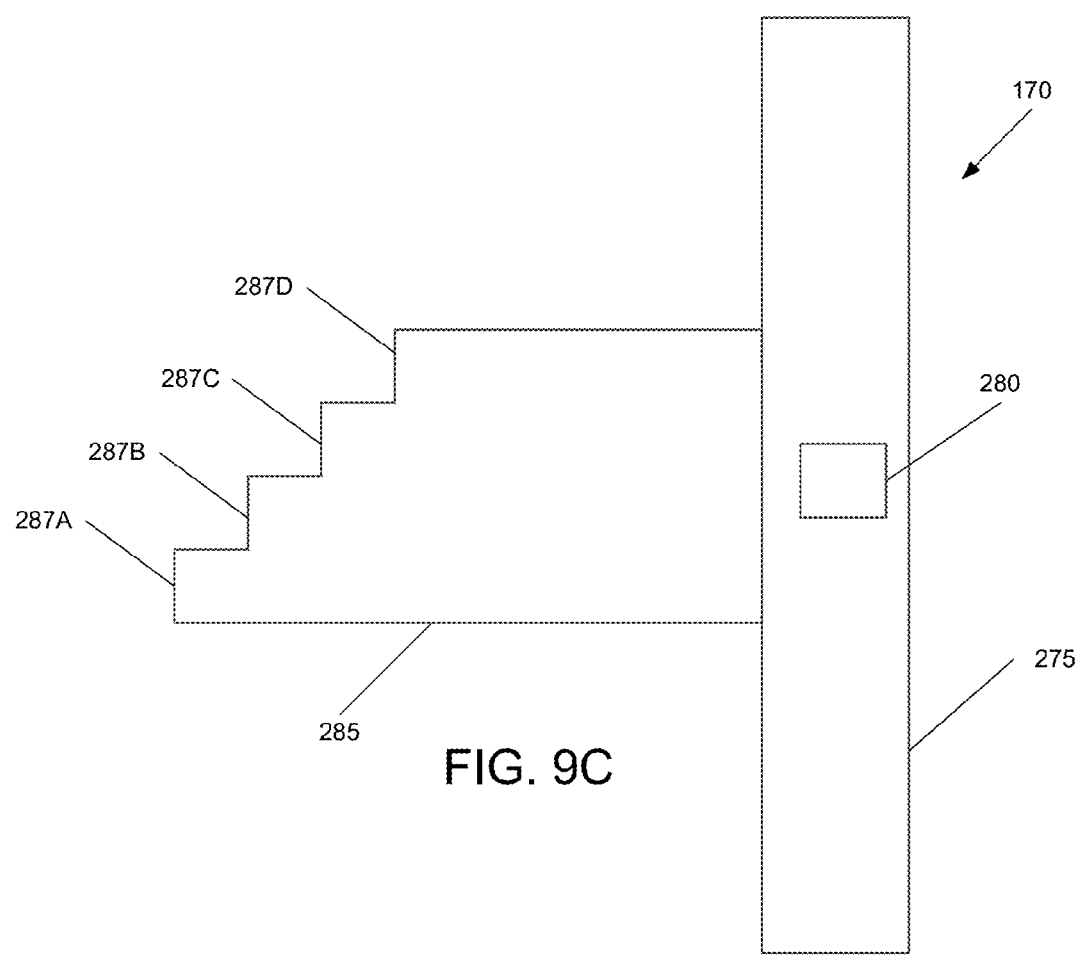
FIG. 9C is a side plan view of a modification to the stop ring of FIGS. 9A and 9B.

FIGS. 9A and 9B are opposite isometric views of a stop ring 170 of the rotation assembly 90. As indicated in FIGS. 9A and 9B, the stop ring 170 includes a ring 275, a pair of lever arms 280 radially outwardly projecting from opposite sides of the ring 275, and a pair of hard stop members 285 distally projecting from a distal edge of the ring 275 and at opposite locations on the ring 275. The stop ring 170 may be made of materials such as, for example, polymers, metals, and/or etc.

As illustrated in FIGS. 2, 3 and 5, the stop ring 170 extends around the proximal region of the drive shaft 175, the hard stop members 285 extending distally along the drive shaft and generally parallel to the drive shaft 175. The lever arms 280 radially project outwardly through a respective pair of circumferentially extending window slots 290 defined in the exterior wall 140 of the housing 125.

As can be understood from FIGS. 3, 5, 7A, 7B, 8A and 8B, the distal spring 155 is located between the proximal face of the rim 205 of the inner notched-rim wheel 190 and the distal faces of the guide members 240 and the distal pair of ribs 245 of the shuttle 160. When the shuttle 160 is fully distally displaced along the length of the drive shaft 175, as depicted in FIGS. 3, 5, 10A and 10B, the distal spring 155 extends around the outer cylindrical surface of the cylinder portion 220 of the inner notched-rim wheel 190, the outer cylindrical surface of the drive shaft 175, and the outer cylindrical surface of the shuttle body 230 distal the guide members 240.

As can be understood from FIGS. 3, 5, 7A, 7B, 8A and 8B, the proximal spring 165 is located between the distal face of the ring 275 of the stop ring 170 and the proximal faces of the guide members 240 and the proximal pair of ribs 245 of the shuttle 160. When the shuttle 160 is fully proximally displaced along the length of the drive shaft 175, as depicted in FIGS. 11A and 11B, the proximal spring 165 extends around the outer cylindrical surface of the drive shaft 175 and the outer cylindrical surface of the shuttle body 230 proximal the guide members 240. The proximal spring 165 will also be located radially inward of the hard stop members 285.

The springs 155, 165 may be made of materials such as, for example, metals, compressible polymers, and/or etc. While depicted as being helical springs in the various FIGS. herein, in other embodiments, the springs 155, 165 may have other configurations such as, for example, elastomeric polymers, or may even be replaced with other biasing members such as, for example, bands that stretch and create tension on the shuttle.

As can be understood from FIGS. 3 and 5, in some embodiments, the distal and proximal springs 155, 165 may abut against the respective proximal and distal faces of the guide members 240 and ribs 245. In other embodiments, as indicated in FIGS. 10A-11B, rings 295 extend about the outer cylindrical surfaces of the shuttle body 230 proximal and distal the guide members 240 and ribs 245. These rings 295 may be formed of materials such as, without limitation, engineering polymers, and/or metals and will contact the respective springs 155, 165.

FIG. 10A is an isometric view of the handle 108 with a portion of a housing 125 removed to reveal the rotation mechanism 90 enclosed therein, the shuttle 160 being in a most distal location along a shaft 175 of the torque portion 130 of the handle. FIG. 10B is a longitudinal cross-section of the rotation mechanism 90 in the region identified in FIG. 10A and as taken along section line 10B-10B in FIG. 10A.

As illustrated in FIGS. 10A and 10B, when the shuttle 160 is in the most distal location along the shaft 175 of the torque portion 130 of the handle 108, the distal spring 155 is compressed between the distal ring 295 of the shuttle 160 and an interior wall 135 immediately proximal the ratchet assembly 150. As can be understood from FIG. 10A, on account of the pitch direction of the helical partial thread 185 on the shaft 175 of the torque portion 130, and despite the distal spring 155 biasing the shuttle proximally such that its distal rim 265 (see FIGS. 8A and 8B) is kept in abutting contact with the thread 185, the thread 185 of the shaft 175 does not engage the interior threads 250 of the shuttle 160 as long as the torque portion 130 is rotated counter-clockwise (CCW), the thread 185 simply riding along the distal rim 265 of the shuttle 160. Thus, the torque portion 130 and the linear member 120 extending distally therefrom, as shown in FIG. 3, can infinitely rotate CCW and cause the leadless pacemaker 102 to rotate CCW, as can be understood from FIG. 1, such that the helical anchor on the distal end of the leadless pacemaker will unscrew from cardiac tissue in which it may be imbedded. The CCW rotation causes the ratchet assembly 150 to generate an incremental/stepped tactile sensation in the grip 180 of the torque portion 130 of the handle 108.

Conversely and as can be understood from FIG. 10A, on account of the pitch direction of the helical partial thread 185 on the shaft 175 of the torque portion 130, and because the distal spring 155 biases the shuttle proximally such that its proximal rim 265 is kept in abutting contact with the thread 185, the thread 185 of the shaft 175 engages the interior threads 250 of the shuttle 160 once the torque portion 130 is rotated clockwise (CW) and the shaft thread 185 encounters one of the multiple thread-start locations 255 intersecting the proximal rim 265. Once threaded engagement occurs between the shaft thread 185 and the shuttle threads 250, further CW rotation of the torque portion 130 will cause the shuttle 160 to proximally displace along the shaft 175. As can be understood from FIGS. 1 and 3, the CW rotation of the torque portion 130 and the linear member 120 extending distally therefrom rotates the leadless pacemaker 102 CW such that the helical anchor on the distal end of the leadless pacemaker will screw into cardiac tissue contacting the helical anchor. The CW rotation causes the ratchet assembly 150 to generate an incremental/stepped tactile sensation in the grip 180 of the torque portion 130 of the handle 108.

Continued CW rotation of the torque potion 130 further proximally displaces the shuttle 160 along the shaft 175 as the shuttle threads 250 move proximally along the rotating shaft thread 185, which is confined to rotation about the longitudinal axis of the shaft and does not displace distal-proximal. As the shuttle moves along the shaft, the shuttle guide members 240 linearly displace proximally along the respective guide slots 270, and this displacement can be observed through the windows created by the guide slots 270 in the exterior wall 140 of the housing 125, as can be understood from FIGS. 2, 4 and 5.

As the CW rotation of the torque portion 130 causes the shuttle 160 to displace proximally from the most distal location, as depicted in FIGS. 10A and 10B, the tactile sensation and resistance felt in the grip 180 of the torque portion 130 will remain constant as provided by the ratchet assembly 150 until the shuttle 160 is sufficiently proximally displaced such that the proximal faces of the shuttle guide members 240 come into abutting contact with the distal tip faces of the hard stop members 285 of the stop ring 170, as illustrated in FIGS. 11A and 11B. In some embodiments, the rotational resistance may increase slightly as the proximal spring 165 is initially contacted by the shuttle proximal ring 295 immediately prior to the abutting contact between the shuttle guide members 240 and the hard stop members 285, thereby placing the proximal spring 165 in the initial stages of compression between the shuttle proximal ring 295 and the distal face of the ring 275 of the stop ring 170.

In one embodiment, the number of CW rotations needed to displace the shuttle from the most distal position depicted in FIGS. 10A and 10B to the stopped position shown in FIGS. 11A and 11B will be two and one-quarter rotations of the grip 180 of the torque portion 130 of the handle 108. This two and one-quarter rotations is based on what is considered to be a typical number of turns of the helical anchor of the leadless pacemaker to cause the helical anchor to fully imbed in the cardiac tissue without over-penetrating the cardiac tissue. In other embodiments, the number of rotations required to displace the shuttle between the locations depicted in FIGS. 10A-10B and 11A-11B will be more or less than two and one-quarter rotations.

Once the proximal faces of the shuttle guide members 240 come into abutting contact with the distal tip faces of the hard stop members 285 of the stop ring 170, as illustrated in FIGS. 11A and 11B, this contact will notify the physician that the prescribed number of rotations of the helical anchor of the leadless pacemaker has been reached. At this point, should the physician decide additional CW rotations of the helical anchor of the leadless pacemaker are necessary to achieve a desired level of fixation to the cardiac tissue, as illustrated in FIGS. 12A and 12B, the lever arms 280 of the stop ring 170 may be rotated about the longitudinal axis of the shaft 175 to cause the hard stop members 285 to move out of the way of the shuttle guide members 240 such that continued CW rotations of the grip 180 of the torque portion 130 of the handle 108 will continue to proximally displace the shuttle 160.

As indicated in FIGS. 12A and 12B, sufficient CW rotations of the grip 180 of the torque portion 130 of the handle 108 will cause the shuttle 160 to fully compress the proximal spring 165 and the shuttle 160 to move proximally past the shaft thread 185 such that the shaft thread 185 no longer is in threaded engagement with the shuttle threads 250 but is distal the shuttle threads 250. At this point, the grip 180 of the torque portion 130 of the handle 108 can be rotated infinitely CW as the shaft thread 185 simply rides along the proximal edge 260 of the shuttle 160 on account of the pitch direction of the shaft helical partial thread 185. Thus, the torque portion 130 and the linear member 120 extending distally therefrom, as shown in FIG. 3, can infinitely rotate CW and cause the leadless pacemaker 102 to rotate CW, as can be understood from FIG. 1, such that the helical anchor on the distal end of the leadless pacemaker will screw into cardiac tissue for fixation thereto.

Conversely and as can be understood from FIG. 12B, on account of the pitch direction of the helical partial thread 185 on the shaft 175 of the torque portion 130, and because the proximal spring 165 biases the shuttle distally such that its distal proximal rim 260 is kept in abutting contact with the thread 185, the thread 185 of the shaft 175 engages the interior threads 250 of the shuttle 160 once the torque portion 130 is rotated counter-clockwise (CCW) and the shaft thread 185 encounters one of the multiple thread-start locations 255 intersecting the distal rim 260. Once threaded engagement occurs between the shaft thread 185 and the shuttle threads 250, further CCW rotation of the torque portion 130 will cause the shuttle 160 to distally displace along the shaft 175. This distal displacement of the shuttle will continue until it reaches the most distal location on the shaft, as indicated in FIGS. 10A and 10B, or the grip 180 of the torque portion 130 is again rotated CW. In either case, the CCW rotation of the grip 180 will bring about CCW rotation of the helical anchor for unscrewing from cardiac tissue, and CW rotation of the grip 180 will bring about CW rotation of the helical anchor for screwing into cardiac tissue.

In the event the grip 180 is again rotated CW to bring about screwing of the helical anchor into the cardiac tissue, to again allow for the advantages of the rotation limit warning afforded by the stop ring 170, the stop ring 170 can be reset (rotated) such that its hard stop members 285 are again aligned with the shuttle guide members 240 to come into abutting contact with the distal tip faces of the of the stop ring 170, as can be understood from FIGS. 10A-11B.

The warning aspect of the rotation mechanism 90 of FIGS. 2-12B could be adapted to provide multiple warnings to the physician when a certain number of rotations of the leadless pacemaker has occurred. For instance, as illustrated in FIG. 9C, which is a side plan view of a modification to the stop ring 170 of FIGS. 9A and 9B, a warning could be provided every full rotation of the torque portion 130 of the handle 108 to alert the physician of another complete rotation of the leadless pacemaker. This could be achieved, for example, by providing hard stop members 285 that have a stepped configuration with a series of steps 287A-D that are radially offset from each other and increasingly proximally located. Each step 287A-D provides an increasingly proximal point of contact with the shuttle guide members 240. Thus, once the shuttle guide members 240 have contacted a first pair of steps 287A of the hard stop members 285 and the physician desires to make an additional rotation of the leadless pacemaker, the stop ring 170 can be incrementally rotated to align the shuttle guide members 240 with the next radially adjacent pair of steps 287B, this next radially adjacent pair of steps 287B being located more proximally than the initially contacted pair of steps 287A. The physician can then rotate the leadless pacemaker a full turn before contacting the second pair of steps 287B. The process can then be repeated for successive contacts with the rest of the steps 287C and 287D for two more purposeful and incremental rotations of the leadless pacemaker.

The warning mechanism afforded by the embodiment of FIGS. 2-12B provides a hard stop at a certain rotation level in the torque portion of the handle. It eliminates any chance of the physician by-passing a more passive indicator by requiring an extra motion to continue rotating, guaranteeing that the physician will notice the warning by completely preventing further rotations until actively addressing the hard stop. Specifically, it requires another user action in order to continue rotating the torque portion of the handle and, by extension, the leadless pacemaker. A visual indicator on the outside of the handle presents that the warning system has been contacted.

C. Handle with Rotation Mechanism Employing O-Ring Rotation Limit Warning

Figure 13:
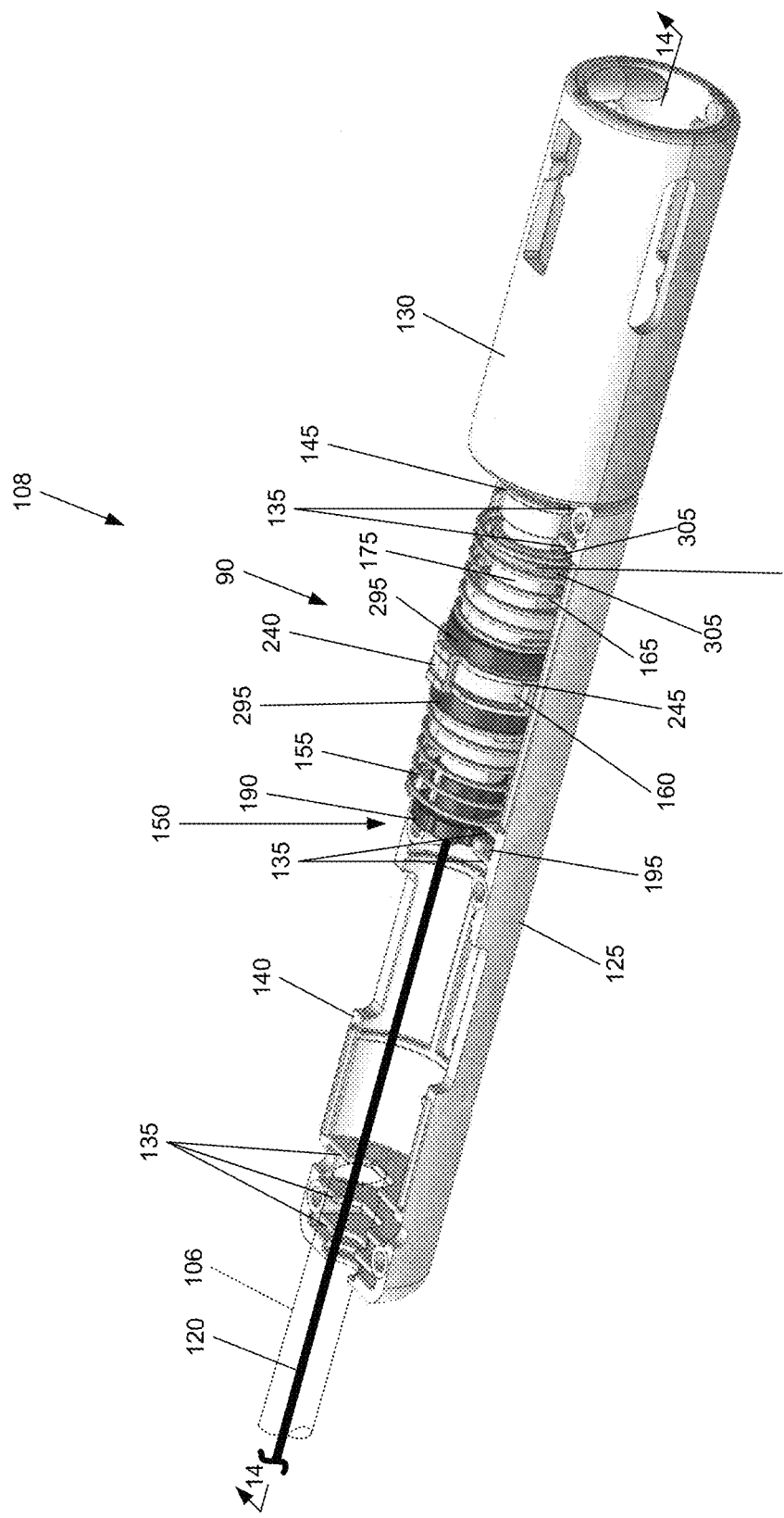
FIG. 13 is an isometric view of the handle of the leadless pacemaker delivery system, except employing another version of the rotation mechanism disclosed herein, wherein a portion of a housing of the handle is removed to reveal the rotation mechanism enclosed therein.
Figure 14:
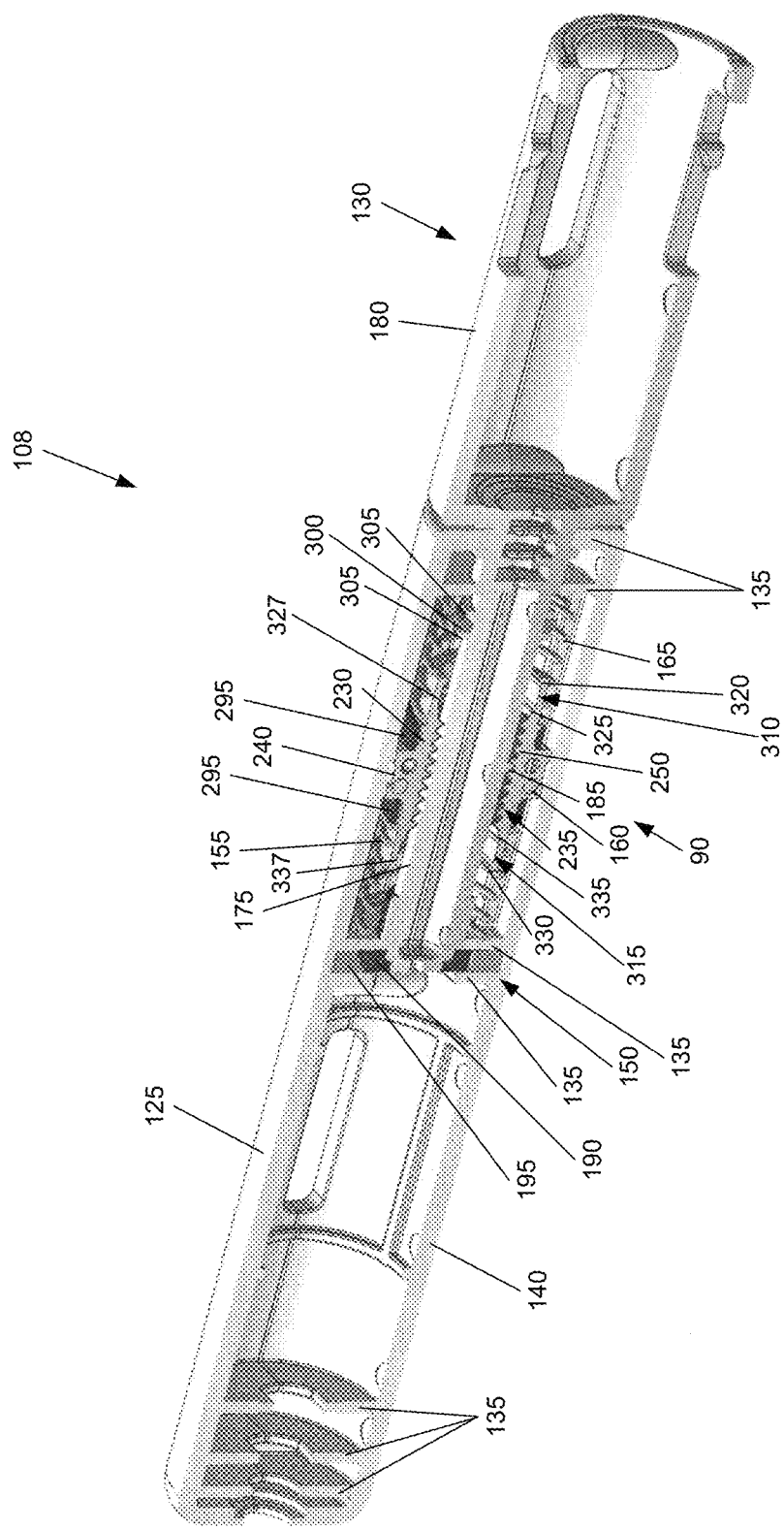
FIG. 14 is a longitudinal cross section of the handle and rotation mechanism enclosed therein as viewed along section line 14-14 in FIG. 14.
Figure 15:
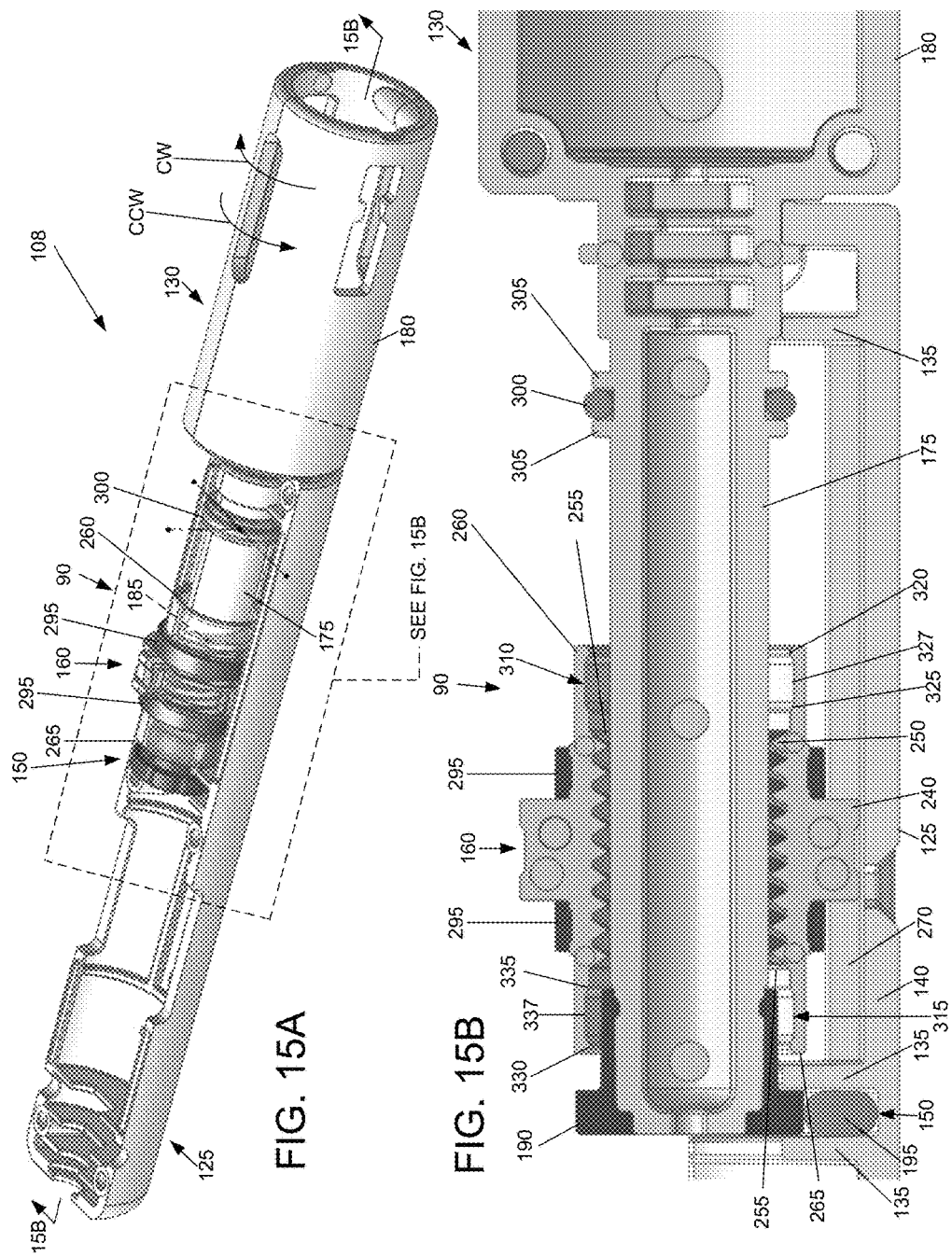
FIG. 15A is an isometric view of the handle with a portion of a housing removed to reveal the rotation mechanism enclosed therein, the shuttle being in a most distal location along a shaft of the torque portion of the handle and the springs being hidden for clarity purposes.
FIG. 15B is a longitudinal cross-section of the rotation mechanism in the region identified in FIG. 15A and as taken along section line 15B-15B in FIG. 15A.

To begin a discussion of another embodiment of the rotation mechanism 90 of the handle 108 of the leadless pacemaker delivery system of FIG. 1, reference is now made to FIGS. 13 and 14. FIG. 13 is an isometric view of the handle 108 with a portion of a housing 125 of the handle 108 removed to reveal the alternative rotation mechanism 90 enclosed therein, and FIG. 14 is a longitudinal cross section of the handle 108 and alternative rotation mechanism 90 enclosed therein as viewed along section line 13-13 in FIG. 13.

As can be understood from a comparison of FIGS. 13 and 14 to FIGS. 3-5, the alternative version of the rotation mechanism 90 and the surrounding elements of the handle 108 and leadless pacemaker delivery system of the version of FIGS. 13 and 14 share the majority of elements and operation as discussed above with respect to FIGS. 1-12B, except an O-ring 300 has replaced the stop ring 170 and the shuttle 160 employs features that interact with the O-ring 300. Accordingly, the preceding discussion of FIGS. 1-12B is equally applicable to the version of the rotation mechanism 90 and surrounding elements of the handle 108 shown in FIGS. 13 and 14, except as will now be specifically discussed with respect to FIGS. 13-18B.

As indicated in FIGS. 13 and 14, the O-ring 300 extends circumferentially around, and is coaxial with, the shaft 175 of the torque portion 130. Also, the O-ring 300 is sandwiched between parallel and spaced-apart flange rings 305 of the shaft 175 and extend radially outwardly from the outer circumference of the shaft 175. The O-ring 300 and flange rings 305 are located near the proximal end of the shaft 175 of the torque portion 130. The O-ring 300 may be made of materials such as, for example, elastomeric polymer and have a durometer of between approximately 10 and approximately 100 Shore A. The O-ring 300, which is compressible, may have a circular transverse cross-section as shown in FIG. 15B. Alternatively, the O-ring 300 may have a transverse cross-section that is oval, square, rectangular, or etc.

As shown in FIG. 14, the shuttle 160 includes a proximal inner circumferential chamber 310 at the proximal end of the shuttle and a distal inner circumferential chamber 315 at the distal end of the shuttle. Each chamber 310, 315 includes a pair of spaced-apart radially inwardly extending lips, these lips being an outer lip and an inner lip. Specifically, for the proximal chamber 310, the outer lip is a proximal outer lip 320 at the proximal edge of the shuttle 160, and the inner lip is a distal inner lip 325 distal the proximal outer lip 320. The lips 320, 325 are spaced-apart from each other and radially inwardly project from an inner cylindrical surface 327 of the proximal chamber 310. For the distal chamber 315, the outer lip is a distal outer lip 330 at the distal edge of the shuttle 160, and the inner lip is a proximal inner lip 335 proximal the distal outer lip 330. The lips 330, 335 are spaced-apart from each other and radially inwardly project from an inner cylindrical surface 337 of the distal chamber 315.

FIG. 15A is an isometric view of the handle 108 with a portion of a housing 125 removed to reveal the rotation mechanism 90 enclosed therein, the shuttle 160 being in a most distal location along a shaft 175 of the torque portion 130 of the handle and the springs 155, 165 being hidden for clarity purposes. FIG. 15B is a longitudinal cross-section of the rotation mechanism 90 in the region identified in FIG. 15A and as taken along section line 15B-15B in FIG. 15A.

As illustrated in FIGS. 15A and 15B, when the shuttle 160 is in the most distal location along the shaft 175 of the torque portion 130 of the handle 108, the distal spring 155 (shown in FIGS. 13 and 14) is compressed between the distal ring 295 of the shuttle 160 and an interior wall 135 immediately proximal the ratchet assembly 150. As can be understood from FIG. 15A, on account of the pitch direction of the helical partial thread 185 on the shaft 175 of the torque portion 130, and despite the distal spring 155 biasing the shuttle proximally such that its distal rim 265 is kept in abutting contact with the thread 185, the thread 185 of the shaft 175 does not engage the interior threads 250 of the shuttle 160 as long as the torque portion 130 is rotated counter-clockwise (CCW), the thread 185 simply riding along the distal rim 265 of the shuttle 160. Thus, the torque portion 130 and the linear member 120 extending distally therefrom, as shown in FIG. 13, can infinitely rotate CCW and cause the leadless pacemaker 102 to rotate CCW, as can be understood from FIG. 1, such that the helical anchor on the distal end of the leadless pacemaker will unscrew from cardiac tissue in which it may be imbedded. The CCW rotation causes the ratchet assembly 150 to generate an incremental/stepped tactile sensation in the grip 180 of the torque portion 130 of the handle 108.

Conversely and as can be understood from FIG. 15A, on account of the pitch direction of the helical partial thread 185 on the shaft 175 of the torque portion 130, and because the distal spring 155 (shown in FIGS. 13 and 14) biases the shuttle proximally such that its proximal rim 265 is kept in abutting contact with the thread 185, the thread 185 of the shaft 175 engages the interior threads 250 of the shuttle 160 once the torque portion 130 is rotated clockwise (CW) and the shaft thread 185 encounters one of the multiple thread-start locations 255 intersecting the proximal rim 265. Once threaded engagement occurs between the shaft thread 185 and the shuttle threads 250, further CW rotation of the torque portion 130 will cause the shuttle 160 to proximally displace along the shaft 175. As can be understood from FIGS. 1 and 13, the CW rotation of the torque portion 130 and the linear member 120 extending distally therefrom rotates the leadless pacemaker 102 CW such that the helical anchor on the distal end of the leadless pacemaker will screw into cardiac tissue contacting the helical anchor. The CW rotation causes the ratchet assembly 150 to generate an incremental/stepped tactile sensation in the grip 180 of the torque portion 130 of the handle 108.

Continued CW rotation of the torque potion 130 further proximally displaces the shuttle 160 along the shaft 175 as the shuttle threads 250 move proximally along the rotating shaft thread 185, which is confined to rotation about the longitudinal axis of the shaft and does not displace distal-proximal. As the shuttle moves along the shaft, the shuttle guide members 240 linearly displace proximally along the respective guide slots 270. In some embodiments where the guide slots 270 daylight through the exterior wall 140 of the housing 125, the displacement of the shuttle guide members 240 can be observed through the windows created by the guide slots 270 in the exterior wall 140 of the housing 125, similar to that discussed above with respect to FIGS. 2, 4 and 5.

As the CW rotation of the torque portion 130 causes the shuttle 160 to displace proximally from the most distal location, as depicted in FIGS. 15A and 15B, the tactile sensation and resistance felt in the grip 180 of the torque portion 130 will remain constant as provided by the ratchet assembly 150 until the shuttle 160 is sufficiently proximally displaced such that the proximal boundary of the proximal outer lip 320, which is at the shuttle proximal edge 260, encounters the distal boundary of the O-ring 300, as illustrated in FIGS. 16A and 16B. At this time, the resistance felt in the grip 180 of the torque portion 130 will begin to gradually increase as the radially inwardly projecting lip 320 begins to compress the O-ring 300 as the lip 320 is caused to increasingly move proximally over the O-ring 300. In some embodiments, the rotational resistance may also increase slightly as the proximal spring 165 (shown in FIGS. 13 and 14) is initially contacted by the shuttle proximal ring 295 immediately prior to the radially inwardly projecting lip 320 begins to encounter and radially inwardly compress the O-ring 300, thereby placing the proximal spring 165 in the initial stages of compression between the shuttle proximal ring 295 and an interior wall 135 of the housing 125.

In some embodiments, the shuttle may be able to expand to clear the O-ring or a similar structural impediment to the proximal displacement of the shuttle along the shaft. This expansion capability of the shuttle may be in place of the O-ring compressing or in addition to the O-ring compressing.

In one embodiment, the number of CW rotations needed to displace the shuttle from the most distal position depicted in FIGS. 15A and 15B to the stopped position shown in FIGS. 16A and 16B will be two and one-quarter rotations of the grip 180 of the torque portion 130 of the handle 108. This two and one-quarter rotations is based on what is considered to be a typical number of turns of the helical anchor of the leadless pacemaker to cause the helical anchor to fully imbed in the cardiac tissue without over-penetrating the cardiac tissue. In other embodiments, the number of rotations required to displace the shuttle between the locations depicted in FIGS. 15A-15B and 16A-16B will be more or less than two and one-quarter rotations.

Figure 16:
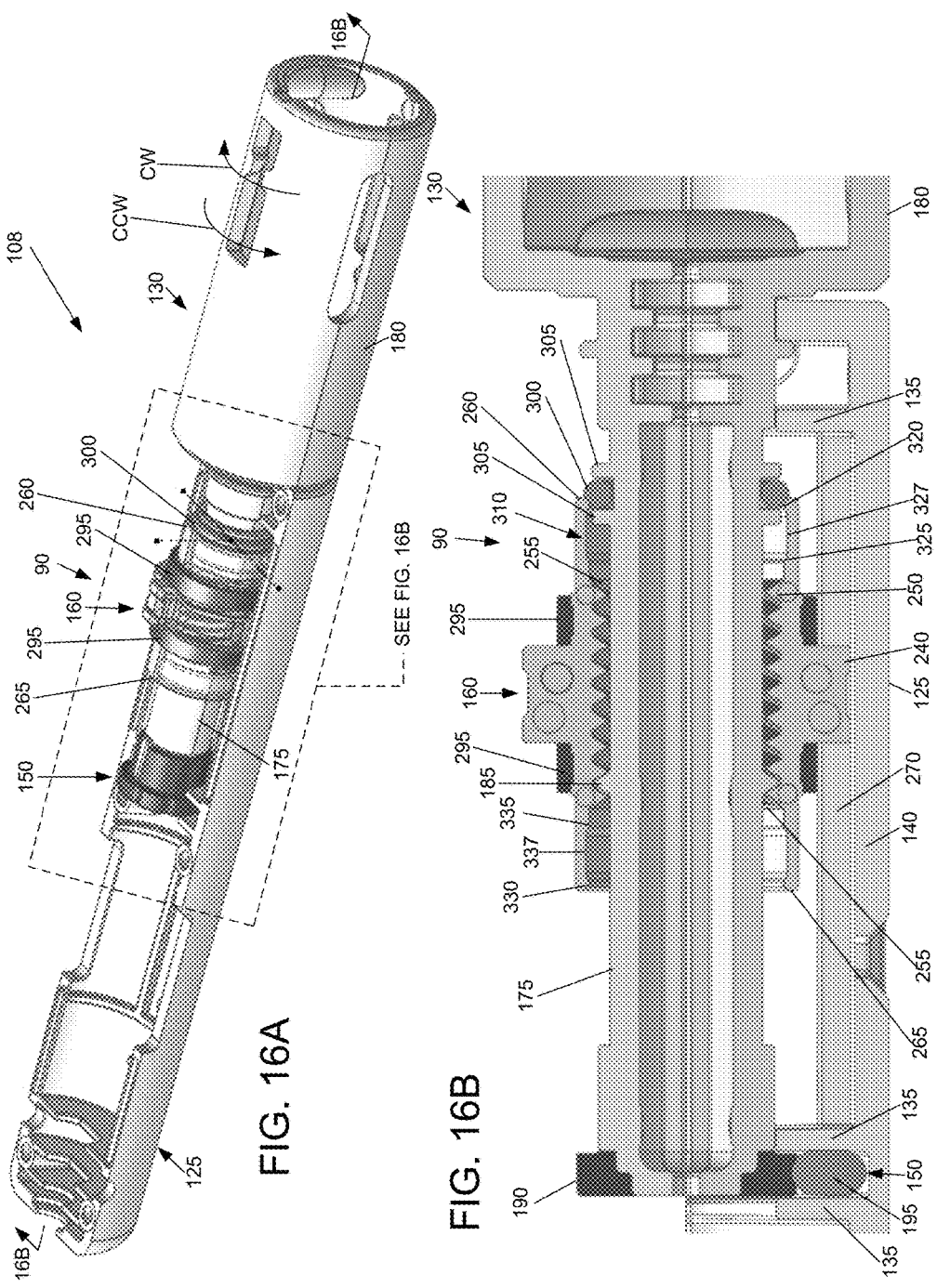
FIG. 16A is the same view as FIG. 15A, except the shuttle is in a proximal location along the shaft of the torque portion of the handle and a proximal lip of a proximal chamber of the shuttle has just began to contact a distal boundary of the O-ring.
FIG. 16B is a longitudinal cross-section of the rotation mechanism in the region identified in FIG. 16A and as taken along section line 16B-16B in FIG. 16A.
Figure 17:
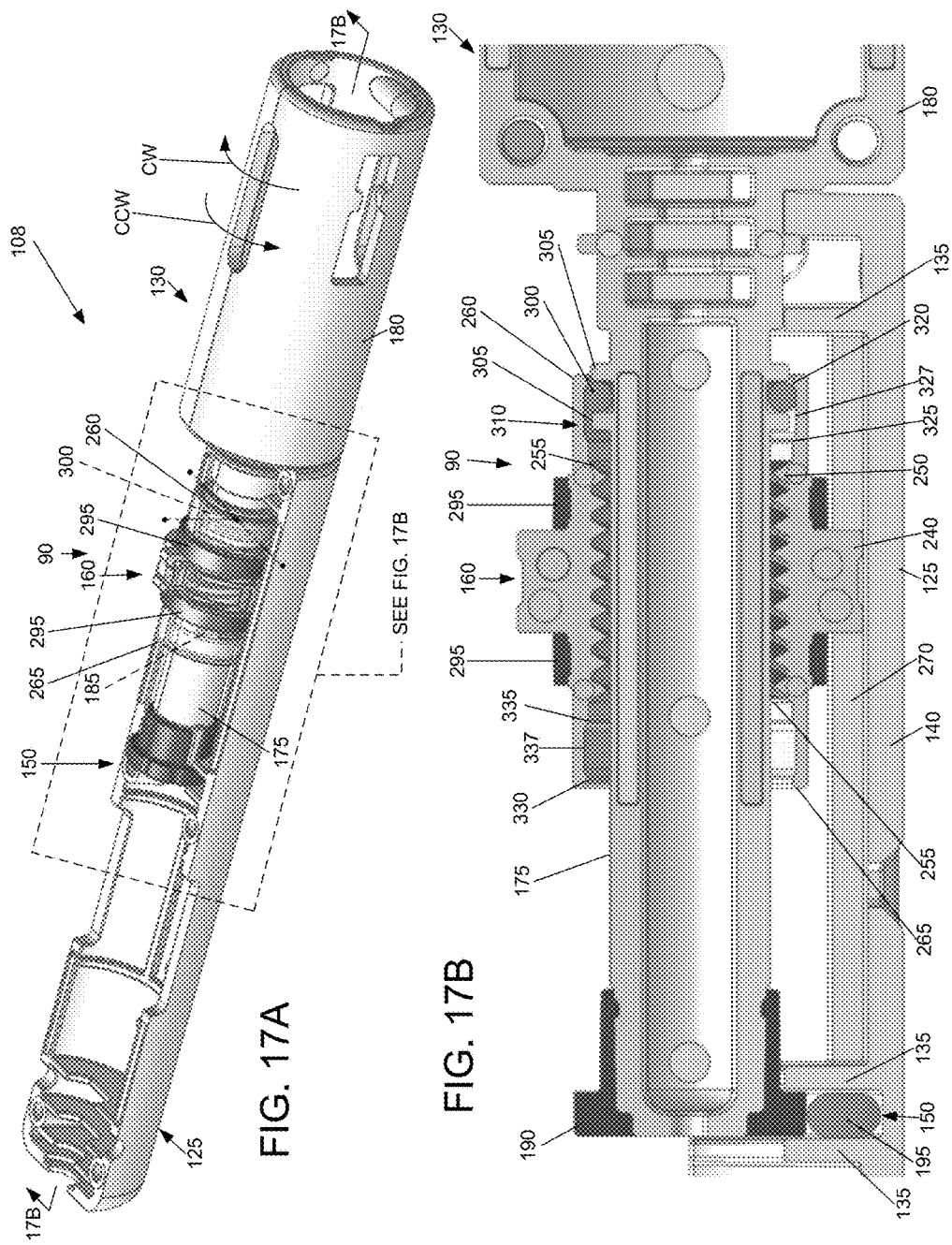
FIG. 17A is the same view as FIG. 16A, except the O-ring has cleared the proximal lip of the proximal chamber of the shuttle and been fully received in the most proximal region of the proximal chamber of the shuttle.
FIG. 17B is a longitudinal cross-section of the rotation mechanism in the region identified in FIG. 17A and as taken along section line 17B-17B in FIG. 17A.
Figure 18:
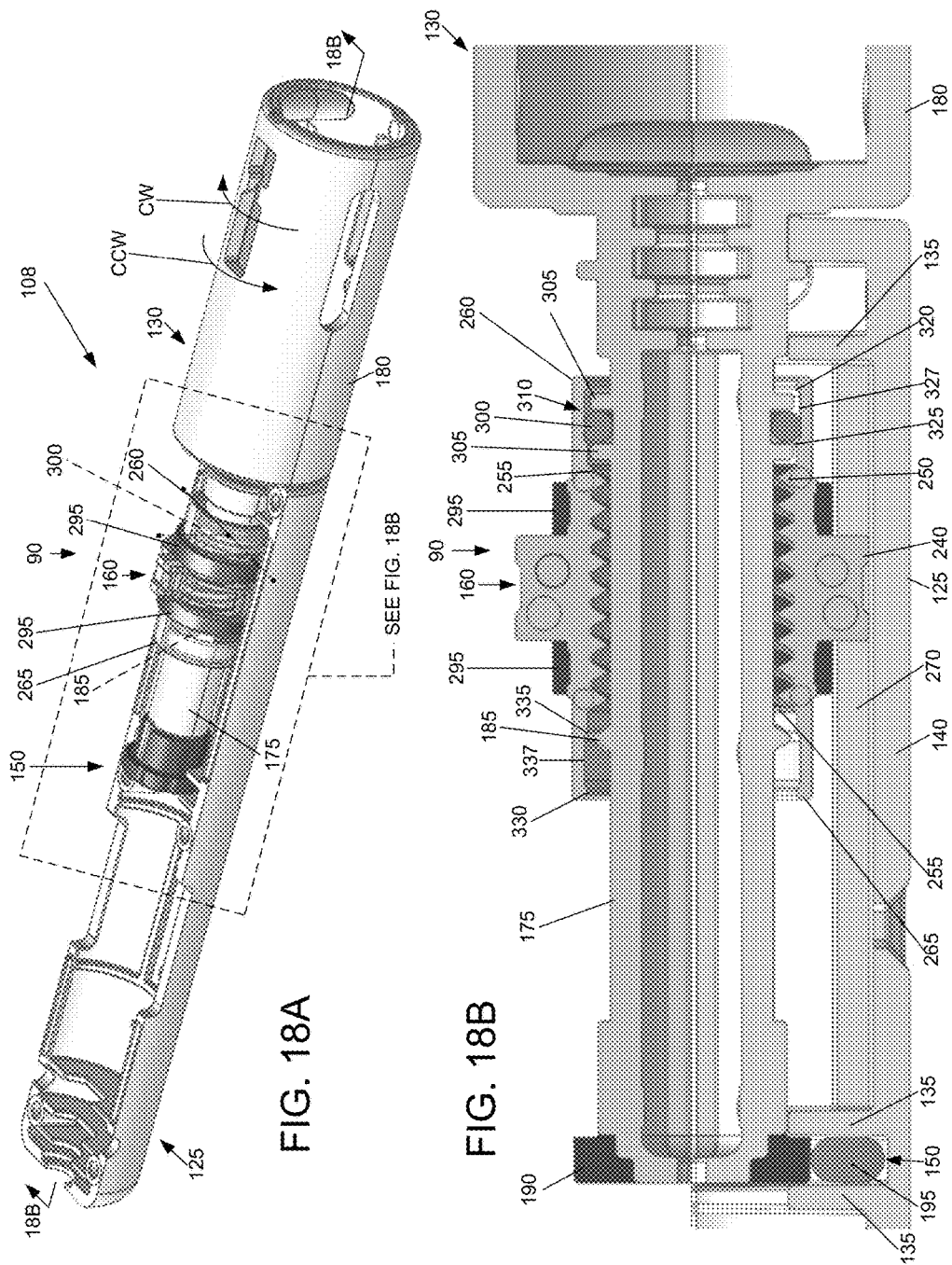
FIG. 18A is the same view as FIG. 17A, except the shuttle is in a most proximal location along the shaft of the torque portion of the handle, the O-ring having been fully received in the most distal region of the proximal chamber of the shuttle, the O-ring abutting against the distal lip of the chamber.
FIG. 18B is a longitudinal cross-section of the rotation mechanism in the region identified in FIG. 18A and as taken along section line 18B-18B in FIG. 18A.

Once the proximal boundary of the proximal outer lip 320, which is at the shuttle proximal edge 260, encounters the distal boundary of the O-ring 300, as illustrated in FIGS. 16A and 16B, this contact will notify the physician that the prescribed number of rotations of the helical anchor of the leadless pacemaker has been reached. At this point, should the physician decide additional CW rotations of the helical anchor of the leadless pacemaker are necessary to achieve a desired level of fixation to the cardiac tissue, as can be understood from FIGS. 16A-17B, continued CW rotations of the grip 180 of the torque portion 130 of the handle 108 will continue to proximally displace the shuttle 160 and drive the radially inwardly projecting lip 320 at the shuttle proximal edge 260 completely over and proximally past the O-ring 300 such that the O-ring 300 is received in the proximal inner circumferential chamber 310 as indicated in FIGS. 17A and 17B.

Since the O-ring 300 is confined distally and proximally by flange rings 305 of the shaft 175, when the lip 320 is caused to pass over the O-ring 300, the O-ring is compressed such that it is deflected into an elliptical cross-section from its self-biasing, or non-deflected, circular cross-section. This change in cross-section of the O-ring 300 increases resistance to the rotation of the torque portion 130 of the handle 108, thereby notifying the physician that the prescribed number of rotations of the helical anchor of the leadless pacemaker has been reached.

As indicated in FIGS. 18A and 18B, sufficient CW rotations of the grip 180 of the torque portion 130 of the handle 108 will cause the shuttle 160 to fully compress the proximal spring 165 (shown in FIGS. 13 and 14) and the shuttle 160 to move proximally past the shaft thread 185 such that the shaft thread 185 no longer is in threaded engagement with the shuttle threads 250 but is distal the shuttle threads 250. At this point, the grip 180 of the torque portion 130 of the handle 108 can be rotated infinitely CW as the shaft thread 185 simply rides along the proximal edge 260 of the shuttle 160 on account of the pitch direction of the shaft helical partial thread 185. Thus, the torque portion 130 and the linear member 120 extending distally therefrom, as shown in FIG. 13, can infinitely rotate CW and cause the leadless pacemaker 102 to rotate CW, as can be understood from FIG. 1, such that the helical anchor on the distal end of the leadless pacemaker will screw into cardiac tissue for fixation thereto.

Conversely and as can be understood from FIG. 18B, on account of the pitch direction of the helical partial thread 185 on the shaft 175 of the torque portion 130, and because the proximal spring 165 biases the shuttle distally such that its distal proximal rim 260 is kept in abutting contact with the thread 185, the thread 185 of the shaft 175 engages the interior threads 250 of the shuttle 160 once the torque portion 130 is rotated counter-clockwise (CCW) and the shaft thread 185 encounters one of the multiple thread-start locations 255 intersecting the distal rim 260. Once threaded engagement occurs between the shaft thread 185 and the shuttle threads 250, further CCW rotation of the torque portion 130 will cause the shuttle 160 to distally displace along the shaft 175. This distal displacement of the shuttle will cause the lip 320 to displace distally over the O-ring 300 such that the lip 320 is once again distal the O-ring 300 and outside the proximal chamber 310, as shown in FIGS. 16A and 16B. Further CCW rotation of the torque portion 130 further drives the shuttle 160 distally until it reaches the most distal location on the shaft, as indicated in FIGS. 15A and 15B, or the grip 180 of the torque portion 130 is again rotated CW. In either case, the CCW rotation of the grip 180 will bring about CCW rotation of the helical anchor for unscrewing from cardiac tissue, and CW rotation of the grip 180 will bring about CW rotation of the helical anchor for screwing into cardiac tissue.

As can be understood from FIGS. 17A-18B, the proximal-distal width of the inner cylindrical surface 327 of the proximal chamber 310 provides proximal-distal space for the O-ring 300 reside to allow the distal spring 165 (see FIGS. 13 and 14) to reengage the shaft helical partial thread 185 with the shuttle inner thread 250 via one of the thread-start locations 255 inward of the distal rim 265 of the shuttle 160.

In the event the grip 180 is again rotated CW to bring about screwing of the helical anchor into the cardiac tissue, the embodiment of FIGS. 13-18B is advantageous in that there is nothing to "reset" to again allow for the advantages of the rotation limit warning afforded by the O-ring 300. Specifically, the resilience of the O-ring 300 and the lip 320 being positioned distal the O-ring 300 is sufficient to again avail the rotation mechanism 90 of the operational benefits of the rotation limit warning of the O-ring 300.

The warning aspect of the rotation mechanism 90 of FIGS. 13-18B could be adapted to provide multiple warnings to the physician when a certain number of rotations of the leadless pacemaker has occurred. For instance, additional O-rings 300 could be incrementally located along the shaft 175 proximal from a first O-ring 300 such that a purposeful increase in effort must be undertaken by the physician each time the physician desires to proceed with another rotation of the leadless pacemaker.

This O-ring embodiment of FIGS. 13-18B has a number of advantages. For example, the O-ring embodiment provides tactile feedback at a certain rotation level in the handle. The O-ring embodiment may be adjustable for different levels of physician effort to over-come the warning mechanism; for example, by modifying the O-ring size and durometer or changing the interference level on the shuttle.

The O-ring embodiment allows a physician to maintain focus on any fluoroscopy or information screens in the operating room. Also, no extra motion is required by the physician to over-come warning system. The O-ring embodiment informs the physician during initial implant as well as during a re-positioning of the leadless pacemaker. The warning mechanism of the O-ring embodiment may be completely hidden within the confines of the handle. Finally, the handle is omni-directional in that it does not need to be oriented in a specific fashion to go past the warning mechanism.

D. Handle with Rotation Mechanism Employing Handle Bump Limit Warning

Figure 19:
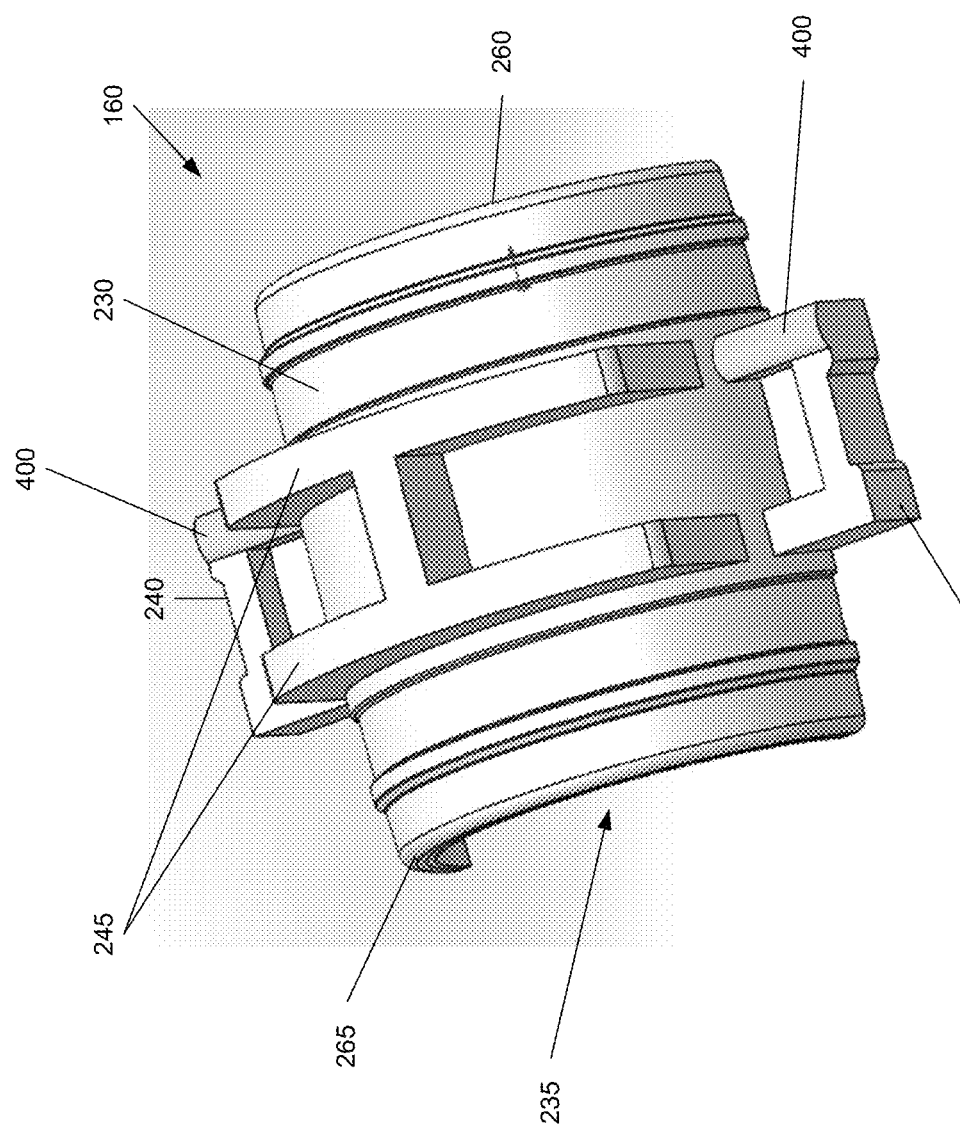
FIG. 19 is an isometric view of half of the shuttle employed in a third version of the rotation mechanism.

To begin a discussion of yet another version of the rotation mechanism 90 of the handle 108 of the leadless pacemaker delivery system of FIG. 1, reference is now made to FIG. 19, which is an isometric view of half of the shuttle 160 employed in this third version of the rotation mechanism. As shown in FIG. 19 and similar to the shuttle 160 discussed above with respect to FIGS. 8A and 8B, the shuttle 160 includes a cylindrical body 230 with a threaded cylindrical axial shaft 235 extending distal-proximal through the body 230, a pair of guide members 240 radially projecting outward from the outer circumferential surface of the body 230 on opposite sides of the body from each other, and pairs of longitudinally spaced apart ribs 245 radially projecting outward from the outer circumferential surface of the body 230 and extending circumferentially about the body. A rounded bump or ridge 400 is located on the lateral sides of each guide member 240. All other aspects of the shuttle 160 are as discussed above with respect to FIGS. 8A and 8B.

Figure 20:
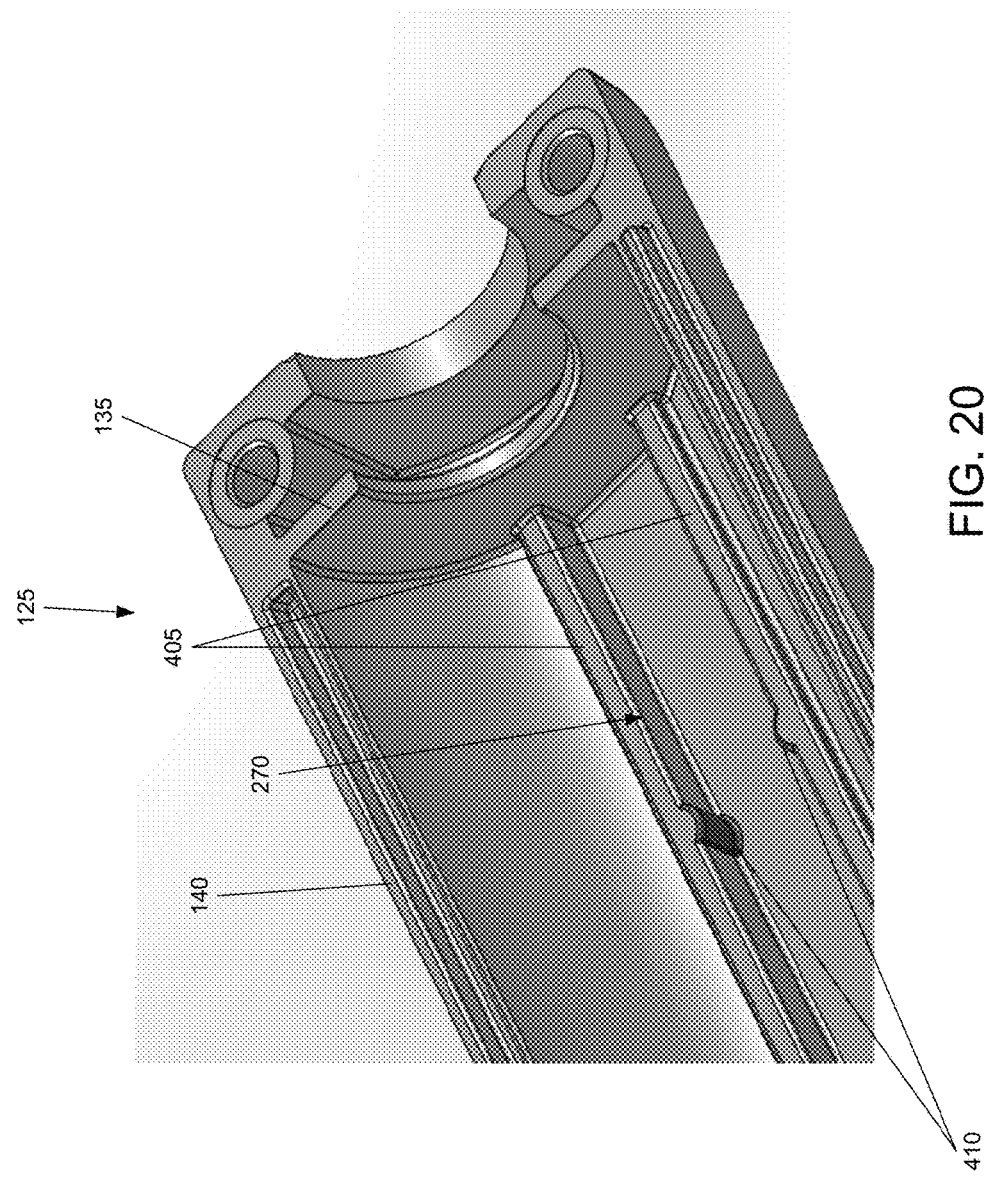
FIG. 20 is an isometric view of a half of a proximal end of the housing that is immediately adjacent the torque portion of the handle, as can be understood by comparison to FIG. 4.
Figure 21:
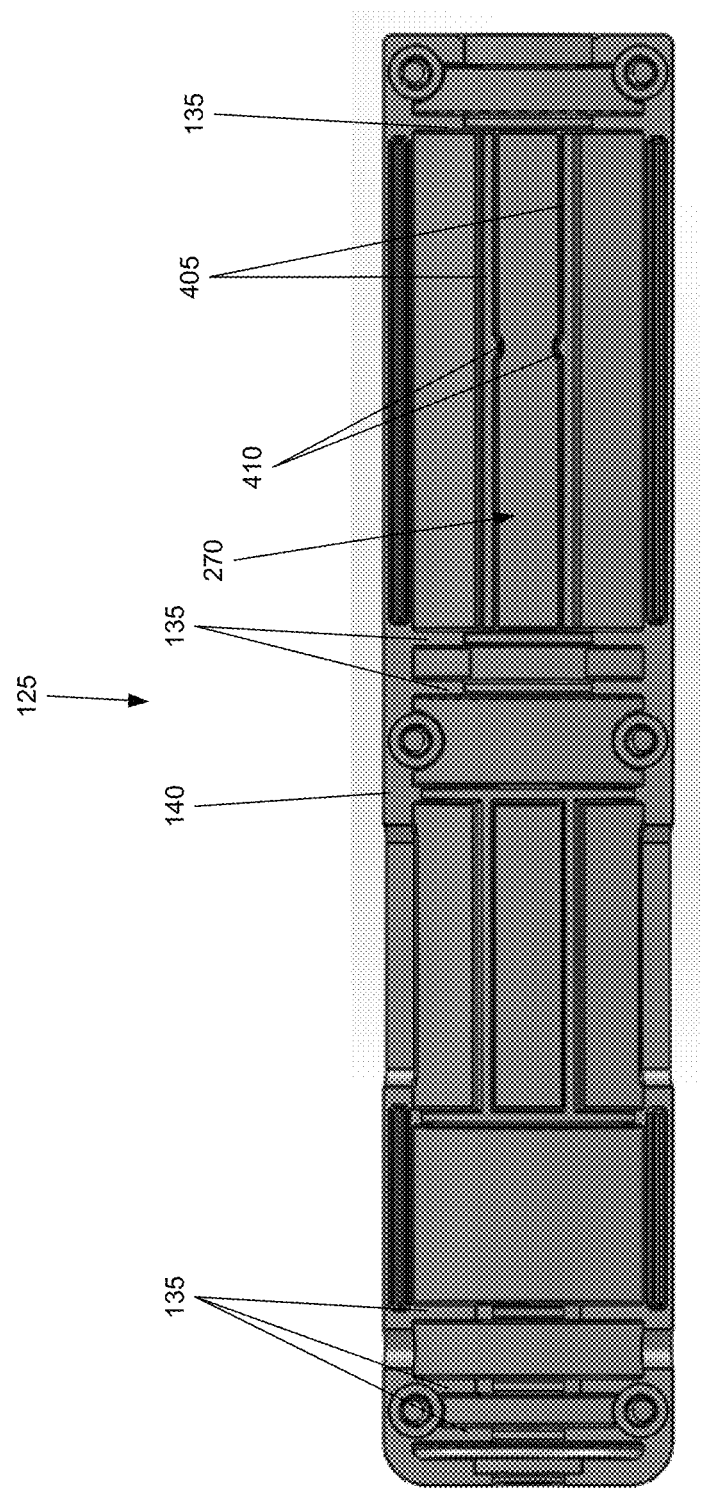
FIG. 21 is a plan view of the half of the housing of the leadless pacemaker delivery system, except employing another version of the rotation mechanism disclosed herein.

FIG. 20 is an isometric view of a half of a proximal end of the housing 125 that is immediately adjacent the torque portion 130 of the handle 108, as can be understood by comparison to FIG. 4. FIG. 21 is a plan view of the half of the housing 125. As can be understood from FIGS. 20 and 21 and similar to the discussion above with respect to FIGS. 3-5, the housing 125 includes the interior and exterior walls 135, 140 and the longitudinally extending guide slot 270, which is defined by parallel longitudinally extending rails 405. Just proximal of the midpoint of the slot 270 are opposed rounded bumps 410 projecting inwardly from its associated rail 405.

At this point, it should be noted that other aspects of the handle 108 and rotation mechanism 90 of this version of the device are substantially similar, if not identical, to those aspects and features described herein with respect to other implementations of the present disclosure, except that this version does not employ the hard stop 170 or the O-ring 300 and its interacting lips 320, 325, chamber 310 and inner circumferential surface 327. Also, the displacement of the shuttle 160 along the shaft 175, its incremental tactile sensation via the ratchet assembly 150, and its directional biasing via the springs 155, 165 all occur as discussed above with respect to FIGS. 1-18B, the difference of this version versus the previous versions being that the rotation limit warning of this third version is facilitate via the interaction of the rail bumps 410 and the shuttle bumps 400, as will now be discussed with respect to FIG. 22.

Figure 22:
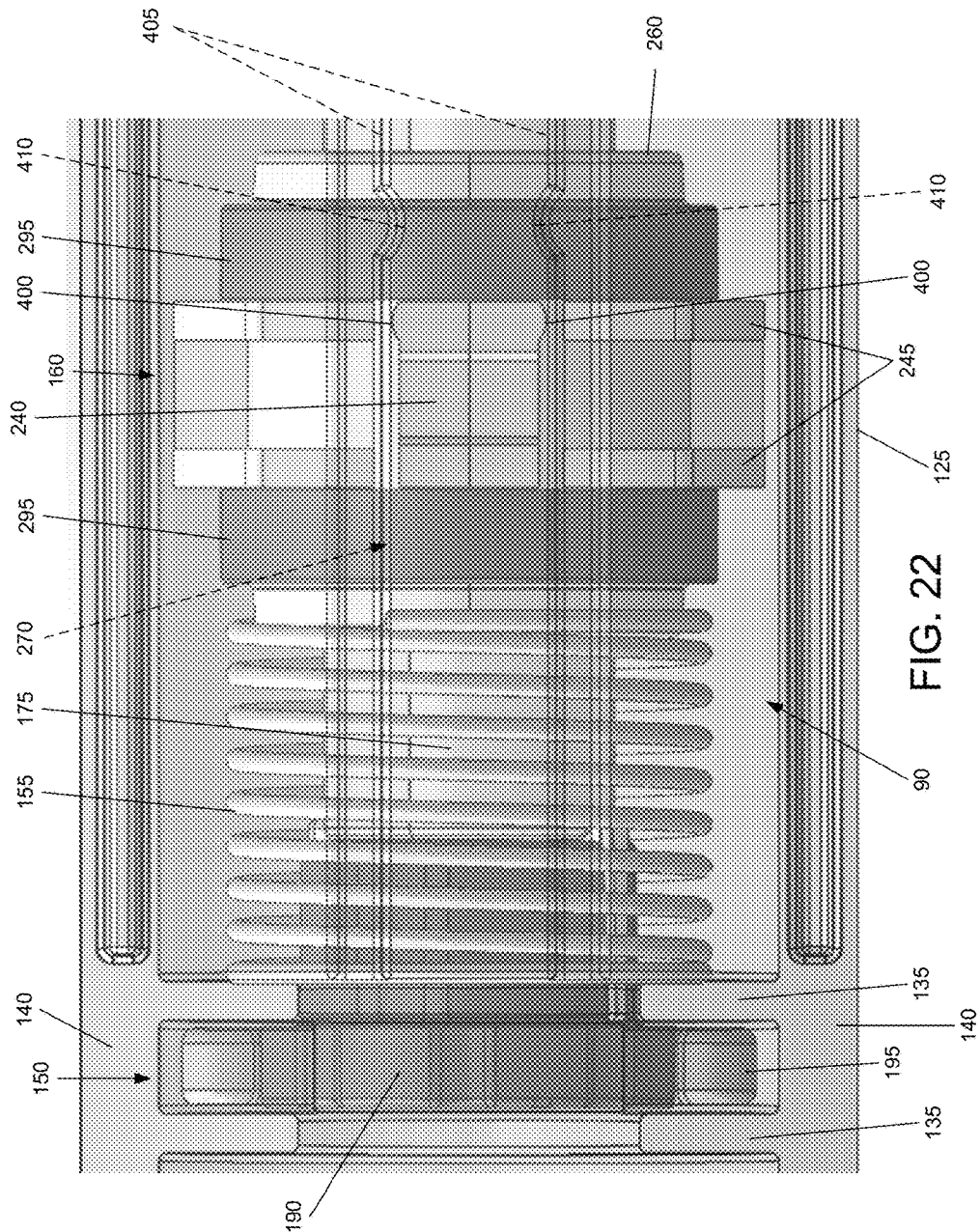
FIG. 22 is a bottom plan view of the rotation mechanism and housing.

As can be understood from FIG. 22, which is a bottom plan view of the rotation mechanism 90 and housing 125, a guide member 240 is located in a slot 270 between the rails 405, the bumps 400 of the guide member 240 projecting towards the rails 405, and the bumps 410 of the rails 405 projecting towards the guide member 240. As the shuttle 160 displaces proximally along the shaft 175 via CW rotation of the torque portion 130, the bumps 400, 410 contact, and deflect against, each other to provide a tactile increase in rotational effort at the grip 180 of the torque portion 130, thereby indicating to the physician that prescribed number of rotations of the helical anchor of the leadless pacemaker has been reached. At this point, should the physician decide additional CW rotations of the helical anchor of the leadless pacemaker are necessary to achieve a desired level of fixation to the cardiac tissue, additional CW rotations may take place. Thus, the operation of the limit warning of this third version of the rotation mechanism may be said to operate similar to that of the O-ring version discussed above with respect to FIGS. 13-18B, the exception being that the interaction of the O-ring and lips is replace by the interaction of the bumps 400, 410.

The warning aspect of the rotation mechanism 90 of FIGS. 19-22 could be adapted to provide multiple warnings to the physician when a certain number of rotations of the leadless pacemaker has occurred. For instance, additional pairs of rail bumps 410 could be incrementally located along the slot 270 proximal from a first pair of rail bumps 410 such that a purposeful increase in effort must be undertaken by the physician each time the physician desires to proceed with another rotation of the leadless pacemaker.

The warning mechanism afforded by the bumps can be adjusted for different levels of physician effort to overcome the warning mechanism; for example, by modifying the level of interference by changing bump height and modifying flexural stiffness of shuttle ribs on which the housing bumps are located. All the bump features can be molded into place. The warning mechanism allows the physician to maintain focus on any fluoroscopic or information screens in the operating room, and no extra motion is required by the user to over-come warning system. The warning mechanism may inform the physician during initial implant as well as during a re-positioning. The warning mechanism may be completely encapsulated inside handle, and the handle may be omni-directional in that it does not need to be oriented in a specific fashion to go past the warning mechanism.

E. Handle with Rotation Mechanism Employing Malleable Thread

Figure 23:
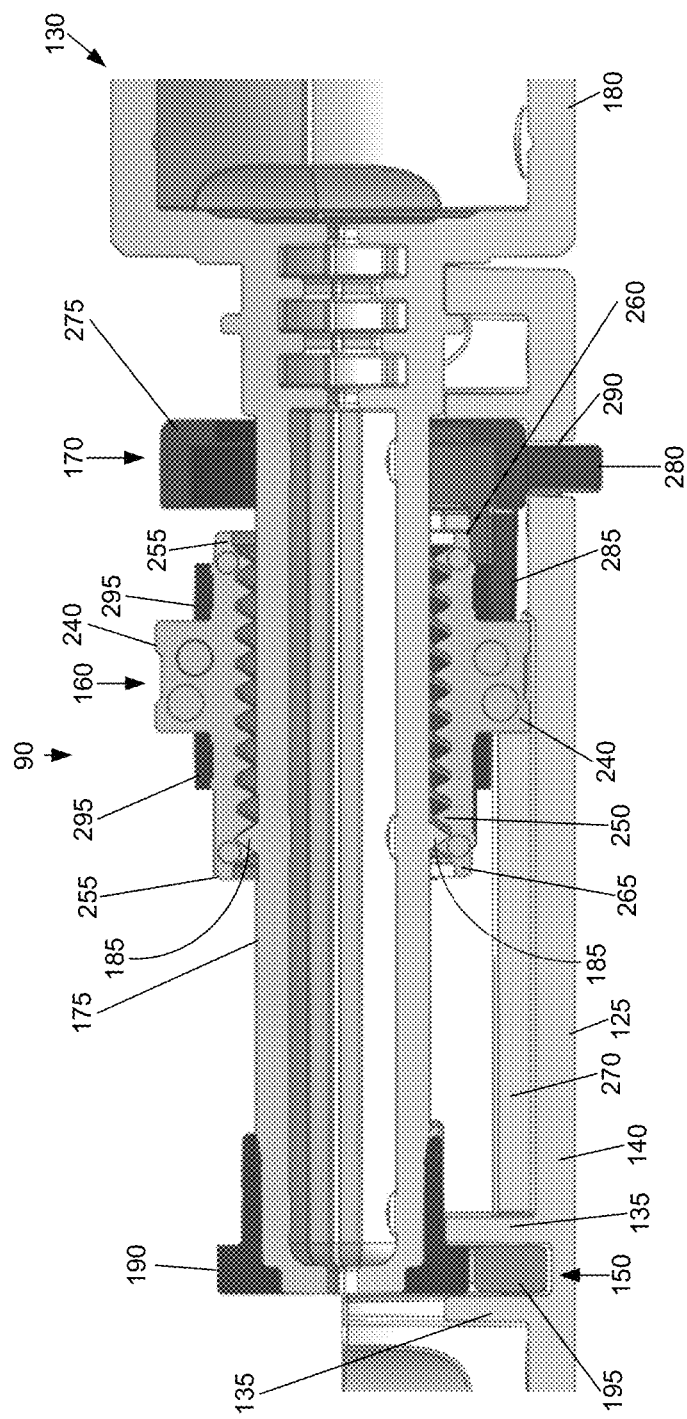
FIG. 23 is a longitudinal cross sectional view of the leadless pacemaker delivery system, except employing another version of the rotation mechanism.

To begin a discussion of yet another version of the rotation mechanism 90 of the handle 108 of the leadless pacemaker delivery system of FIG. 1, reference is now made to FIG. 23, which is a longitudinal cross-section of a rotation mechanism 90 in accordance with this disclosure. As shown in FIG. 23 and similar to the shuttle 160 discussed above with respect to FIGS. 8A and 8B, the shuttle 160 includes a cylindrical body 230 with a threaded cylindrical axial shaft 235 extending distal-proximal through the body 230 and including one or more threads 250, a pair of guide members 240 radially projecting outward from the outer circumferential surface of the body 230 on opposite sides of the body 230 from each other, and pairs of longitudinally spaced apart ribs 245 radially projecting outward from the outer circumferential surface of the body 230 and extending circumferentially about the body. The shuttle 160 of FIG. 23 is sized such that when the shuttle 160 is in a proximal position, at least a portion of the threads 250 engage a helical partial thread 180 of a torque portion 130 of a handle 108. Generally, the proximal position of the shuttle 160 is a position in which further proximal translation of the shuttle 160 is prevented by another structure or component of the rotation mechanism 90. For example, in certain implementations, the proximal position may correspond to a maximum proximal position at which the shuttle 160 abuts a proximal interior wall of the handle 108 (such as the interior wall 135 shown in FIG. 18B) or is prevented from additional proximal translation by a compressed spring, bumper, or similar resilient structure disposed between the shuttle 160 and a proximal interior wall of the handle 108. As illustrated in FIG. 23, the proximal position may also correspond to one or more positions of the shuttle 160 at which the shuttle 160 is prevented from additional proximal translation by a stop ring 170 having one or more distinct stops (as previously discussed in the context of FIGS. 2-12B). At this point, it should be noted that other aspects of the handle 108 and rotation mechanism 90 of this version of the device are substantially similar, if not identical, to those aspects and features described herein with respect to the other versions of the present disclosure, except in this version the shuttle 160 is sized such that at least a portion of the threads 250 of the shuttle 160 engage the partial helical partial thread 185 of the handle 108 when the shuttle 160 is in a proximal position.

In rotation mechanisms according to this version of the rotation mechanism, tactile feedback is provided by threads adapted to deform or fail when sufficient torque is applied to the torque portion 130 of the handle 108 after the shuttle 160 has reached a proximal position. More specifically, when the shuttle 160 reaches the proximal position by rotation of the torque portion 130, additional translation of the shuttle 160 is prevented by features of the rotation mechanism 90, such as the stop ring 170, or, in other implementations a spring (such as the spring 165 shown in FIG. 14), an interior wall of the handle 108 (such as the interior wall 135 shown in FIG. 18B), a bumper (such as the elastomeric bumpers 490, 495 shown in FIG. 25), or any similar structure disposed between the handle 108 that prevents proximal translation of the shuttle 160.

When the shuttle 160 is in the proximal position (as shown in FIG. 23), additional torque applied to the torque portion 130 results in stress applied to a portion of the threads 250 of the shuttle 160 and the partial helical partial thread 185 of the handle 108. If the torque applied is sufficiently high, one or both of the threads 250 and the partial helical partial thread 185 may deform and/or fail. When such deformation or failure occurs, the threads 250 and the partial helical thread 285 may disengage and, as a result, the torque portion 130 may freely rotate within the housing 180.

In light of the foregoing, the rotation mechanism 90 illustrated in FIG. 23 provides tactile feedback and warning by resisting rotation of the torque portion 130 when the shuttle 160 reaches the proximal position. More specifically, as the shuttle 160 translates towards the proximal position, rotation of the torque portion 130 is opposed by a rotational resistance which may be attributable to friction of components of the rotation mechanism 90 or other features, such as springs, that may be disposed proximal the shuttle 160. When the shuttle 160 reaches the proximal position, the shuttle 160 is generally prevented from further translation in the proximal direction and, as a result, a warning in the form of substantially increased rotational resistance occurs. In certain implementations, the rotation mechanism 90 may be configured to translate the shuttle 160 from a distal position to the proximal position in a predetermined number of rotations of the torque portion 130, such as two and one quarter rotations.

When the shuttle 160 reaches the proximal position, a user may continue to rotate the torque portion 130 to cause further rotation of the leadless pacemaker coupled to the handle 108. However, because the shuttle 160 is substantially prevented from further advancement, such additional rotation causes stress on the threads 250 of the shuttle 160 and the partial helical thread portion 185 of the torque portion 130 and, as a result, increases resistance to rotation of the torque portion 130. In certain implementations, further rotation of the torque portion 130 may result in reversible elastic deformation of one or both of the threads 250 and the helical thread portion 185. If the number of additional rotations results in sufficient stress, one or both of the threads 250 and the helical thread portion 185 may plastically deform or otherwise fail. In cases of brittle failure of one or both of the threads 250 and the helical partial thread 185, a substantial reduction in resistance to rotation of the torque portion 130 may occur. In cases of ductile failure, the tactile feedback may be felt by a user as a gradual decrease in resistance to rotation of the torque portion 130. In either case, when sufficient failure has occurred, resistance to rotation of the torque portion 130 may be reduced to a nominal level as the threads 250 and the partial helical partial thread 185 (to the extent either remains after the failure) will be substantially disengaged.

The warning aspect of the rotation mechanism 90 of FIG. 23 may be adapted to provide controlled failure of either the threads 250 or the partial helical partial thread 185 in response to a particular torque applied using the torque portion 130. By varying the structure, material, shape, or other aspects of the portion of the threads 250 or the partial helical partial thread 185, failure and, as a result, feedback provided in conjunction with such failure may be controlled. For example, one or both of the materials of the thread 250 and the partial helical partial thread 185 may be selected to have a specific hardness, elastic modulus, or other material property related to failure. Alternatively or in addition to specific material selection, the thread 250 or the partial helical partial thread 185 may have a predetermined cross-section, thickness, or shape corresponding to a particular point of failure. Notably, the parameters used to modify the failure point of the thread 250 or the partial helical partial thread 185 may be applied to the thread 250 or the partial helical partial thread 185 in their entirety or may only correspond to a portion thereof. For example, as shown in FIG. 23, a known portion of the thread 250 may engage the partial helical partial thread 185 when the shuttle 160 is in the proximal position based on the geometry of components of the handle 108. Accordingly, in certain implementations, only the known portion of the thread 250 may be formed of a particular material or have a particular geometry corresponding to achieve the desired failure point and rotational resistance profile.

F. Handle with Rotation Mechanism Employing a Bump and Compliant Shuttle

Figure 24:
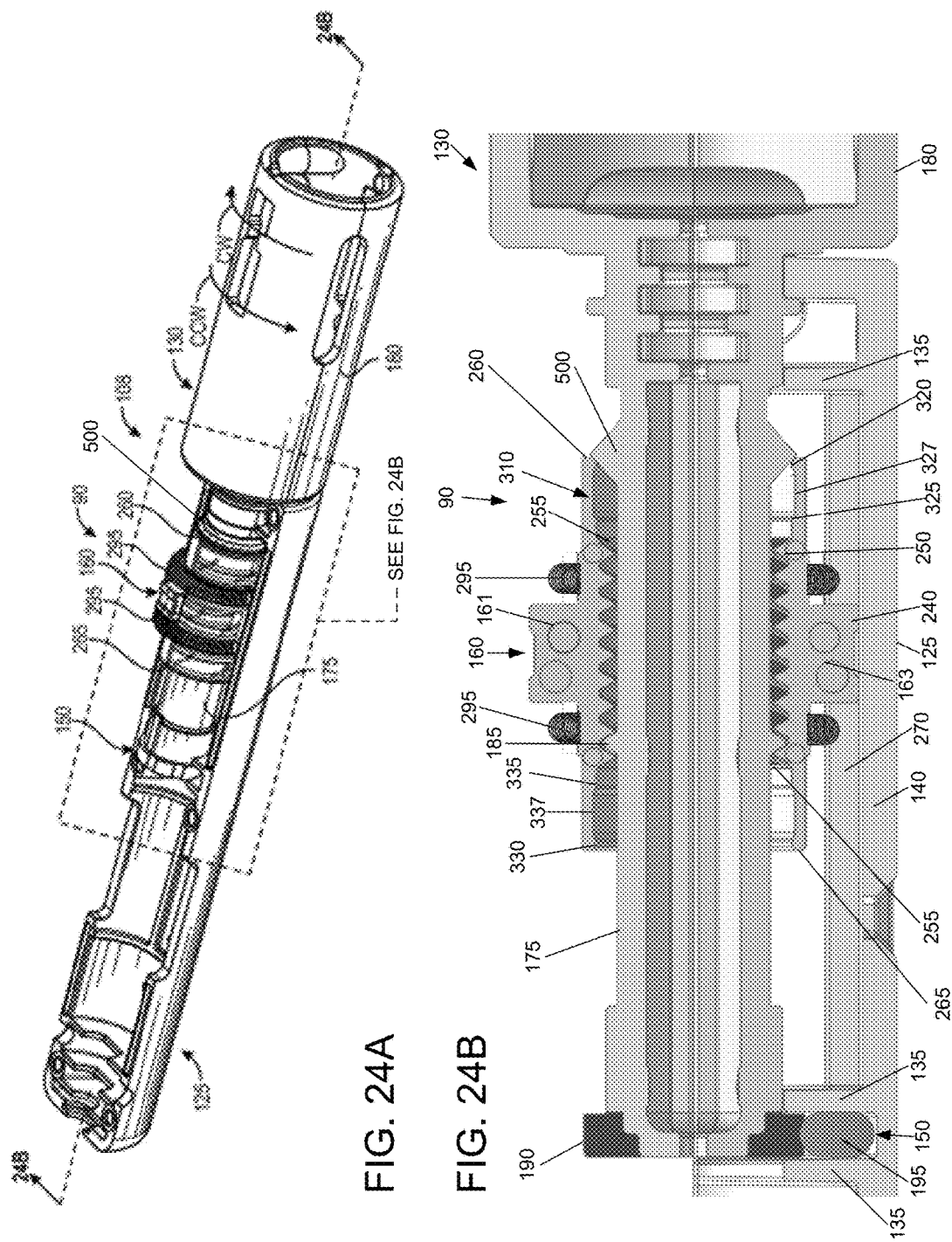
FIG. 24A is an isometric view of the handle of the leadless pacemaker delivery system, except employing another version of the rotation mechanism disclosed herein, wherein a portion of a housing of the handle is removed to reveal the rotation mechanism enclosed therein.
FIG. 24B is a longitudinal cross section of the handle and rotation mechanism enclosed therein as viewed along section line 24B-24B in FIG. 24A with the shuttle in a first position.
Figure 25:
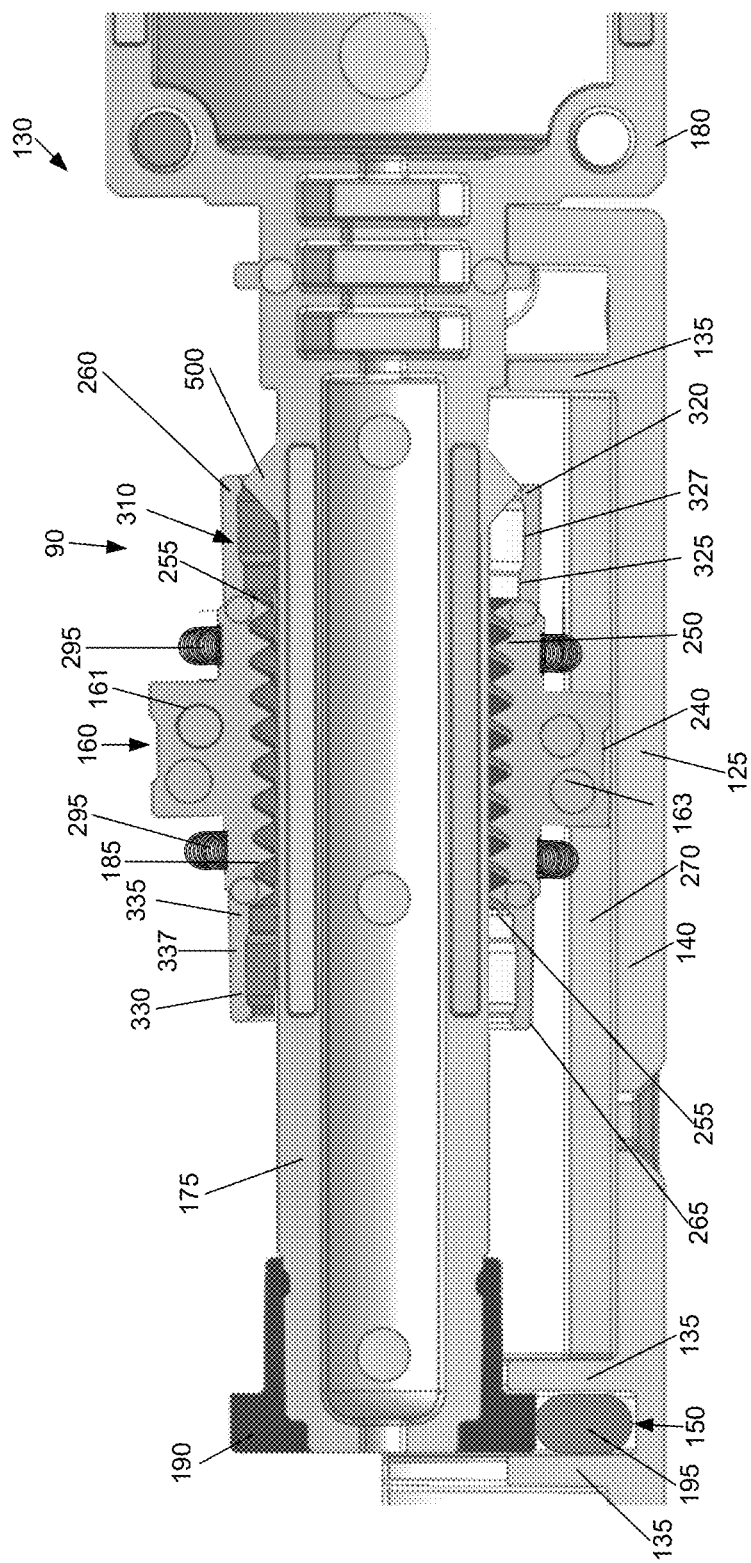
FIG. 25 is a longitudinal cross section of the handle and rotation mechanism enclosed therein as viewed along section line 24B-24B in FIG. 24A with the shuttle in a second position.
Figure 26:
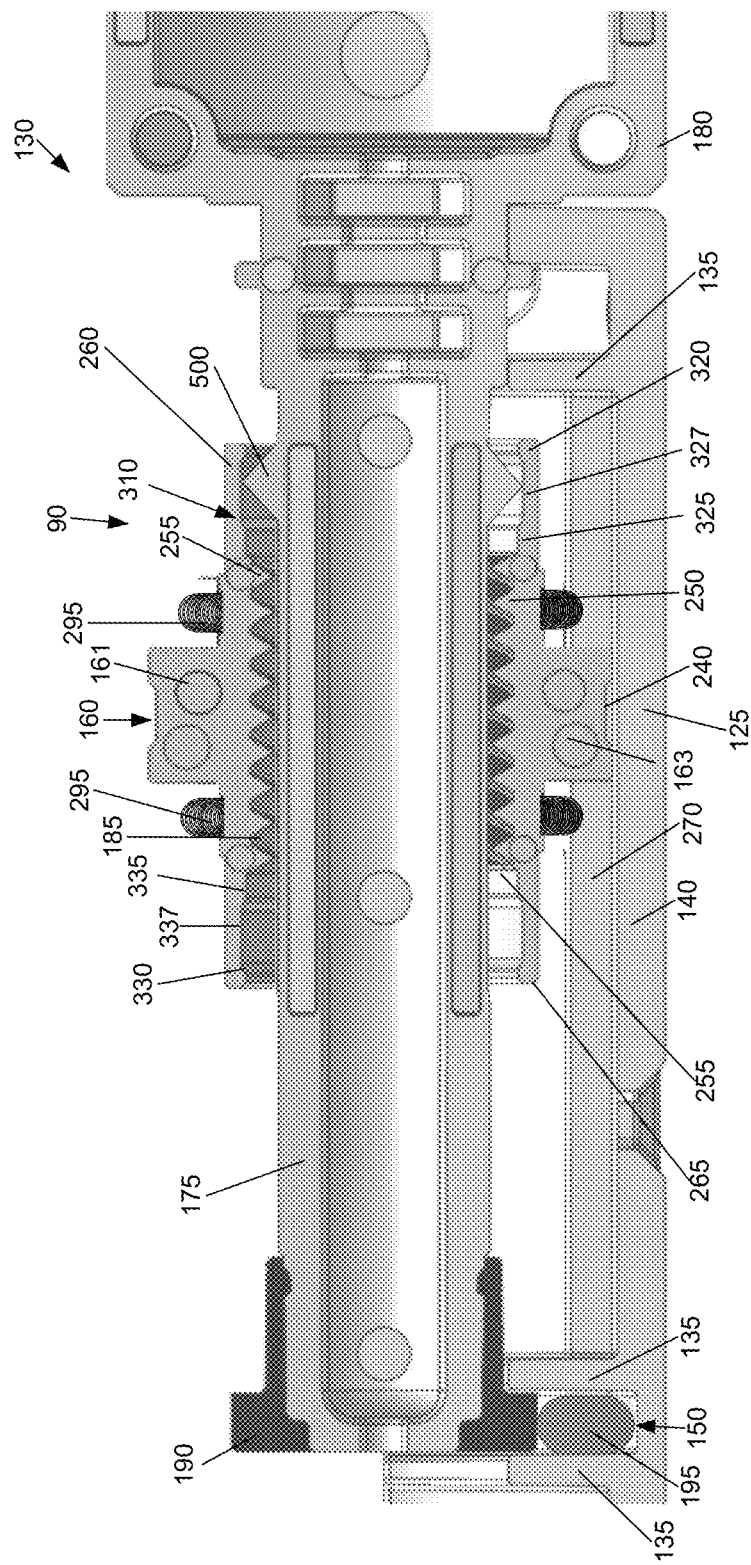
FIG. 26 is a longitudinal cross section of the handle and rotation mechanism enclosed therein as viewed along section line 24B-24B in FIG. 24A with the shuttle in a third position.

To begin a discussion of another embodiment of the rotation mechanism 90 of the handle 108 of the leadless pacemaker delivery system of FIG. 1, reference is now made to FIGS. 24A-26. FIG. 24A is an isometric view of the handle 108 with a portion of a housing 125 of the handle 108 removed to reveal the alternative rotation mechanism 90 enclosed therein. FIG. 24B is a longitudinal cross-section of the rotation mechanism 90 in the region identified in FIG. 24A and as taken along section line 24B-24B in FIG. 24A. FIGS. 25 and 26 are additional longitudinal cross-sections of the rotation mechanism 90 in the region identified in FIG. 24A.

As can be understood from a comparison of FIG. 24A-26 to FIGS. 1-18B, the alternative version of the rotation mechanism 90 and the surrounding elements of the handle 108 and leadless pacemaker delivery system of FIGS. 24A-26 share the majority of elements and operation as discussed above with respect to FIGS. 1-18B. With reference to FIGS. 13-18B, in particular, however, the O-ring 300 of FIGS. 13-18B and relate retention structure has replaced by a bump 500 disposed on the shaft 175 and the rings 295 coupled to the shuttle 160 have been replaced by a pair of garter springs 502, 504 extending around the shuttle 160. Further, the shuttle 160 is a multi-part shuttle that includes at least two separate shuttle segments 161, 163. The springs 155, 165 have also been omitted for clarity. Accordingly, the preceding discussion of FIGS. 1-18B is equally applicable to the version of the rotation mechanism 90 and surrounding elements of the handle 108 shown in FIGS. 24B-26, except as will now be specifically discussed with respect to FIGS. 24B-26.

As indicated in FIGS. 24A and 24B, the garter springs 502, 504 extend circumferentially around a distal and proximal end of the shuttle 160 and are coaxial with, the shaft 175 of the torque portion 130. The garter springs 502, 504 exert an inward force on the shuttle 160 such that the shuttle segments 161, 163 are made to abut each other and retain the overall shape of the shuttle 160 in a resting configuration. In certain implementations, the garter springs 502, 504 may be retained within structures of the shuttle 160 such as between parallel circumferential flanges of the shuttle 160 or within grooves defined in the outer surface of the shuttle 160. The garter springs 502, 504 may be made of materials, such as, for example, metals or elastomeric polymers. In certain implementations one or both of the garter springs 502, 504 may be replaced by an elastic band or similar compliant member shaped to extend around the shuttle 160. Also, while illustrated in FIGS. 24A-25 as including two garter springs 502, 504 additional garter springs (or similar compliant) may be included.

As shown in FIG. 24B, the proximal end of the shaft 175 of the torque portion 130 includes a bump 500 or similar structure extending from the shaft 175. The bump 500 may be integrally formed with the shaft 175 and may extend around all or part of the circumference of the shaft 175. The bump 500 may have various shapes and sizes, however, as further discussed with respect to FIGS. 24B-26, below, the bump 500 generally extends from the shaft 175 such that as the shuttle 160 translates proximally along the shaft 175, the bump 500 contacts a feature, such as a proximal edge 260, a bump, a lip, or similar protrusion of the shuttle 160. Further translation of the shuttle 160 causes the bump 500 to force the shuttle segments 161, 163 apart, providing tactile feedback in the form of increased resistance to the user of the rotation mechanism 90. In certain implementations, the bump 500 may be substituted with an O-ring or similar structure retained on the shaft 175, such as illustrated in FIGS. 13-18B. In such implementations, the O-ring may function similarly to the bump 500 of FIGS. 24-26B by, among other things, resisting proximal translation of the shuttle 160 such that proximal translation of the shuttle 160 requires separation of the 161, 163. Deformation of the O-ring may also occur such that the increased rotational resistance provided to a user results from a combined effect of the O-ring deformation and the behavior of the garter springs 502, 504.

As shown in FIG. 24A, the shuttle 160 may include a proximal inner circumferential chamber 310 at the proximal end of the shuttle and a distal inner circumferential chamber 315 at the distal end of the shuttle. Each chamber 310, 315 may include a pair of spaced-apart radially inwardly extending lips, bumps, or similar features. In the example of FIG. 24A, these lips include an outer lip and an inner lip. Specifically, for the proximal chamber 310, the outer lip is a proximal outer lip 320 at the proximal edge of the shuttle 160, and the inner lip is a distal inner lip 325 distal the proximal outer lip 320. The lips 320, 325 are spaced-apart from each other and radially inwardly project from an inner cylindrical surface 327 of the proximal chamber 310. For the distal chamber 315, the outer lip is a distal outer lip 330 at the distal edge of the shuttle 160, and the inner lip is a proximal inner lip 335 proximal the distal outer lip 330. The lips 330, 335 are spaced-apart from each other and radially inwardly project from an inner cylindrical surface 337 of the distal chamber 315.

When the shuttle 160 is in the most distal location along the shaft 175 of the torque portion 130 of the handle 108, the distal spring 155 (shown in FIGS. 13 and 14) is compressed between the distal ring 295 of the shuttle 160 and an interior wall 135 immediately proximal the ratchet assembly 150. On account of the pitch direction of the helical partial thread 185 on the shaft 175 of the torque portion 130, and despite the distal spring 155 biasing the shuttle proximally such that its distal rim 265 is kept in abutting contact with the thread 185, the thread 185 of the shaft 175 does not engage the interior threads 250 of the shuttle 160 as long as the torque portion 130 is rotated counter-clockwise (CCW), the thread 185 simply riding along the distal rim 265 of the shuttle 160. Thus, the torque portion 130 and the linear member 120 extending distally therefrom (as shown and discussed in the context of FIG. 13), can infinitely rotate CCW and cause the leadless pacemaker 102 to rotate CCW, as can be understood from FIG. 1, such that the helical anchor on the distal end of the leadless pacemaker will unscrew from cardiac tissue in which it may be imbedded. The CCW rotation causes the ratchet assembly 150 to generate an incremental/stepped tactile sensation in the grip 180 of the torque portion 130 of the handle 108.

Conversely, on account of the pitch direction of the helical partial thread 185 on the shaft 175 of the torque portion 130, and because the distal spring 155 (shown in FIGS. 13 and 14) biases the shuttle proximally such that its proximal rim 265 is kept in abutting contact with the thread 185, the thread 185 of the shaft 175 engages the interior threads 250 of the shuttle 160 once the torque portion 130 is rotated clockwise (CW) and the shaft thread 185 encounters one of the multiple thread-start locations 255 intersecting the proximal rim 265. Once threaded engagement occurs between the shaft thread 185 and the shuttle threads 250, further CW rotation of the torque portion 130 will cause the shuttle 160 to proximally displace along the shaft 175. As can be understood from FIGS. 1 and 13, the CW rotation of the torque portion 130 and the linear member 120 extending distally therefrom rotates the leadless pacemaker 102 CW such that the helical anchor on the distal end of the leadless pacemaker will screw into cardiac tissue contacting the helical anchor. The CW rotation causes the ratchet assembly 150 to generate an incremental/stepped tactile sensation in the grip 180 of the torque portion 130 of the handle 108.

Continued CW rotation of the torque potion 130 further proximally displaces the shuttle 160 along the shaft 175 as the shuttle threads 250 move proximally along the rotating shaft thread 185, which is confined to rotation about the longitudinal axis of the shaft and does not displace distal-proximal. As the shuttle moves along the shaft, the shuttle guide members 240 linearly displace proximally along the respective guide slots 270. In some embodiments where the guide slots 270 daylight through the exterior wall 140 of the housing 125, the displacement of the shuttle guide members 240 can be observed through the windows created by the guide slots 270 in the exterior wall 140 of the housing 125, similar to that discussed above with respect to FIGS. 2, 4 and 5.

As the CW rotation of the torque portion 130 causes the shuttle 160 to displace proximally from the most distal location, the tactile sensation and resistance felt in the grip 180 of the torque portion 130 will remain constant as provided by the ratchet assembly 150 until the shuttle 160 is sufficiently proximally displaced such that the proximal boundary of the proximal outer lip 320, which is at the shuttle proximal edge 260, encounters the bump 500, as illustrated in FIGS. 24A and 24B. At this time, the resistance felt in the grip 180 of the torque portion 130 will begin to gradually increase as the radially inwardly projecting lip 320 travels across the bump 500. More specifically, the bump 500 causes separation of the shuttle segments 161, 163, which is increasingly resisted by the proximal garter spring 504 as the separation increases.

In one embodiment, the number of CW rotations needed to displace the shuttle from a most distal position to the stopped position shown in FIGS. 24A and 24B will be two and one-quarter rotations of the grip 180 of the torque portion 130 of the handle 108. This two and one-quarter rotations is based on what is considered to be a typical number of turns of the helical anchor of the leadless pacemaker to cause the helical anchor to fully imbed in the cardiac tissue without over-penetrating the cardiac tissue. In other embodiments, the number of rotations required to displace the shuttle between the most distal location and the location depicted in FIGS. 24A-24B will be more or less than two and one-quarter rotations.

Once the proximal boundary of the proximal outer lip 320, which is at the shuttle proximal edge 260, encounters the bump 500, as illustrated in FIGS. 24A and 24B, this contact will notify the physician that the prescribed number of rotations of the helical anchor of the leadless pacemaker has been reached. At this point, should the physician decide additional CW rotations of the helical anchor of the leadless pacemaker are necessary to achieve a desired level of fixation to the cardiac tissue, as can be understood from FIGS. 25-26, continued CW rotations of the grip 180 of the torque portion 130 of the handle 108 will continue to proximally displace the shuttle 160 and drive the radially inwardly projecting lip 320 at the shuttle proximal edge 260 completely over and proximally past the bump 500 such that the bump 500 is received in the proximal inner circumferential chamber 310 as indicated in FIG. 26.

In certain implementations, such as that illustrated in FIGS. 24A-26, the bump 500 may permit reversal of the shuttle 160. For example, after the radially inwardly projecting lip 320 passes a peak of the bump 500, the grip 180 may be rotated CCW to cause the shuttle 160 to translate in the distal direction. As the shuttle 160 distally translates, the bump 500 will again the shuttle 160 and, as the shuttle further translates, separation of the shuttle segments 161, 163, resulting in tactile feedback as previously described.

The warning aspect of the rotation mechanism 90 of FIGS. 24A-26 may be adapted to provide multiple and varying warnings to a physician in response to rotation of the leadless pacemaker. For instance, additional bumps 500 could be incrementally located along the shaft 175 proximal from a first bump such that each bump causes a change in the rotational resistance of the grip 180. Such a sequence of bumps may be distributed along the shaft 175 such that each bump corresponds to a specific number of rotations of the leadless pacemaker. The shuttle 160 may also include multiple lips or similar features that contact and must pass over one or more bumps disposed along the shaft 175. The shape of the bump 500 or lip of the shuttle 160 may also be altered to change the resistance encountered during rotation of the grip 180. For example, the overall height of the bump 500 or lip may be increased or decreased to modify the peak rotational force required to overcome the bump 500. Similarly, the length and slope of the bump 500 or lip may be altered to change the rate at which the rotational resistance of the grip 180 increases. Resistance to rotation of the grip 180 may also be modified by changing the inward force provided by the compliant members 502, 504 to the shuttle segments 161, 163. For example, one or more of the material, thickness, quantity, and placement of the compliant members 502, 504 may be modified to vary the resistance to rotation of the grip 180 provided by the compliant members 502, 504.

G. Handle with Rotation Mechanism Employing Elastomeric Bumper

Figure 27:
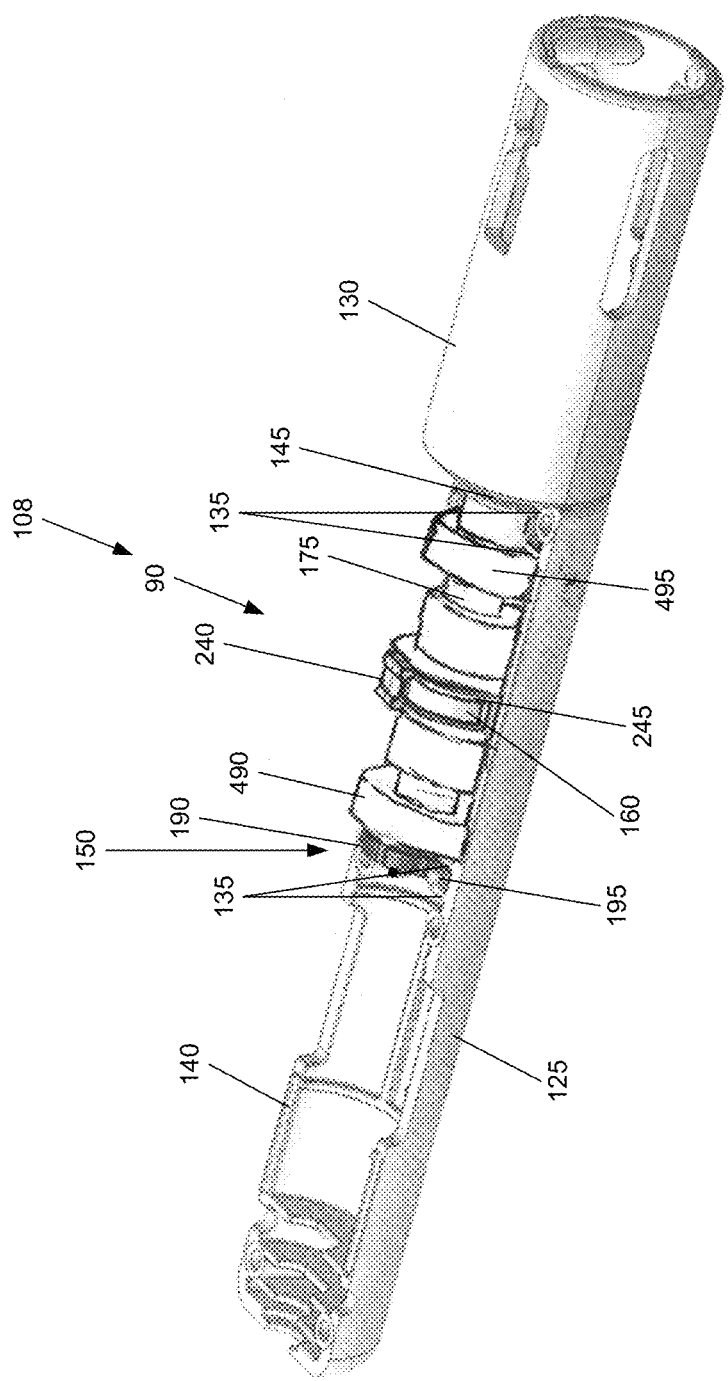
FIG. 27 is an isometric view of the handle of the leadless pacemaker delivery system, except employing another version of the rotation mechanism disclosed herein, wherein a portion of a housing of the handle is removed to reveal the rotation mechanism enclosed therein.

To begin a discussion of yet another version of the rotation mechanism 90 of the handle 108 of the leadless pacemaker delivery system of FIG. 1, reference is now made to FIG. 27, which is an isometric view of the handle 108 with a portion of a housing 125 of the handle 108 removed to reveal the alternative rotation mechanism 90 enclosed therein.

As can be understood from a comparison of FIG. 27 to FIGS. 13-14, the alternative version of the rotation mechanism 90 and the surrounding elements of the handle 108 and leadless pacemaker delivery system of the version of FIG. 25 share the majority of elements and operation as discussed above with respect to FIGS. 13-14, except that the springs 155, 165 disposed between the shuttle 160 and the interior walls 135 have been removed and replaced with elastomeric bumpers 490, 495. Accordingly, the preceding discussion of FIGS. 13-14 is equally applicable to the version of the rotation mechanism 90 and surrounding elements of the handle 108 shown in FIG. 27, except as will now be specifically discussed with respect to FIG. 27.

As indicated in FIG. 27, a distal bumper 490 and a proximal bumper 495 are retained against distal and proximal interior walls 135 of the housing 180. As shown in FIG. 25, each of the distal bumper 490 and the proximal bumper 495 extend circumferentially around, and are coaxial with, the shaft 175 of the torque portion 130. The bumpers 490, 495 are disposed between the shuttle 160 and corresponding distal and proximal internal walls 135 of the handle 108 such that as the shuttle 160 approaches its distal and proximal extents within the handle 108, the distal and proximate bumpers 490, 495 are compressed between the shuttle 160 and the distal and proximal internal walls 135, respectively. In an alternative implementation, one or both of the distal bumper 490 and the proximal bumper 495 may instead be retained on distal and proximal ends of the shuttle 160, respectively, and perform similar functions as described below. In still other implementations, the distal bumper 490 may be omitted.

When the shuttle 160 is in the most distal location along the shaft 175 of the torque portion 130, the distal bumper 490 is compressed between the shuttle 160 and an interior wall 135 immediately proximal the ratchet assembly 150. On account of the pitch direction of the helical partial thread 185 on the shaft 175 of the torque portion 130, and despite the distal compliant member 390 biasing the shuttle 160 proximally such that its distal rim 265 (see, e.g., FIGS. 8A and 8B) is kept in abutting contact with the thread 185, the thread 185 of the shaft 175 does not engage the interior threads 250 of the shuttle 160 as long as the torque portion 130 is rotated counter-clockwise (CCW), the thread 185 simply rides along the distal rim 265 of the shuttle 160. Thus, the torque portion 130 and the linear member 120 extending distally therefrom, as shown in FIG. 3, can infinitely rotate CCW and cause the leadless pacemaker 102 to rotate CCW, as can be understood from FIG. 1, such that the helical anchor on the distal end of the leadless pacemaker will unscrew from cardiac tissue in which it may be imbedded.

Conversely, on account of the pitch direction of the helical partial thread 185 on the shaft 175 of the torque portion 130, and because the distal compliant member 390 biases the shuttle 160 proximally such that its proximal rim 265 is kept in abutting contact with the thread 185, the thread 185 of the shaft 175 engages the interior threads 250 of the shuttle 160 once the torque portion 130 is rotated clockwise (CW) and the shaft thread 185 encounters one of the multiple thread-start locations 255 intersecting the proximal rim 265. Once threaded engagement occurs between the shaft thread 185 and the shuttle threads 250, further CW rotation of the torque portion 130 will cause the shuttle 160 to proximally displace along the shaft 175. As can be understood from FIGS. 1 and 3, the CW rotation of the torque portion 130 and the linear member 120 extending distally therefrom rotates the leadless pacemaker 102 CW such that the helical anchor on the distal end of the leadless pacemaker will screw into cardiac tissue contacting the helical anchor. In certain implementations, the CW rotation causes the ratchet assembly 150 to generate an incremental/stepped tactile soft-stop sensation in the grip 180 of the torque portion 130 of the handle 108.

As the CW rotation of the torque portion 130 causes the shuttle 160 to displace proximally from the most distal location, the tactile sensation and resistance felt in the grip 180 of the torque portion 130 will remain constant as provided by the ratchet assembly 150 until the shuttle 160 is sufficiently proximally displaced such that the proximal face of the shuttle 160 contacts the proximal bumper 495, which is disposed adjacent a proximal interior wall 135. Further CW rotation of the torque portion 130 causes compression of the proximal bumper 495 and, as a result, increased resistance to continued movement of the shuttle 160 in the proximal direction. Accordingly, a user of the rotation mechanism 90 receives an initial warning in the form of increased resistance to rotation of the torque portion 130. After initial contact between the proximal compliant member 195 and the proximal internal wall 135, a user of the rotation mechanism 90 may decide whether additional CW rotations of the helical anchor of the leadless pacemaker are necessary to achieve a desired level of fixation to the cardiac tissue. If additional CW rotations are applied, the rotational resistance provided by the proximal bumper 495 may increase accordingly.

Each of the bumpers 490, 495 may be made of materials such as, for example, metals, compressible polymers, and/or etc. While depicted as being solid tubules in the implementation of FIG. 27, the bumpers 490, 495 are not limited to such a shape. For example, in certain implementations, the compliant member 490, 495 may be helical springs or may include internal or external grooves, cutouts, or combinations thereof. In certain instances, the bumpers 490, 495 may include multiple sections, each of which may be composed of a different material or have a different geometry. In light of the foregoing, the warning aspect of the rotation mechanism 90 of FIG. 27 may be adapted by modifying the material and structure of the bumpers 490, 495. For example, a high rotational resistance and a high rate of rotational resistance increase may be achieved by using bumpers composed of relatively stiff materials. Rotational resistance may also be modified by forming grooves or cutouts (including, without limitation, longitudinal, circumferential, and helical grooves or cutouts) on the bumper, with the relative spacing, depth, and width of the grooves or cutouts modifying the overall stiffness of the bumper.

H. Handle with Electronic Warning Mechanism

Figure 28A:
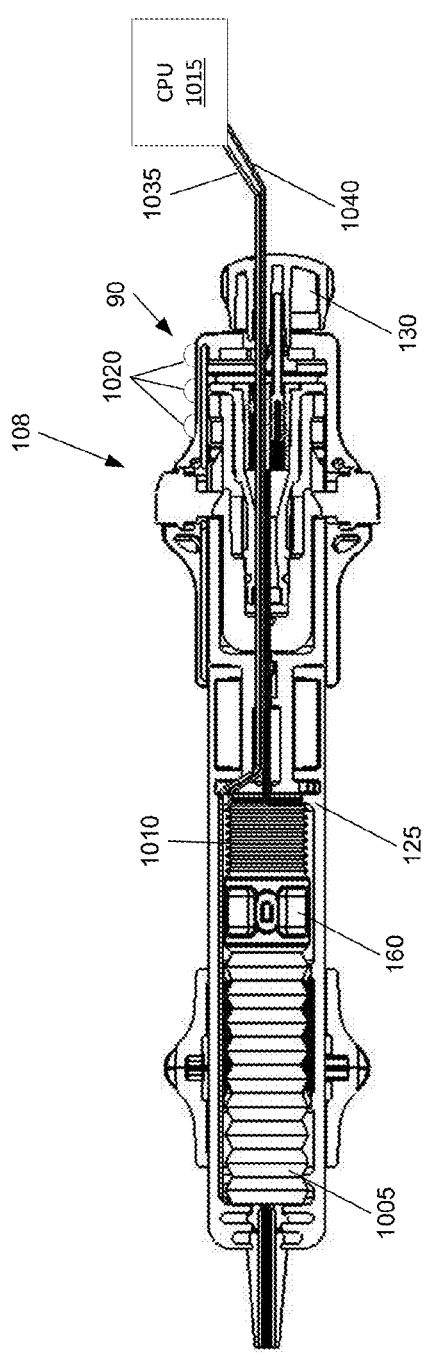
FIGS. 28A-28B are longitudinal cross sectional views of the handle of the leadless pacemaker delivery system to reveal the rotation mechanism enclosed therein, except employing another version of the rotation mechanism disclosed herein.
Figure 28B:
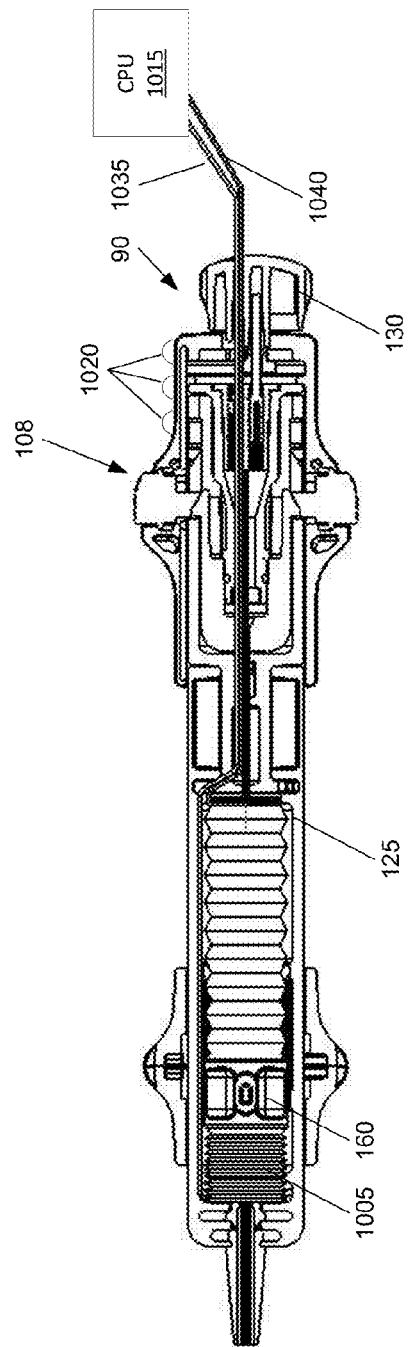

Reference is now made to FIGS. 28A-28B which are cross-sectional side views of another version of a handle 108 with a portion of a housing 125 of the handle 108 removed to reveal a rotation mechanism 90 according to the present disclosure.

As can be understood from a comparison of FIG. 27 to FIGS. 1-27, the alternative version of the rotation mechanism 90 and the surrounding elements of the handle 108 and leadless pacemaker delivery system of the version of FIGS. 28A-28B share the majority of elements and operation as discussed above with respect to FIGS. 1-27, except that the springs 155, 165 disposed between the shuttle 160 and the interior walls 135 have been replaced with a distal bellows 1005, and a proximal bellows 1010, respectively. The version of the handle 108 shown in FIGS. 28A-28B further incorporate electrical circuitry adapted to provide feedback to a user in response to the position of the shuttle 160 within the housing 108. Accordingly, the preceding discussion of FIGS. 1-27 is equally applicable to the version of the rotation mechanism 90 and surrounding elements of the handle 108 shown in FIGS. 28A-28B, except as will now be specifically discussed with respect to FIGS. 28A-28B.

As indicated in FIGS. 28A-28B, a distal bellows 1005 and a proximal bellows 1010 are coupled to distal and proximate ends of a shuttle 160, respectively. The handle 108 includes a torque portion 130 that, when rotated, causes rotation of a leadless pacemaker coupled to the handle 108 as well as translation of the shuttle 160 within the handle 108. For example, in certain implementations, clockwise (CW) rotation of the torque portion 130 causes the shuttle 160 to move proximally while counterclockwise (CCW) rotation of the torque portion 130 causes the shuttle 160 to move distally. In certain implementations, the handle 108 may include a ratchet assembly (such as the ratchet assembly of FIGS. 7A and 7B and previously discussed in this disclosure) that provides tactile feedback to a user of the handle 108 as the torque portion 130 is rotated. As previously described in this disclosure, other tactile feedback features may also be incorporated in the handle 108 to provide varying resistance to rotation of the torque portion 130 and tactile warnings to a user as the shuttle 160 translates within the housing 108. In other implementations, the shuttle 160 may be substituted with an alternative body translatable within the housing 108 in response to rotation of the torque portion 130.

As illustrated by the difference between FIGS. 28A and 28B, the proximal bellows 1010 is constructed into the handle 108 such that the proximal bellows 1010 compresses as the shuttle 160 approaches a proximal end of the handle 108. Such translation also causes expansion of the distal bellows 1005. Similarly, as the shuttle 160 is made to translate distally, the distal bellows 1005 is compressed and the proximal bellows 1010 expands. In certain implementations, the proximal bellows 1010 may be spring bellows such that as the proximal bellows 1010 is compressed, the amount of resistance to additional compression and, as a result, additional rotation of the torque portion 130 may be increased, thereby providing tactile feedback relative to the position of the shuttle 160.

The handle 108 of FIGS. 28A-28B includes electrical components adapted to determine the position of the shuttle 160 within the housing 108 and provide feedback to a user of the handle 108. More specifically, the electrical components measure or otherwise determine the position of the shuttle 160 within the housing 108 relative to one or more predetermined shuttle positions corresponding to a number of rotations of the torque portion 130. Feedback and warnings are then provided to a user based on the position of the shuttle 160, such as through illumination of one or more LEDs 1020 visible to the user.

In the implementation illustrated in FIGS. 28A-28B, the handle 108 is communicatively coupled to a computing device (CPU) 1015 configured to send and receive signals to and from the handle 108. In certain implementations, the computing device 1015 may be incorporated into the handle 108. The computing device 1015 may include at least one processor and memory that includes instructions executable by the processor to receive signals from the handle 108 and to determine a position of the shuttle 160 based on the received signals. The computing device 1015 may then transmit signals to the handle 108 that cause appropriate feedback to be provided to the user. For example, such signals from the computing device 1015 may cause one or more LEDs 1020 to illuminate. In other implementations, the computing device 1015 may instead be replaced by other circuitry configured to activate one or more feedback devices based on the position of the shuttle 160 within the housing 108. For example, in one implementation, such a circuit may include a switch coupled to a power source that, when closed by action of the shuttle 160, causes an LED to illuminate.

In the implementation illustrated in FIGS. 28A-28B, each of the distal bellows 1005 and the proximal bellows 1010 are constructed of an electrically conductive material such that the resistance of the distal bellows 1005 ad the proximal bellows 1010 vary as the bellows 1005, 1010 are compressed and expanded. The distal bellows 1005 and the proximal bellows 1010 are coupled to the computing device 1015 by a first lead 1035 and a second lead 1040 such that the computing device 1015 may monitor the resistances of the bellows 1005, 1010 and determine a corresponding position of the shuttle 160 within the housing 108. The computing device 1015 may also be coupled to the LEDs 1020 such that the computing device 1015 may illuminate one or more of the LEDs in response to the position of the shuttle 160. For example, in one implementation, the LEDs may be color coded (e.g., green, yellow, red) to indicate the relative proximity of the shuttle 160 to a predetermined location within the housing 108 and the computing device 1015 may selectively illuminate the LEDs based on the position of the shuttle 160.

In other implementations, switches, variable resistors, and other components may be used to determine the location of the shuttle 160 within the housing 108. For example, one or more limit switches may be disposed along the housing 108 such that as the shuttle 160 translates within the housing 108, the shuttle 160 closes the switches, indicating its position within the housing 108. Switch elements may also be integrated into the distal or proximal bellows 1005, 1010 such that the switches close in responses to the distal or proximal bellows 1005, 1010 being compressed or expanded. Movement of the shuttle 160 within the housing 108 resulting from rotation of the torque portion 130 may also causes changes to a variable resistance element (e.g. a potentiometer) such that the position of the shuttle 160 may be determined in response to measuring the resistance of the variable resistance element.

The use of one or more LEDs as a warning mechanism is intended only as an example and other warning mechanisms may be used to alert a user when the shuttle 106 reaches a position within the handle 108 corresponding to a specific number of rotations. For example, the handle 108 may include other components adapted to produce other types of feedback, such as vibrations or audible signals, in response to the shuttle 160 reaching certain positions within the handle 108 that correspond to predetermined numbers of rotations of a leadless pacemaker. Such feedback may be progressive such that the character or intensity of the feedback may vary based on the proximity of the shuttle 160 to one or more of the predetermined positions. For example, the volume or tone of an audible feedback signal or the intensity of a vibration may increase as the shuttle 160 approaches a predetermined position. In still other implementations, the handle 108 may include a screen or display, such as a liquid crystal display (LCD), on which information may be provided to the user of the handle 108. Such information may include, for example, a visual indicator or other visual indicator (including an actual number) corresponding to the number of rotations of the torque portion 130 of the handle 108.

To facilitate use of the handle 108 illustrated in FIGS. 28A-28B, an internal or external power source may be included in or otherwise coupled to the handle 108. For example, in certain implementations, the handle 108 may include a battery or similar internal power source which may be rechargeable and/or replaceable. Alternatively, the handle 108 may include a cord to electrically couple the handle 108 to an external power source, such as, without limitation, an external battery, a power pack, and a wall socket.

I. Example Feedback Profiles

FIGS. 27A-I illustrate different feedback profiles that may be implemented in leadless pacemaker delivery systems according to the present disclosure. In general, each feedback profile shows the resistance to rotation of a component of the leadless pacemaker delivery systems, such as the torque portion 130 of the handle 108, relative to the rotational position of the component. The example feedback profiles are intended as examples only and are not intended to limit the types of feedback profiles that may result from implementations of the present disclosure.

For purposes of this discussion, rotation is assumed to be applied by a user to a torque portion, such as torque portion 130, of a leadless pacemaker delivery system in accordance with this disclosure.

Figure 29A:
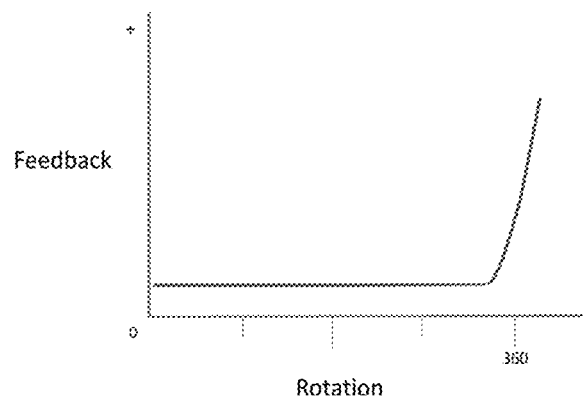
FIGS. 29A-29H are graphs illustrating feedback profiles that may be achieved in different embodiments of the leadless pacemaker delivery systems disclosed herein.

FIG. 29A is a first feedback profile illustrating one full rotation of a torque portion of a first leadless pacemaker delivery system. As shown in FIG. 29A, a base rotational resistance is provided over the majority of the rotation, however, as a full rotation nears completion, the rotational resistance rises exponentially and continues to increases the more a full rotation is exceeded.

Figure 29B:
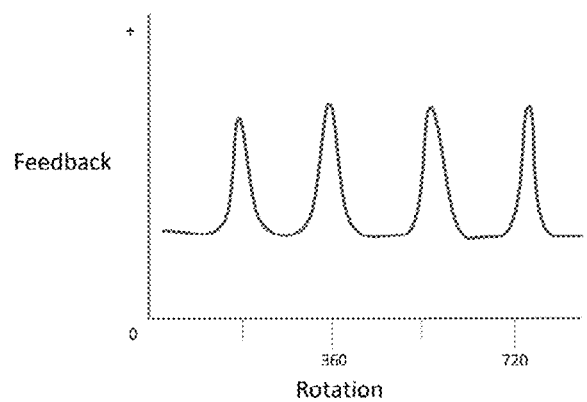

FIG. 29B is a second feedback profile illustrating two full rotations of a torque portion of a second leadless pacemaker delivery system. As shown in FIG. 29B, a based rotational resistance is provided for the majority of each rotation, however, the rotational resistance is periodically increased to indicate every half rotation (i.e., every 180 degrees).

Figure 29C:
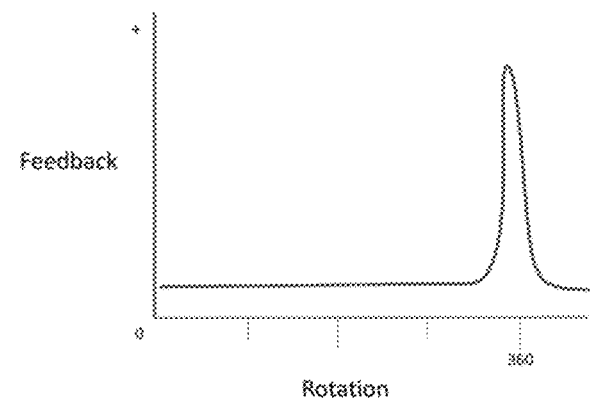

FIG. 29C is a third feedback profile illustrating one full rotation of a torque portion of a third leadless pacemaker delivery system. Similar to the feedback profile illustrated in FIG. 29A, a base rotational resistance is provided over the majority of the rotation, however, as a full rotation nears completion, the resistance rises to provide an indication of the rotation to a user. In contrast to the feedback profile of FIG. 29A, additional rotation of the rotational resistance causes the rotational resistance to fall back to the base rotational resistance.

Figure 29D:
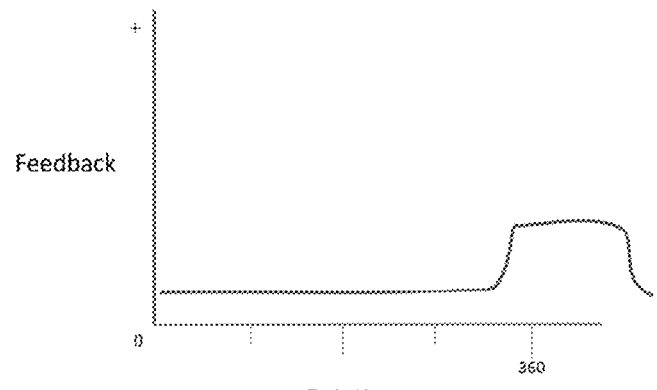

FIG. 29D is a fourth feedback profile illustrating one full rotation of a torque portion of a fourth leadless pacemaker delivery system. Similar to the feedback profile illustrated in FIG. 29C, a base rotational resistance is provided over the majority of the rotation, however, as a full rotation nears completion, the resistance rises to provide an indication of the rotation to a user. In contrast to the feedback profile of FIG. 29D, the increased rotational resistance is maintained for approximately one quarter rotation before returning to the base rotational resistance.

Figure 29E:
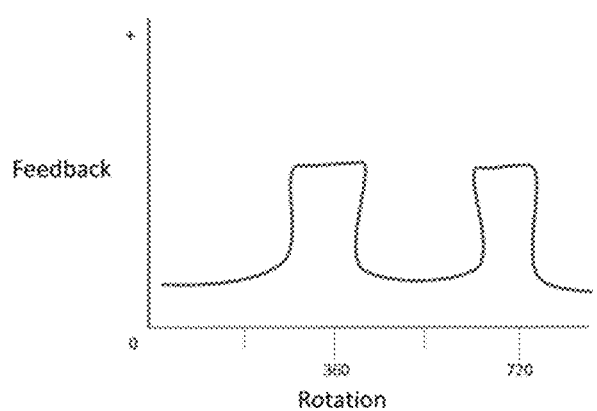

FIG. 29E is a fifth feedback profile illustrating two full rotations of a torque portion of a fifth leadless pacemaker delivery system. Similar to the feedback profile illustrated in FIG. 29D, a base rotational resistance is increased and maintained as a first rotation is completed. The increased rotational resistance is maintained for approximately one half turn before returning to the base rotational resistance. A second increase in the rotational resistance then occurs in response to the completion of a second rotation.

Figure 29F:
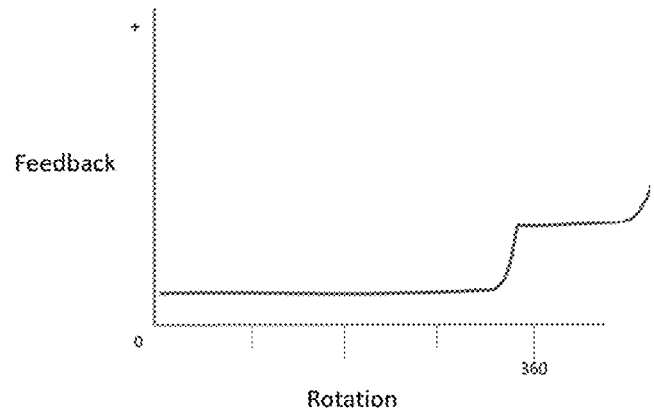

FIG. 29F is a sixth feedback profile illustrating one full rotation of a torque portion of a sixth leadless pacemaker delivery system. The feedback profile illustrated in FIG. 29F combines aspects of the feedback profiles of FIG. 29A and that of FIG. 29D. More specifically, a base rotational resistance is increased in response to completion of a first rotation. The increased rotational resistance is then maintained for approximately one quarter rotation before the rotational resistance continues to increase exponentially.

Figure 29G:
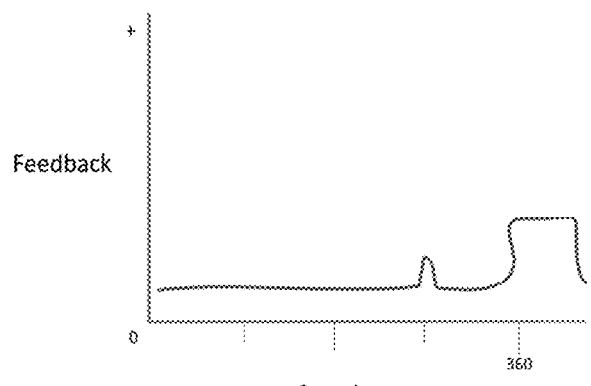

FIG. 29G is a seventh feedback profile illustrating one full rotation of a torque portion of a seventh leadless pacemaker delivery system. Similar to the feedback profile illustrated in FIG. 29D, a base rotational resistance is increased and maintained as a first rotation is completed. The increased rotational resistance is maintained for approximately one half turn before returning to the base rotational resistance. However, the feedback profile of FIG. 29G further includes a brief increase in rotational resistance at approximately three quarter rotations. Accordingly, the brief increase may server as a preliminary indication that a full rotation is near completion.

Figure 29H:
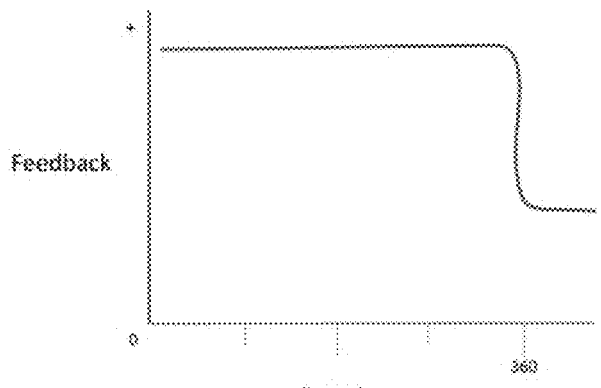

FIG. 29H is an eighth feedback profile illustrating one full rotation of a torque portion of an eighth leadless pacemaker delivery system. In contrast to the previous feedback profiles of FIGS. 29A-29G, the eighth feedback profile includes a decrease in rotational resistance from a base rotational resistance to a reduced rotational resistance in response to completing a full rotation.

The foregoing example feedback profiles were described in the context of one or two full rotations for clarity only. Accordingly, the illustrated feedback profiles or variations thereof may be modified such that they occur over a quantity of rotations other than one or two full rotations. For example and as previously disclosed in the context of FIGS. 10A-11B, fixation of a leadless pacemaker into cardiac tissue may generally require two and one quarter rotations. As a result, the foregoing feedback profiles may be offset or modified to include a change in rotational resistance corresponding to two and one quarter rotations or otherwise be based around a two and one quarter rotation target.

While the above-described rotation mechanism and its various warning mechanisms are discussed in the context of a leadless pacemaker delivery device, those skilled in the art will readily understand that the rotation mechanism and its various warning mechanisms may be employed with other medical devices such as, for example, minimally invasive surgery (MIS) tools, including for example, endoscopic devices, laparoscopic devices, and similar devices. The rotation mechanism and its various warning mechanisms may be employed with tools for the delivery and fixation of a standard implantable lead, for the delivery, fixation and/or actuation of other implantable devices. Example of actuating an implanted devices include turning on an implantable device, opening a valve, causing a device to change states, etc., wherein any of these actuations or operational settings may be achieved via rotation of an element of the implanted device via the above-described rotation mechanism, and the rotation should be measured to prevent damage to the device and/or body tissue, the measured rotation being made possible via the warning mechanisms described herein.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A medical tool comprising:
   a handle including:
   a housing;
   a torque portion operably coupled to the housing and rotatable relative to the housing, the torque portion including a shaft having an outer circumferential surface and a helical thread portion radially outwardly extending from the outer circumferential surface of the shaft;
   a shuttle including a shuttle thread, wherein the shuttle is mounted on the shaft and is longitudinally displaceable along the shaft via threaded interaction between the shuttle thread and the helical thread portion when the torque portion rotates relative to the housing; and
   a warning mechanism that provides a tactile indication when the torque portion has rotated a number of rotations, wherein the warning mechanism includes a first structural feature of one of the housing and the shaft and a second structural feature of the shuttle that contacts the first structural feature as the shuttle displaces along the shaft.

2. The medical tool of claim 1, wherein the first structural feature is a first bump disposed on the housing, and the second structural feature is a second bump, at least one of the first bump or the second bump adapted to deflect as the shuttle displaces along the shaft, the deflection providing the tactile indication.

3. The medical tool of claim 2, wherein the tactile indication includes a period of increased rotational resistance at the torque portion as the at least one of the first bump or the second bump is deflected.

4. The medical tool of claim 1, wherein the first structural feature is a bump disposed on the shaft and the second structural feature is a proximal portion of the shuttle.

5. The medical tool of claim 4, wherein the shuttle comprises a plurality of shuttle segments and a compliant member extending around the shuttle, the compliant member resisting separation of the shuttle segments, the tactile indication provided by the shuttle segments separating in response to the proximal portion shuttle contacting the bump.

6. The medical tool of claim 1, wherein one or more of the helical thread portion or the shuttle thread comprises a malleable thread, and wherein the tactile indication is provided by one or more of deformation or failure of the malleable thread.

7. The medical tool of claim 6, wherein the helical thread portion comprises the malleable thread.

8. The medical tool of claim 6, wherein the shuttle thread comprises the malleable thread.

9. The medical tool of claim 1, wherein the medical tool is a delivery system for delivering a leadless pacemaker into cardiac tissue.

10. The medical tool of claim 1 further comprising:
    a catheter shaft coupled to the housing; and
    a linear member extending through the catheter shaft, wherein the linear member is coupled to the torque portion such that rotation of the torque portion relative to the housing causes the linear member to rotate relative to the catheter shaft.

11. The medical tool of claim 10 further comprising a leadless pacemaker coupled to the linear member.

12. The medical tool of claim 1, wherein the tactile indication includes a change in resistance to rotation of the torque portion relative to the housing when the first structural feature contacts the second structural feature.

13. The medical tool of claim 12, wherein the change in resistance to rotation is an increase in resistance to rotation.

* * * * *